(12) United States Patent
Mach et al.

(10) Patent No.: US 7,612,085 B2
(45) Date of Patent: Nov. 3, 2009

(54) SIGMA 2 RECEPTOR LIGANDS AND THERAPEUTIC USES THEREFOR

(75) Inventors: Robert H. Mach, Eureka, MO (US); Zhude Tu, Eureka, MO (US); Wenhua Chu, St. Louis, MO (US); Suwanna Vangveravong, Ballwin, MO (US); Richard Hotchkiss, Chesterfield, MO (US); William Hawkins, Olivette, MO (US); Rebecca Aft, Chesterfield, MO (US)

(73) Assignee: Washington University, St. Louis, MO (US)

( * ) Notice: Subject to any disclaimer, the term of this patent is extended or adjusted under 35 U.S.C. 154(b) by 17 days.

(21) Appl. No.: 11/776,533

(22) Filed: Jul. 11, 2007

(65) Prior Publication Data
US 2008/0161343 A1 Jul. 3, 2008

Related U.S. Application Data

(60) Provisional application No. 60/806,990, filed on Jul. 11, 2006.

(51) Int. Cl.
*A01N 43/42* (2006.01)
*A61K 31/44* (2006.01)
*C07D 221/02* (2006.01)
(52) U.S. Cl. .................. 514/299; 546/112; 546/183
(58) Field of Classification Search ................. 546/124, 546/183, 112; 514/299, 304
See application file for complete search history.

(56) References Cited

OTHER PUBLICATIONS

Efange et al., Journal of Medicinal Chemistry (1997), 40(24), 3905-3914.*
Vangveravong et al., Bioorganic & Medicinal Chemistry (2006), 14(20), 6988-6997.*
Aydar et al., Cancer research, (Aug. 1, 2004) vol. 64, No. 15, pp. 5029-5035. Ref: 100.*
Barbieri et al, Novel sigma binding site ligands as inhibitors of cell proliferation in breast cancer. Oncology Research, 2003, 13:455-461.
Bonhaus et al, [3H]BIMU-1, a 5-hydroxytryptamine3 receptor ligand in NG-108 cells, selectively labels sigma-2 binding sites in guinea pig hippocampus. Pharmacol. Exp. Ther. 1993, 267:961-970.
Bowen et al, CB-64D and CB-184: ligands with high sigma 2 receptor affinity and subtype selectivity. Eur. J. Pharmacol. 1995, 278:257-260.
Brent et al, The sigma receptor ligand, reduced haloperidol, induces apoptosis and increases intracellular-free calcium levels [Ca2+] in colon and mammary adenocarcinoma cells. Biochemical & Biophysical Research Communications, 1996, 219:219-226.
Choi et al, Development of a Tc-99m labeled sigma-2 receptor-specific ligand as a potential breast tumor imaging agent. Nuclear Medicine & Biology, 2001, 28:657-666.
Crawford and Bowen, Sigma-2 receptor agonists activate a novel apoptotic pathway and potentiate antineoplastic drugs in breast tumor cell lines. Cancer Res. 2002, 62:313-322.
Hellewell et al, Rat liver and kidney contain high densities of sigma 1 and sigma 2 receptors: characterization by ligand binding and photoaffinity labeling. Eur. J. Pharmacol., Mol. Pharmacol. Sec. 1994, 268:9-18.
Huang et al, Synthesis and structure-activity relationships of N-(1-benzylpiperidin-4-yl)arylacetamide analogues as potent sigma1 receptor ligands. J Med Chem, 2001, 44:4404-4415.
Huang et al, Synthesis and quantitative structure-activity relationships of N-(1-benzylpiperidin-4-yl)phenylacetamides and related analogues as potent and selective sigma1 receptor ligands. Journal of Medicinal Chemistry, 1998, 41:2361-2370.
John et al, Synthesis, In Vitro Binding, and Tissue Distribution of Radioiodinated 2-[125I]N-(N-Benzylpiperidin-4-yl)-2-Iodo Benzamide, 2-[125I]BP: A Potential Sigma Receptor Marker for Human Prostate Tumors. Nuclear Medicine & Biology, 1998, 25: 189-194.
Kawamura et al, Synthesis and evaluation of 11C- and 18F-labeled 1-[2-(4-alkoxy-3-methoxyphenyl)ethyl]-4-(3-phenylpropyl)piperazines as sigma receptor ligands for positron emission tomography studies. Nuclear Medicine & Biology, 2003, 30:273-284.
Mach et al, Preparation of a technetium-99m SPECT agent for imaging the sigma-2 receptor status of solid tumors. J Labelled Cpd Radiopharm, 2001, 44: 899-908.
Mach et al, Conformationally-flexible benzamide analogues as dopamine D3 and sigma2 receptor ligands. Bioorganic & Medicinal Chemistry Letters, 2004, 14:195-202.
Mach et al, [18F]N-4'-Fluorobenzyl-4-(3-bromophenyl) acetamide for imaging the sigma receptor status of tumors: comparison with [18F]FDG and [125I]IUDR. Nuclear Medicine & Biology, 2001, 28:451-458.
Mach et al, Sigma2 receptors as potential biomarkers of proliferation in breast cancer. Cancer Res. 1997, 57:156-161.

(Continued)

*Primary Examiner*—D. Margaret Seaman
*Assistant Examiner*—Niloofar Rahmani
(74) *Attorney, Agent, or Firm*—Sonnenschein, Nath and Rosenthal LLP

(57) ABSTRACT

A series of N-substituted 9-azabicyclo[3.3.1]nonan-3α-yl phenylcarbamate analogs are disclosed, as well as methods of their preparation. Their affinities for sigma (σ1 and σ2) receptors are described. Two new compounds, N-(9-(4-aminobutyl)-9-azabicyclo[3.3.1]nonan-3α-yl)-N'-(2-methoxy-5-methylphenyl)carbamate and N-(9-(6-aminohexyl)-9-azabicyclo[3.3.1]nonan-3α-yl)-N'-(2-methoxy-5-methylphenyl)carbamate, are shown to have a high affinity and selectivity for σ2 versus σ1 receptors. Among the disclosed compounds are biotinylated and fluorescent analogs. These compounds can serve as probes to the σ2 receptor. In addition, some disclosed compounds can induce apoptotic cell death by both caspase-dependent and caspase-independent mechanisms, and are effective for treatment of tumors. The compounds can be used as chemotherapeutics or chemosensitizers in the treatment of a wide variety of solid tumors.

3 Claims, 19 Drawing Sheets

OTHER PUBLICATIONS

Mach et al, Synthesis of N-substituted 9-azabicyclo[3.3.1]nonan-3alpha-yl phenylcarbamate analogs as sigma-2 receptor ligands. Med. Chem. Res. 2003, 11:380-398.

Mach et al, Synthesis and sigma receptor binding affinities of 8-azabicyclo[3.2.1]octan-3alpha-yl and 9-azabicyclo [3.3.1]nonan-3alpha-yl phenyl carbamates. Med. Chem. Res. 2001, 10:339-355.

Nguyen et al, Comparison of binding parameters of sigma 1 and sigma 2 binding sites in rat and guinea pig brain membranes: novel subtype-selective trishomocubanes. Eur. J. Pharmacol. 1996, 311:233-240.

Ostenfeld et al, Effective tumor cell death by sigma-2 receptor ligand siramesine involves lysosomal leakage and oxidative stress. Cancer Res. 2005, 65:8975-8983.

Tu et al, Carbon-11 labeled sigma2 receptor ligands for imaging breast caner. Nuclear Medicine and Biology, 2005, 32:423-430.

Vangveravong et al, Synthesis of N-substituted 9-azabicyclo[3.3.1]nonan-3alpha-yl carbamate analogs as sigma2 receptor ligands. Bioorg. Med. Chem. 2006, 14: 6988-6997.

Xu et al, [3H]N-[4-(3,4-dihydro-6,7-dimethoxyisoquinolin-2(1H)-yl)butyl]-2-methoxy-5-methylbenzamide: a novel sigma-2 receptor probe. Eur. J. Pharmacol. 2005, 525:8-17.

* cited by examiner

Excitation and emission spectra of 9.

Azabicyclononane Analogs

SV 170

WC-II-26

SV 119

SV 166

Tropane Analog

RHM-I-138

B

C

SV119

WC-II-26

RHM-I-138

SIGMA 2 RECEPTOR LIGANDS AND THERAPEUTIC USES THEREFOR

CROSS-REFERENCE TO RELATED APPLICATIONS

This application claims the benefit of prior filed U.S. provisional application Ser. No. 60/806,990, filed Jul. 11, 2006, the specification of which is herein incorporated by reference in its entirety.

GOVERNMENT SUPPORT

This research was funded at least in part by NIH Grant CA102869, NIH Grant EB1729, NIH Grant CA121952, and the U.S. Army Medical Research and Material Command under DAMD 17-01-1-0446.

INTRODUCTION

Sigma receptors represent a class of proteins that were initially thought to be a subtype of the opiate receptors.[1] The development of sigma-selective ligands, such as (+)-pentazocine, DTG (1,3-di-o-tolylguanidine), and (+)-3-PPP (3-(3-hydroxyphenyl)-N-(1-propyl)piperidine), allowed sigma binding sites to be distinguished as a separate receptor system.[2] It is now widely accepted that there are at least two classes of sigma binding sites, denoted sigma-1 (σ1) and sigma-2 (σ2). These receptors are distinguishable functionally, pharmacologically, and by molecular size. The σ1 receptor has a molecular weight of ~25 kDa, whereas the σ2 receptor has a molecular weight of ~21.5 kDa. The σ1 receptor gene has been cloned from guinea pig liver, human placental choriocarcinoma, rat brain, and mouse kidney, and displays a 30% sequence identity with the enzyme, yeast sterol isomerase.[3-5] The σ2 receptor gene has not been cloned, although a number of studies have presented evidence linking the σ2 receptor to potassium channels and intracellular calcium release in NCB-20 cells.[2,6] Radioligand binding studies using [³H](+)-pentazocine and [³H]DTG have revealed that both σ1 and σ2 receptors have a widespread distribution in the central nervous system and in a variety of tissues and organs[2,6] However, since [³H]DTG possesses a similar affinity for σ1 and σ2 receptors, in vitro binding studies using this radiotracer to measure σ2 receptor density require the use of the 100 nM (+)-pentazocine in the binding assay in order to mask σ1 receptors.

Previous studies have reported that σ2 receptors are overexpressed in a wide variety of human and murine tumor cells grown in cell culture.[7-9] Furthermore, it has been shown that the density of σ2 receptors can be higher in proliferative versus quiescent tumor cells in vitro[9,10] and in vivo.[11] For example, Wheeler et al. determined that σ2 receptors were expressed ~10-fold greater in proliferative tumor cells compared to quiescent tumor cells in tumors grown in female nude mice.[11]

Apoptosis (programmed cell death) is a physiological process that is very important for development, homeostasis and suppression of oncogenesis[27]. Dysregulated apoptosis has been implicated in many diseases including degenerative conditions, ischemic stroke and cancer[28]. It is well known that the caspase protease family plays a central role in apoptosis. Caspase-3 and caspase-7, the "executioner" caspases, are key enzymes which degrade proteins such as gelsolin and lamin, leading to cell death[28]. Several σ2 selective ligands with different chemical structures have been reported to induce apoptosis in several tumor cell lines[12, 29, 30]. However, the mechanism of σ2 receptor-induced cell death is still not clear, as some studies have shown that σ2 receptor ligands can induce apoptosis via a non-caspase mediated pathway[12, 13].

A number of structurally diverse compounds have been shown to possess a high affinity to sigma receptors. Most of these compounds display either a high selectivity for the σ1 receptor or bind with approximately equal affinity to both σ1 and σ2 receptors. Until recently, only a few σ2 selective ligands have been identified. For example, the phenyl morphan CD-184,[14] the trishomocubane analog ANSTO-20,[15] and the potent 5-HT$_3$ and 5-HT$_4$ ligand, BIMU-1,[16] have been shown to possess a moderate affinity and selectivity for σ2 versus σ1 receptors. We previously reported the synthesis and in vitro binding of a series of N-substituted-9-azabicyclo [3.3.1]nonan-3α-yl carbamate analogs having a modest affinity and selectivity for σ2 versus σ1 receptors.[17,18]

SUMMARY

The present inventors have prepared a series of N-substituted-9-azabicyclo[3.3.1]nonan-3α-yl carbamate analogs, including radiolabeled, fluorescent, and biotinylated analogs. In various configurations, these compounds have affinity for σ receptors, and can be selective for either the σ1 receptor or the σ2 receptor. In various embodiments, a disclosed compound can be used as a probe selective for a σ receptor, in particular a σ2 receptor. In various aspects, the present teachings disclose structure-activity relationships of groups attached to the bridgehead nitrogen atom of the granatane ring system, with respect to activity of the disclosed compounds as probes for the σ2 receptor.

In other aspects, the present inventors demonstrate that σ2 selective ligands induce cell death in EMT-6 cells. They also show the activation of caspase-3/7 during the cell death process, demonstrating that a caspase-dependent apoptosis pathway is involved. Nuclear DNA fragmentation can be detected by fluorescence microscopy and quantified by flow cytometry. Flow cytometry studies show that some of the σ2 activated EMT-6 cells are positive for annexin V (a marker of early apoptosis), but negative for 7-aminoacridine (7AAD, a marker of late apoptosis), and some of the cells are positive for both annexin V and 7AAD. Finally, EMT-6 cells treated with a σ2 selective ligand disclosed herein exhibit procaspase-3 and PARP-1 cleavage. These data indicate that our σ2 selective ligands are potent inducers of cell death. Without being limited by any theory, these σ2 selective ligands may act, at least partly, by a caspase-dependent apoptotic mechanism.

In some aspects, the σ2 selective ligands disclosed herein can be used therapeutically as anticancer or chemosensitizing agents.[12,13]. In some configurations, a σ2 selective ligand disclosed herein can be used in conjunction with other chemotherapeutic agents. Accordingly, some aspects of the present teachings include methods of treating a subject in need of cancer therapy. These methods comprise administering to the subject a σ2 selective ligand disclosed herein, in an amount effective for cancer chemotherapy. In some aspects, one or more σ2 selective ligands disclosed herein can be administered as a component of a pharmacological composition such as a mixture further comprising one or more adjuvants, salts, buffers and/or other standard components of pharmaceutical compositions and formulations. Such formulations can be developed using routine methods well known to skilled artisans.

In some aspects, an amount effective for chemotherapy can be an amount effective for sensitizing tumor cells to a chemotherapeutic agent. Accordingly, some aspects of the methods further include administering a chemotherapeutic agent to the subject, such as, without limitation, doxorubicin, colchicine, adriamycin, vinblastine, digoxin, saquinivir, cisplatin or paclitaxel. Methods of administration, and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. In various configurations, the tumor cells can be any tumor cells which exhibit elevated levels of a σ2 receptor in proliferative tumor cells in comparison to quiescent tumor cells, such as, without limitation, tumor cells of breast, lung, pancreas or brain.

In various embodiments, the present results provide information on the structure-activity relationships of 9-azabicyclo [3.3.1]nonan-3α-yl carbamate analogs with respect to binding at σ1 and σ2 receptors. The length of the methylene spacer group separating the primary amino group and the bridgehead nitrogen atom affects the binding affinity for σ2 receptors and σ1:σ2 selectivity ratio. Compound 1b, comprising a $C_6$ linear alkyl chain, has the highest affinity and selectivity for σ2 versus σ1 receptors of the compounds tested. Substitution of benzyl or benzoyl groups attached to the amino side chain (2a-f, 3a-f, and 4a-d) does not enhance the selectivity for σ2 versus σ1 receptors. Furthermore, the attachment of a shorter chain biotin moiety to either 1b or 1c gave compounds 5 and 6 with moderate affinity and selectivity for σ2 receptors. Finally, a dansyl derivative, compound 9, has a moderate affinity and selectivity for σ2 receptors and is a useful probe for two-photon microscopy studies of this receptor in cells growing under cell culture conditions and in tissue slices.

In various embodiments, compounds of the present teachings comprise aminoalkyl substituents attached to the bridgehead nitrogen of an N-substituted-9-azabicyclo[3.3.1]nonan-3α-yl carbamate. The length of the spacer group, such as a linear alkyl group separating a primary amino group and the bridgehead nitrogen atom, can be from about that of a linear $C_4H_8$ group to about that of a linear $C_{10}H_{20}$ group. In various aspects, a spacer can comprise atomic species in addition to or instead of carbon and hydrogen and need not be a linear chain, and can comprise, for example, an aliphatic ring, an aromatic ring, and/or one or more heteroatoms such as S, Si, N, O, or P. In various configurations, a spacer can comprise from one up to about twenty methylene units, such as, in non-limiting example, four, six, or ten methylene units.

In various configurations, the primary amino group in an amino alkyl substituent can serve as the point of attachment of a label, such as, without limitation, a radioisotope, a fluorophore, or a hapten such as biotin. In addition, in various aspects, the spacer such as a $C_{4-10}$ alkyl chain can separate the label from the σ2 receptor recognition fragment, i.e., the 9-azabicyclo[3.3.1]nonan-3α-yl carbamate moiety.

Accordingly, various embodiments of the present teachings include biotinylated N-substituted-9-azabicyclo[3.3.1] nonan-3α-yl carbamate analogs. In various aspects, these biotinylated compounds can be used as probes for σ2 receptors, and can be used, for example, in the identification, localization, and/or purification of an σ2 receptor. Other aspects of the present teachings include fluorescent N-substituted-9-azabicyclo[3.3.1]nonan-3α-yl carbamate analogs. In various aspects, these compounds can be used for tissue, cellular or sub-cellular σ2 receptor localization, such as localization of an σ2 receptor within tumor cells, using fluorescence microscopy, including two-photon microscopy.

The present inventors also disclose σ2 selective ligands which induce cell death and increase caspase-3/7 activity in a dose-dependent manner. Accordingly, aspects of the present teachings include methods of inducing cell death, methods of increasing caspase-3/7 activity, and combinations thereof. These methods comprise contacting cells with at least one σ2 ligand, such as a σ2 ligand disclosed herein. Accordingly, in various aspects of the present teachings, the present inventors disclose methods of treating a cancer. These methods comprise administering to a subject in need of treatment at least one chemotherapeutic agent and at least one σ2 ligand.

DETAILED DESCRIPTION

Figure 1:
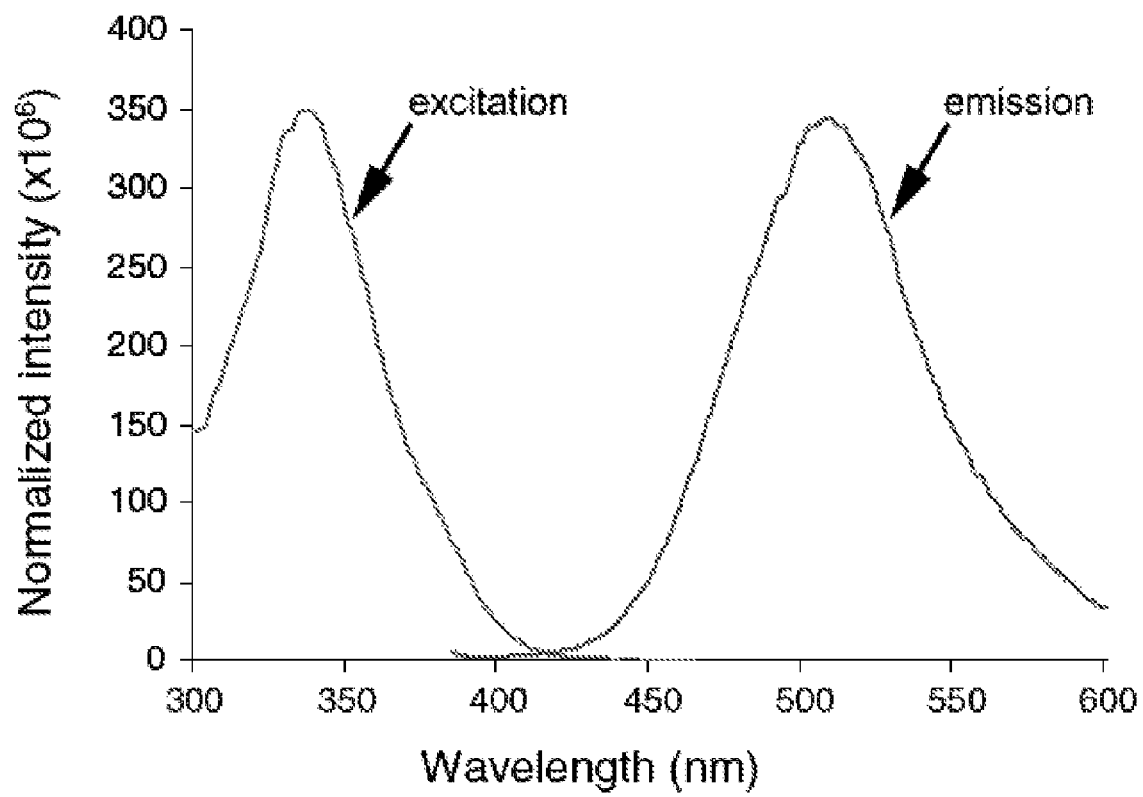
FIG. 1 illustrates excitation and emission spectra of compound 9.

The present teachings disclose various N-substituted-9-azabicyclo[3.3.1]nonan-3α-yl carbamate analogs. Various compounds of these teachings can selectively bind a σ receptor, which, in various embodiments, can be a σ2 receptor.

The present inventors also disclose induction of cell death using σ-2 selective ligands. In various aspects, these ligands can both induce cell death and increase caspase-3/7 activity in a dose-dependent manner. The most potent σ-2 selective ligands, WC-II-26, SV119, and RMH-I-138 (below) had EC$_{50}$s of 12.5 µM, 11 µM and 16 µM, respectively, after a 48 hour treatment. After a 24 hour treatment with 40 µM of WC-II-26, SV119 and RMH-I-138, the activity of endogenous caspase-3/7 increased approximately 7-, 2-, and 2-fold, respectively, when compared with untreated cells. Fluorescent Terminal transferase dUTP nick end labeling (TUNEL) staining showed that these three σ2 selective ligands induced DNA fragmentation, a hallmark of apoptosis. Flow cytometry studies detected positive annexin V labeling and active caspase-3 staining, also hallmarks of apoptosis. These studies further showed that some of the σ2 activated EMT-6 cells were not only positive for annexin V (an early marker for apoptosis) but also were negative for 7AAD, and some of the cells were positive for both annexin V and 7 AAD (a marker of late apoptosis). Furthermore, the caspase-3 specific inhibitor, Z-DEVD-FMK, and the pancaspase inhibitor, Z-VAD-FMK, partially, but not completely, blocked the cytotoxic effects of these three σ2 selective ligands.

The activation of caspase-3/7 by these three σ2 selective ligands was further confirmed by the detection of pro-caspase-3 and PARP-1 cleavage products using Western blot analysis. In conclusion, the σ2 selective ligands of the present teachings appear to induce apoptotic cell death by both caspase-dependent and caspase-independent mechanisms and, as a consequence, have efficacy in tumors that have a loss of function mutation in the apoptosis pathway. Accordingly, these σ2 receptor ligands can function as chemotherapeutics and as chemosensitizers in the treatment of a wide variety of solid tumors.

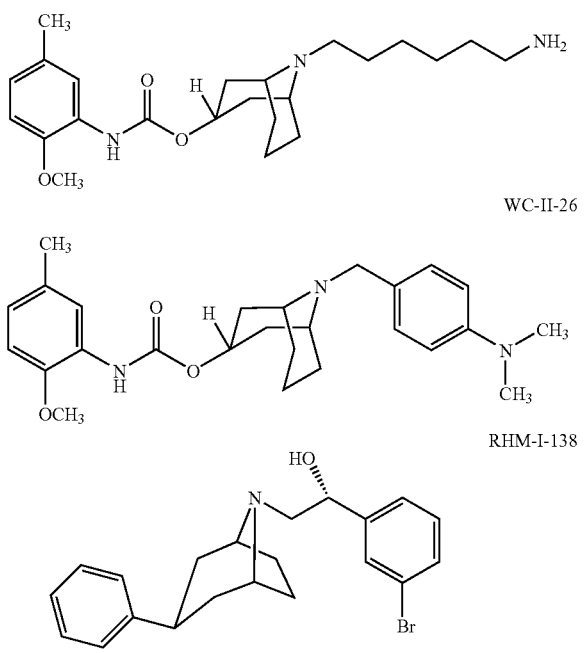

The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999, and textbooks such as Hedrickson et al., Organic Chemistry $3^{rd}$ edition, McGraw Hill, New York, 1970.

Cell culture conditions. EMT-6 mouse breast tumor cells[39] were cultured in DMEM, supplemented with 10% fetal bovine serum. The cells were maintained at 37° C. in a humidified incubator with a 5% CO2/95% air atmosphere.

Cytotoxicity assay. The cytotoxic effect of the sigma ligands on EMT-6 cells was measured using the MTS colorimetric assay. MTS is bioreduced by cells into a colored formazan product with an absorbance at 490 nm. The quantity of the products is directly proportional to the number of viable cells in the culture. The MTS assay was performed using the CellTiter96Aqueous One Solution Assay (Promega, Madison, Wis.) according to the manufacturer's protocol. Briefly, EMT-6 cells were seeded at $2\times10^3$/well in 96-well plates on the day prior to treatment with the sigma ligand. Each sigma ligand was first dissolved in DMSO, and then serially diluted to get the desired concentration. The final concentration of DMSO in the cell culture medium was no more than 0.5%. After a 24 hour or 48 hour treatment with the various sigma ligands, cell death was assessed as follows. The CellTiter 96 Aqueous One Solution Reagent was added to each well, and the plate was incubated for 2 hours at 37° C. The plate was then read at 490 nm in a Victor 3 plate reader (PerkinElmer Life and Analytical Sciences, Shelton, Conn.). The $IC_{50}$, defined as the concentration of the sigma ligand required to inhibit cell growth by 50% relative to untreated cells, was determined from the dose-response curves after a 24 hour or 48 hour treatment.

To determine the effect of blocking the caspase-dependent apoptotic pathway on sigma ligand-induced cell killing, the caspase inhibitors, Z-VAD-FMK or Z-DEVD-FMK (Calbiochem, San Diego, Calif.) were added to the culture medium 1 hour before the sigma ligands, and the MTS assay performed as described above.

Detection of intracellular cellular caspase-3/7 activity. The activation of endogenous caspase-3/7 by the sigma ligands was measured using the CellProbe HT caspase-3/7 whole cell assay (Beckman Coulter, Fullerton, Calif.). The cell permeable, nonfluorescent bisamide substrate, Z-DEVD-R110, was added to the intact cells to detect apoptosis. Upon specific cleavage by caspase-3/7, Z-DEVD-R110 is converted to a fluorescent compound, and the fluorescent signal can be measured as follows. After adding the substrate, Z-DEVD-R110, to the cells treated with a sigma ligand, the plate was incubated for an additional 1.5-2 hour, and the resulting fluorescence measured using a Victor 3 microplate fluorometer at excitation and emission wavelengths of 485 nm and 535 nm, respectively.

Detection of apoptosis by fluorescence microscopy. The DNA fragmentation occurring during apoptosis was detected by the TUNEL staining method using the in situ cell death detection kit purchased from Roche Applied Science (Indianapolis, Ind.). Briefly, after treatment of EMT-6 cells with the sigma ligands, cells were fixed for 1 hour with 4% paraformaldehyde in phosphate buffered saline at room temperature and permeabilized with 0.1% Triton X-100 for 2 minutes on ice. The cells were then labeled by incubation with the TUNEL reaction mixture for 1 hour at 37° C. and analyzed using a Nikon inverted fluorescence microscope with a FITC filter.

Detection and quantification of apoptosis by flow cytometry. The early stages of apoptosis are characterized by translocation of phosphatidyl serine (PS) from the inner surface of the plasma membrane to the outer surface of the membrane. Annexin V, a protein with high affinity for PS, was used to detect the externalization of PS. In these experiments cell death was quantified flow cytometrically using both an annexin V assay (Apoptosis Detection Kit, R &D Systems, Minneapolis, Minn.) and a TUNEL assay (Apodirect Kit, BD Biosciences Pharmingen, San Diego, Calif.). All of the data was collected and analyzed using a FACS scan flow cytometer (Becton Dickinson, Fullerton, Calif.).

Western blot analysis. EMT-6 cells (3×105) were plated in 100 mm culture dishes 1 day prior treatment with the σ2 selective ligands. After incubation for 24 hours, the cells were treated with WC-II-26 (40 μM), SV119 (100 μM), or RHM-I-138 (40 μM) for various periods of time in DMEM medium containing 10% of fetal bovine serum. At various time points, cells were harvested, and cell lysates prepared using Chaps buffer (50 mM Pipes/HCl, pH 6.5, 2 mM EDTA, 0.1% Chaps, 20 μg/ml Leupeptin, 10 μg/ml pepstatin A, and 10 μg/ml aprotinin). Aliquots of protein (30 μg) from each sample were analyzed using standard immunoblotting procedures. Caspase-3 was blotted with the anti-caspase-3 antibody (Cell Signaling Technology, Danvers, Mass.) at a 1:1,000 dilution and horseradish peroxidase-conjugated goat anti-rabbit IgG (Cell Signaling Technology, Danvers, Mass.) at 1:3,000 dilution. For detection of the secondary antibody, the SuperSignal WestDura Extended Duration Substrate assay kit (Pierce Biotechnology, Inc. Rockford, Ill.) was used.

Statistical analyses. Results are expressed as mean ±S.D. based on at least two or three separate experiments performed in triplicate. Differences among groups were statistically analyzed by student t-test. Comparison between two experimental groups was based on 2-tailed t-test. A p value less than 0.05 was considered significant.

Syntheses of compounds of the present teachings are outlined in Schemes 1-6. Scheme 1 discloses the reaction between the secondary amine 10[17,18] and N-(ω-bromoalkyl) phthalimides to yield the intermediates compounds 11a-c. Treatment with anhydrous hydrazine yields the primary amines 1a,b. In Scheme 1, n can be an integer ranging from 1 to about 20, such as 4, 6, 8, or 10. Reductive amination of compounds 1a-c with halo-benzaldehydes and sodium borohydride afforded the N-halobenzyl derivatives (2a-f and 3a-f) (Scheme 2). In Scheme 2, n can be an integer ranging from 1 to about 20, such as 4, 6, 8, or 10. In compounds 2a, 2b, 2c, 2d, 2e and 2f, n=4. In compounds 3a, 3b, 3c, 3d, 3e, and 3f, n=6. Reaction of amine 1b with 4-halobenzoic acids will yield the 4-halobenzoyl derivatives (4a-d) (Scheme 3). In Scheme 3, n can be an integer ranging from 1 to about 20, such as 4, 6, 8, or 10. In compounds 4a, 4b, 4c and 4d, n=6.

Compounds 1b and 1c can be condensed with (+)-biotin N-hydroxysuccinimide ester to yield compounds 5 and 6 (Scheme 4) in moderate yield (75% and 78%, respectively). In Scheme 4, n can be an integer ranging from 1 to 20, such as 4, 6, 8, or 10, and m can be an integer ranging from 1 to about 20, such as 3. Similarly, compounds 1b and 1c can also be condensed with (+)-biotinamidocaproate N-hydroxysuccinimidyl ester to yield compounds 7 and 8 (Scheme 5) in high yield (88% and 95%, respectively). In Scheme 5, n can be an integer ranging from 1 to 20, such as 4, 6, 8, or 10; m can be an integer ranging from 1 to about 20, such as 3, and p can be an integer ranging from 1 to about 20, such as 5. A fluorescent analog, compound 9, can be prepared by reacting compound 1b with dansyl chloride as outlined in Scheme 6.[19] In Scheme 6, n can be an integer from 1 to about 20, such as 6.

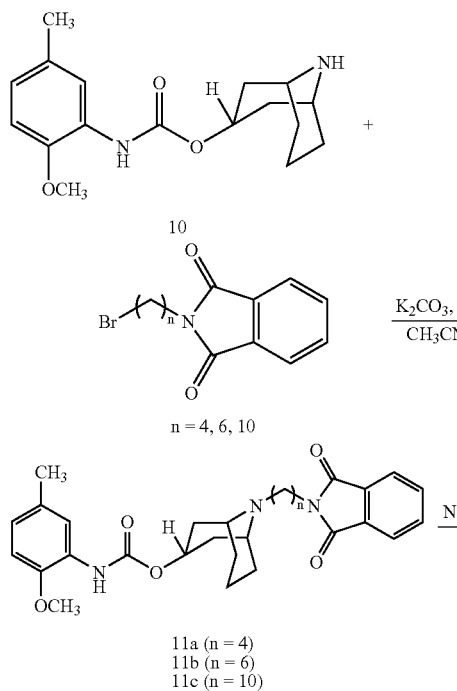

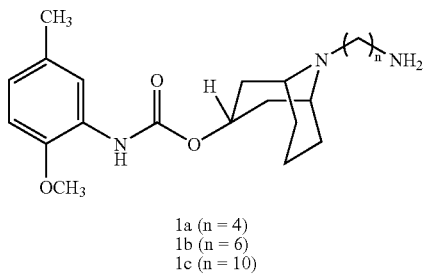

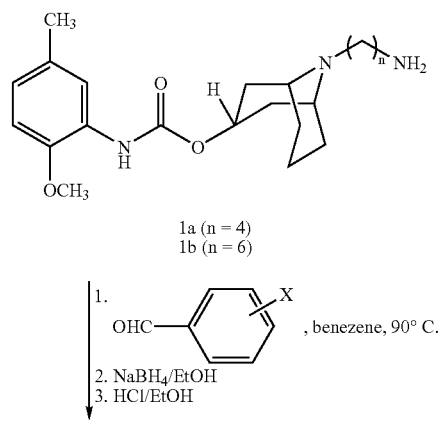

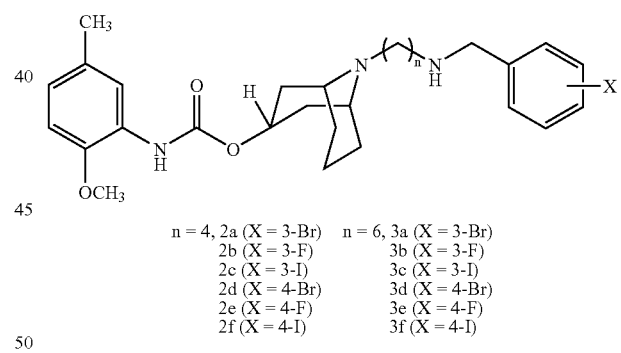

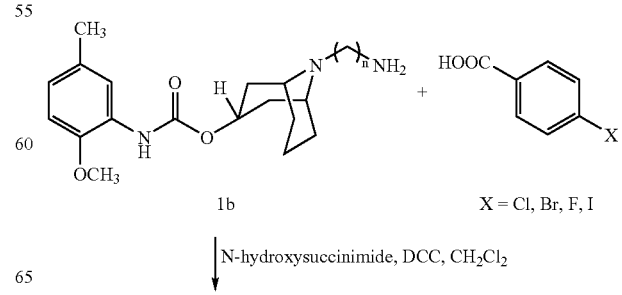

-continued
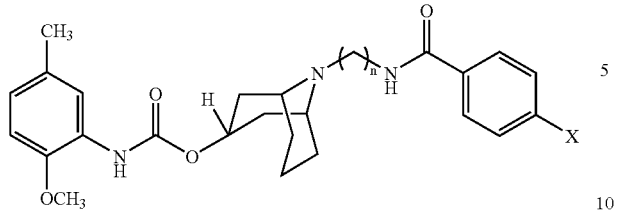
4a (X = Cl)
4b (X = Br)
4c (X = F)
4d (X = I)
Scheme 4
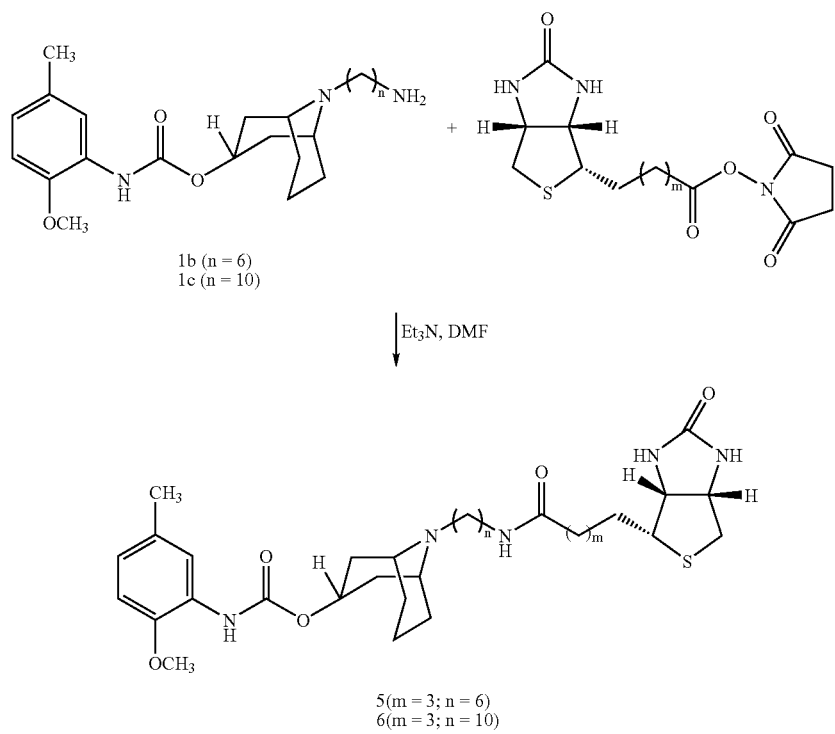
1b (n = 6)
1c (n = 10)
Et₃N, DMF
5 (m = 3; n = 6)
6 (m = 3; n = 10)
Scheme 5
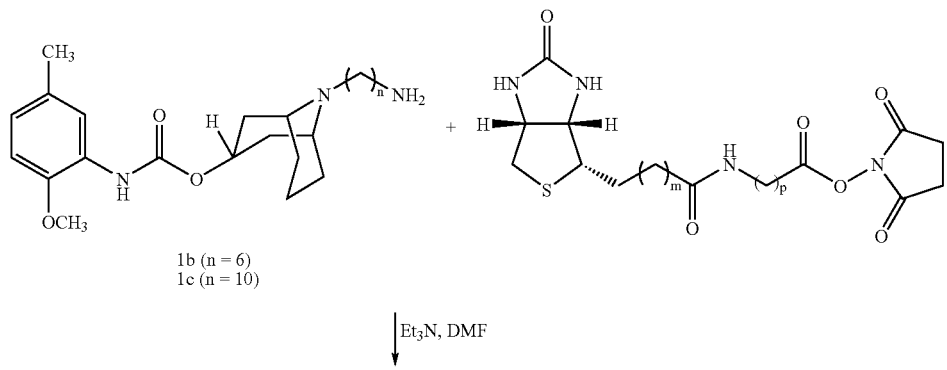
1b (n = 6)
1c (n = 10)
Et₃N, DMF -continued

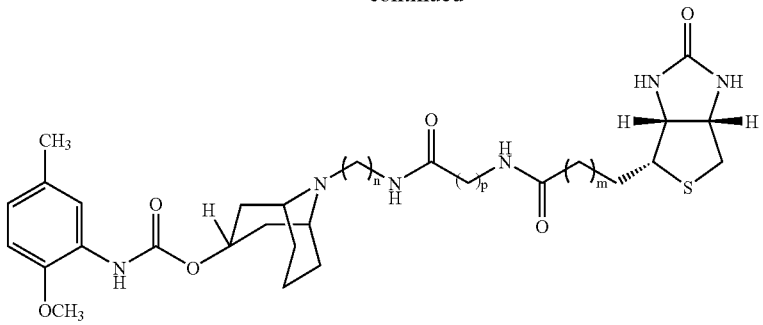

7 (m = 3; n = 6; p = 5)
8 (m = 3; n = 10; p = 5)

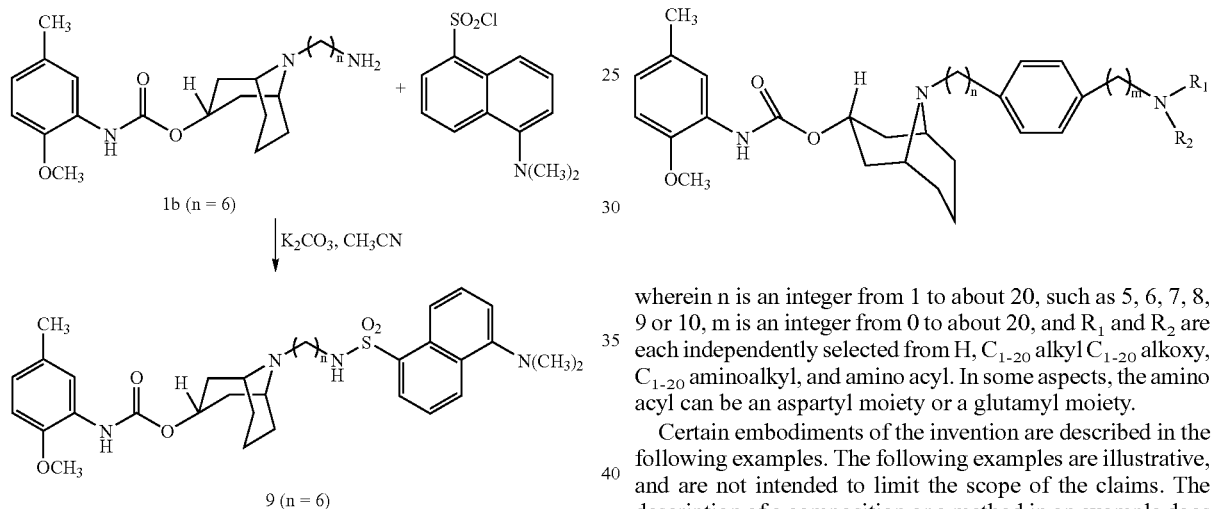

In some configurations, a σ2 receptor ligand can have the following structure wherein n is an integer from 1 to about 20, such as 5, 6, 7, 8, 9 or 10, and $R_1$ and $R_2$ are each independently selected from H, $C_{1-20}$ alkyl $C_{1-20}$ alkoxy, $C_{1-20}$ aminoalkyl, and amino acyl. In some aspects, the amino acyl can be aspartyl or glutamyl.

In some configurations, a σ2 receptor ligand can have the following structure:

wherein n is an integer from 1 to about 20, such as 5, 6, 7, 8, 9 or 10, m is an integer from 0 to about 20, and $R_1$ and $R_2$ are each independently selected from H, $C_{1-20}$ alkyl $C_{1-20}$ alkoxy, $C_{1-20}$ aminoalkyl, and amino acyl. In some aspects, the amino acyl can be an aspartyl moiety or a glutamyl moiety.

Certain embodiments of the invention are described in the following examples. The following examples are illustrative, and are not intended to limit the scope of the claims. The description of a composition or a method in an example does not imply that a described composition has (or has not) been produced, or that a described method has (or has not) been performed, irrespective of verb tense.

EXAMPLE 1

This example illustrates radioligand binding studies at sigma receptors.

In vitro binding studies were conducted in order to determine the affinity of the target compounds at σ1 and σ2 receptors. The σ1 binding studies were conducted using the σ1-selective radioligand, [$^3$H](+)-pentazocine in guinea pig brain membranes; σ2 sites were assayed in rat liver membranes with [$^3$H]DTG in the presence of (+)-pentazocine (1 μM) to mask σ1 sites or the σ2 selective ligand [$^3$H]RHM-1 alone.[6,21]

The results of the in vitro binding studies are shown in Table 1. For compounds 1a-c, the extension of the methylene linker separating the amino group and the bridgehead nitrogen atom (n=4, 6, and 10) had some affect on the binding affinity for sigma receptors. Compounds 1a and 1b, which have a linker group of 4 and 6 methylene units, respectively, between the amino group and the bridgehead nitrogen atom, both had moderate affinity and selectivity for σ2 versus σ1 receptors. Compound 1c with the 10 methylene spacer group had high affinity at σ2 receptor but low selectivity for σ2 versus σ1 receptor relative to 1a and 1b.

TABLE 1

In vitro binding data

| Compound | $K_i^a$ (nM) σ1[b] | σ2[c] | σ1/σ2 Ratio[d] |
|---|---|---|---|
| 1a | 2490 ± 271 | 12.94 ± 0.46 | 193 |
| 1b | 1418 ± 439 | 5.19 ± 0.80 | 273 |
| 1c | 134.3 ± 11.9 | 7.07 ± 1.27 | 19 |
| 2a | 66.29 ± 5.30 | 3.06 ± 0.41 | 21.66 |
| 2b | 0.30 ± 0.05 | 4.13 ± 0.33 | 0.07 |
| 2c | 63.87 ± 5.61 | 1.21 ± 0.14 | 52.77 |
| 2d | 1.70 ± 0.28 | 4.07 ± 0.61 | 0.42 |
| 2e | 22.15 ± 1.58 | 29.07 ± 3.48 | 0.76 |
| 2f | 0.34 ± 0.03 | 4.00 ± 0.54 | 0.08 |
| 3a | 112.40 ± 4.80 | 8.94 ± 0.61 | 12.57 |
| 3b | 0.46 ± 0.05 | 4.85 ± 0.49 | 0.09 |
| 3c | 0.56 ± 0.06 | 32.68 ± 5.93 | 0.02 |
| 3d | 43.16 ± 2.88 | 9.93 ± 1.61 | 4.35 |
| 3e | 1.00 ± 0.26 | 70.88 ± 4.38 | 0.01 |
| 3f | 0.65 ± 0.09 | 35.93 ± 1.50 | 0.02 |
| 4a | 1397 ± 64 | 3.56 ± 0.08 | 392 |
| 4b | 2041 ± 98 | 719 ± 84 | 2.84 |
| 4c | 1243 ± 212 | 497 ± 103 | 2.50 |
| 4d | 1412 ± 318 | 1,009 ± 110 | 1.40 |
| 5 | 3402 ± 538 | 114 ± 28 | 29.87 |
| 6 | 10,234 ± 2895 | 69.70 ± 7.67 | 147 |
| 7 | 10,365 ± 2313 | 1351 ± 78 | 7.67 |
| 8 | 3819 ± 518 | 733 ± 45 | 5.21 |
| 9 | 12,644 ± 3754 | 148 ± 8.85 | 85.43 |
| Haloperidol | 1.45 ± 0.33 | 24.20 ± 3.00 | 0.06 |
| SV119-1 | 1417 | 5.2 | 273 |
| WCII-26 | 5572 | 10.9 | 511 |
| RHM-I-138 | 544 | 12.3 | 44 |

[a]Mean ± SEM, Ki values were determined by at least three experiments.
[b]Ki for inhibiting the binding of [$^3$H](+)-pentazocine to guinea pig brain homogenates.
[c]Ki for inhibiting the binding of [$^3$H]DTG or [$^3$H]RHM-1 to rat liver homogenates.
[d]Ki for σ1/Ki for σ2.

Attachment of the substituted benzyl groups to the amino side chain of compounds 1a and 1b resulted in compounds (2a-f and 3a-f) having a dramatic increase in affinity at σ1 receptors. The affinity to σ2 receptors either slightly increased (2a-d and 2f vs 1a) or decreased relative to the primary amine (3a-f vs 1b). However, attachment of the substituted benzoyl groups to the amino side chain of compound 1b resulted in a dramatic reduction in affinity to σ2 receptors (compounds 4a-d). An exception to this was compound 4a, which had a high affinity and selectivity for σ2 receptors versus σ1 receptors.

Coupling of compounds 1b and 1c to two different biotin activated esters demonstrated that the biotinylated derivatives having a short chain (compounds 5 and 6) displayed a higher affinity and selectivity for σ2 versus σ1 receptor than the biotin analogs having the additional amidocaproate spacer group between the biotin and bridgehead nitrogen atom (compounds 7 and 8).

EXAMPLE 2

This example illustrates fluorescent compounds of the present teachings and their use in revealing subcellular localization of σ2 receptors in cells grown in vitro, using two-photon microscopy. In vitro binding studies demonstrate that the fluorescent analog, 9, prepared as outlined in Scheme 6, have a moderate affinity and selectivity for σ2 versus σ1 receptors. Excitation and emission spectra demonstrate that fluorescent analog 9 exhibits the maximum excitation wavelength at 333 nm, and the maximum emission wavelength with a range of 480-520 nm (FIG. 1).

Figure 3:
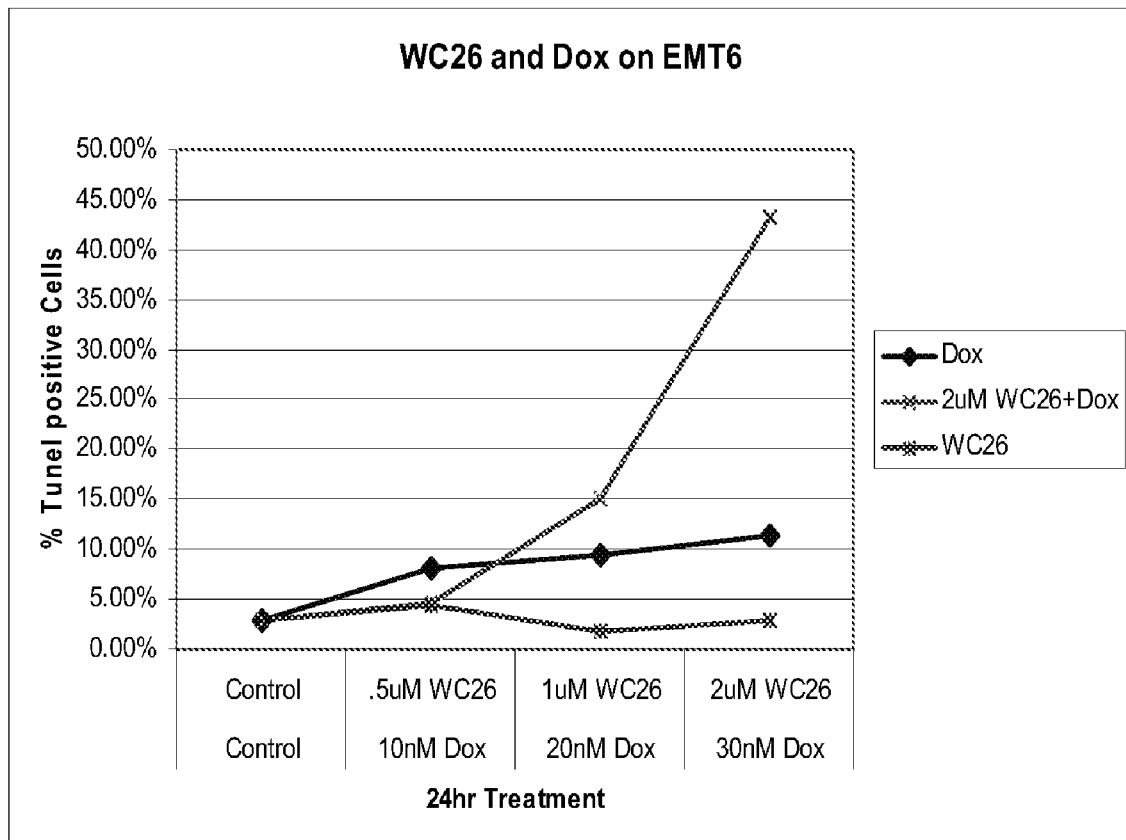
FIG. 3 illustrates increase in apoptosis, detected using a Tunel assay, in cells treated with Doxorubicin and WC-II-26.

In order to use two-photon microscopy to study the sub-cellular localization of σ2 receptors, EMT-6 cells were incubated with compound 9 at a concentration of 200 nM. The maximum excitation wavelength and maximum emission wavelength were examined by two-photon microscopy. The maximum excitation wavelength for two-photon microscopy was found to be 720 nm, whereas the maximum emission wavelength ranged from 480 to 540 nm. The results of the two-photon sub-cellular localization study are shown in FIG. 3. This figure illustrates that compound 9 reveals that σ2 receptors are localized to the cytoplasm in EMT-6 cells.

EXAMPLE 3

This example illustrates N-substituted-9-azabicyclo[3.3.1]nonan-3α-yl carbamate analogs having substituted benzyl groups attached to the primary amino group of compounds 1a and 1b.

In this study, the aromatic ring of the benzyl group was substituted with halogen atoms F, Br or I in the 3- or 4-position since the corresponding radiolabeled version (i.e. $^{18}$F-, $^{76}$Br- and $^{125}$I-labeled analogs) can be used in imaging studies to assess the σ2 receptor status of solid tumors. An unexpected finding was the dramatic increase in σ1 receptor affinity and reduction in σ1:σ2 selectivity ratio when making this substitution on the amino group of compounds 1a and 1b. This result was in stark contrast to that obtained when the amino group of 1b was substituted with a benzoyl group. This substitution led to a large reduction in σ2 receptor affinity and no change in σ1 receptor affinity (Table 1). An exception to this observation was the 5-chlorobenzoyl analog, 4a, which maintained a high affinity and selectivity for σ2 versus σ1 receptors.

EXAMPLE 4

This example illustrates chemical analysis of the compounds disclosed herein.

For these analyses, $^1$H NMR spectra were recorded on a Varian 300 MHz NMR spectrometer. Chemical slits are reported in δ values (parts per million, ppm) relative to an internal standard of tetramethylsilane (TMS). The following abbreviations are used for multiplicity of NMR signals: br s=broad singlet, d=doublet, m=multiplet, q=quintet, s=singlet, t=triplet. Melting points were determined with an electrothermal melting point apparatus and are uncorrected. Elemental analyses were performed by Atlantic Microlab, Inc., Norcross, Ga., and were within ±0.4% of the calculated values. Mass spectrometry was provided by the Washington University Mass Spectrometry Resource, an NIH Research Resource (Grant No. P41 RR0954). All reactions were carried out under an inert atmosphere of nitrogen. The general procedure for conversion to an HCl salt was the addition of excess ethereal HCl solution to a solution of the compound in dry ethanol. The solvent was evaporated and the resulting salt was triturated with anhydrous ether and dried in vacuo. The general procedure for conversion to an oxalate salt was the addition of a stoichiometric amount of a solution of oxalic acid in ethyl acetate to a solution of the compound in ethyl acetate. The solvent was evaporated and the resulting salt was triturated with anhydrous ether and dried in vacuo.

Elemental analyses

| Compound | % C Calcd | % C Found | % H Calcd | % H Found | % N Calcd | % N Found |
|---|---|---|---|---|---|---|
| 1a | 52.06 | 51.93 | 8.11 | 7.89 | 8.67 | 8.41 |
| 1b | 53.90 | 54.12 | 8.46 | 8.46 | 8.20 | 8.10 |
| 1c | 59.88 | 59.92 | 8.93 | 8.83 | 7.76 | 7.57 |
| 2a | 53.73 | 53.23 | 6.64 | 6.20 | 6.22 | 6.01 |
| 2b | 60.90 | 60.63 | 7.15 | 6.83 | 7.10 | 6.97 |
| 2c | 50.20 | 49.88 | 6.18 | 5.83 | 5.86 | 5.51 |
| 2d | 53.73 | 53.08 | 6.64 | 6.12 | 6.22 | 5.99 |
| 2e | 59.10 | 59.02 | 7.27 | 7.04 | 6.89 | 6.53 |
| 2f | 52.18 | 52.01 | 5.98 | 5.88 | 6.08 | 5.90 |
| 3a | 56.47 | 56.79 | 6.81 | 6.70 | 6.17 | 6.06 |
| 3b | 62.02 | 61.82 | 7.48 | 7.23 | 6.78 | 6.61 |
| 3c | 52.82 | 52.52 | 6.37 | 6.23 | 5.77 | 5.58 |
| 3d | 55.73 | 55.98 | 6.87 | 6.58 | 6.09 | 5.92 |
| 3e | 58.61 | 58.61 | 7.69 | 7.38 | 6.41 | 6.25 |
| 3f | 52.18 | 52.09 | 6.43 | 6.17 | 5.70 | 5.60 |
| 4a | 57.52 | 57.48 | 6.94 | 6.81 | 6.29 | 6.07 |
| 4b | 55.33 | 55.32 | 6.38 | 6.16 | 6.05 | 5.82 |
| 4c | 59.80 | 59.79 | 7.06 | 6.67 | 6.54 | 6.17 |
| 4d | 51.20 | 51.55 | 6.04 | 5.78 | 5.60 | 5.46 |
| 9 | 59.30 | 59.05 | 7.06 | 6.86 | 7.48 | 7.18 |

EXAMPLES 5-7

These examples illustrate general procedures for the synthesis of compounds 1a-c, and analytical data confirming their structures.

To synthesize these compounds, a mixture of secondary amine 10 (1.42 g, 4.68 mmol), N-(w-bromoalkyl)phthalimides (1 equiv), KI (1 equiv), and $K_2CO_3$ (5 equiv) in acetonitrile was stirred at reflux overnight. After filtration, volatile components were evaporated in vacuo. The resulting residue was purified by silica gel column chromatography (2% $CH_3OH$ in $CH_2Cl_2$) to give the intermediate products (11a-c), which were then refluxed with anhydrous hydrazine (1.2 equiv) in ethanol (30 mL) for 2 h. The solvent was evaporated and an aqueous solution of 10% NaOH (25 mL) was added. The mixture was extracted with $CH_2Cl_2$, dried over $Na_2SO_4$, and evaporated to give the target compounds. The products were converted to the corresponding hydrochloride salts for elemental analysis.

EXAMPLE 5

N-(9-(4-Aminobutyl)-9-azabicyclo[3.3.1]nonan-3α-yl)-N-(2-methoxy-5-methyl-phenyl)carbamate hydrochloride (1a)

This compound was obtained in 70% yield from N-(4-bromobutyl) phthalimide to give an off-white powder, mp 130-131° C. (dec); $^1$H NMR (free base, $CDCl_3$) δ 7.95 (br s, 1H), 7.14 (s, 1H), 6.72-6.79 (m, 2H), 5.13 (q, J=6.8 Hz, 1H), 3.84 (s, 3H), 3.05-3.10 (m, 2H), 2.68-2.72 (m, 2H), 2.57-2.61 (m, 2H), 2.39-2.49 (m, 2H), 2.29 (s, 3H), 2.09-2.19 (m, 1H), 1.83-1.91 (m, 2H), 1.19-1.54 (m, 11H); Anal. ($C_{21}H_{33}N_2O_3$.2HCl.2$H_2O$) C, H, N.

EXAMPLE 6

N-(9-(6-Aminohexyl)-9-azabicyclo[3.3.1]nonan-3α-yl)-N-(2-methoxy-5-methyl-phenyl)carbamate hydrochloride (1b)

This compound was obtained in 74% yield from N-(6-bromohexyl)phthalimide to give a white powder, mp 119-120° C. (dec); $^1$H NMR (free base, $CDCl_3$) δ 7.95 (br s, 1H), 7.14 (s, 1H), 6.73-6.80 (m, 2H), 5.14 (q, J=6.8 Hz, 1H), 3.85 (s, 3H), 3.05-3.10 (m, 2H), 2.66-2.71 (m, 2H), 2.55-2.60 (m, 2H), 2.40-2.50 (m, 2H), 2.30 (s, 3H), 2.08-2.24 (m, 1H), 1.82-1.94 (m, 2H), 1.20-1.55 (m, 14H); Anal. ($C_{23}H_{37}N_2O_3$.2HCl.2$H_2O$) C, H, N.

EXAMPLE 7

N-(9-(10-Aminodecyl)-9-azabicyclo[3.3.1]nonan-3α-yl)-N-(2-methoxy-5-methylphenyl)carbamate hydrochloride (1c)

This compound was obtained in 70% yield from N-(10-bromodecyl) phthalimide to give a white powder, mp 114-115° C. (dec); $^1$H NMR (free base, $CDCl_3$) δ 7.96 (br s, 1H), 7.14 (s, 1H), 6.72-6.78 (m, 2H), 5.14 (q, J=6.6 Hz, 1H), 3.85 (s, 3H), 3.04-3.09 (m, 2H), 2.65-2.70 (m, 2H), 2.53-2.58 (m, 2H), 2.39-2.49 (m, 2H), 2.30 (s, 3H), 2.09-2.20 (m, 1H), 1.81-1.93 (m, 2H), 1.19-1.53 (m, 23H); Anal. ($C_{27}H_{45}N_2O_3$.2HCl.0.5$H_2O$) C, H, N.

EXAMPLES 8-19

These examples illustrate general procedures for the synthesis of compounds 2a-f and 3a-f, and analytical data confirming their structures.

Primary amines 1a or 1b (200 mg) and 3-halo- or 4-halobenzaldehydes (1.3 equiv) in benzene (6 mL) were heated at 90° C. for 2 h. After evaporation, the resulting residue was treated with sodium borohydride (4 equiv) in ethanol (10 mL) at ambient temperature overnight. The reaction mixture was quenched with 10% HCl solution and concentrated in vacuo. The residue was dissolved in water (8 mL), the pH was adjusted to 10 by dropwise addition of an aqueous solution of 10% NaOH, and the product was extracted with $CH_2Cl_2$ (2×25 mL). The organic layer was dried over $Na_2SO_4$ and evaporated to give the products. The oxalate salts were made for elemental analysis.

EXAMPLE 8

N-(9-(4-(3'-Bromobenzylamino)butyl)-9-azabicyclo [3.3.1]nonan-3α-yl)-N-(2-methoxy-5-methylphenyl) carbamate oxalate (2a)

This compound was obtained in quantitative yield from 1a and 3-bromobenzaldehyde to give an off-white powder, mp 189-190° C. (dec); $^1$H NMR (free base, $CDCl_3$) δ 7.95 (br s, 1H), 7.13-7.50 (m, 5H), 6.72-6.80 (m, 2H), 5.12 (q, J=6.8 Hz, 1H), 3.84 (s, 3H), 3.76 (s, 2H), 3.04-3.08 (m, 2H), 2.57-2.64 (m, 4H), 2.38-2.49 (m, 2H), 2.29 (s, 3H), 2.09-2.24 (m, 1H), 1.81-1.91 (m, 2H), 1.47-1.56 (m, 8H), 1.19-1.25 (m, 2H); Anal. ($C_{28}H_{38}BrN_3O_3.C_2H_2O_4$.2$H_2O$) C, H, N.

EXAMPLE 9

N-(9-(4-(3'-Fluorobenzylamino)butyl)-9-azabicyclo [3.3.1]nonan-3α-yl)-N-(2-methoxy-5-methylphenyl) carbamate oxalate (2b)

This compound was obtained in 55% yield from 1a and 3-fluorobenzaldehyde to give a white powder, mp 185-186° C. (dec); $^1$H NMR (free base, $CDCl_3$) δ 7.95 (br s, 1H), 6.72-7.31 (m, 7H), 5.12 (q, J=6.7 Hz, 1H), 3.84 (s, 3H), 3.79 (s, 2H), 3.04-3.08 (m, 2H), 2.57-2.65 (m, 4H), 2.38-2.48 (m, 2H), 2.29 (s, 3H), 2.08-2.22 (m, 1H), 1.80-1.94 (m, 2H), 1.47-1.68 (m, 8H), 1.18-1.24 (m, 2H); Anal. ($C_{28}H_{38}FN_3O_3 \cdot C_2H_2OO_4 \cdot H_2O$) C, H, N.

EXAMPLE 10

N-(9-(4-(3'-Iodobenzylamino)butyl)-9-azabicyclo-[3.3.1]nonan-3α-yl)-N-(2-methoxy-5-methylphenyl) carbamate oxalate (2c)

This compound was obtained in 12% yield from 1a and 3-iodobenzaldehyde to give a white powder, mp 200-201° C. (dec); $^1$H NMR (free base, CDCl$_3$) δ 7.94 (br s, 1H), 7.70 (s, 1H), 7.55-7.60 (m, 1H), 7.30-7.34 (m, 1H), 7.03-7.13 (m, 2H), 6.72-6.80 (m, 2H), 5.12 (q, J=6.7 Hz, 1H), 3.84 (s, 3H), 3.74 (s, 2H), 3.06-3.10 (m, 2H), 2.59-2.65 (m, 4H), 2.39-2.49 (m, 2H), 2.29 (s, 3H), 2.14-2.24 (m, 1H), 1.80-1.90 (m, 2H), 1.46-1.56 (m, 8H), 1.20-1.26 (m, 2H); Anal. ($C_{28}H_{38}IN_3O_3 \cdot C_2H_2OO_4 \cdot 2H_2O$) C, H, N.

EXAMPLE 11

N-(9-(4-(4'-Bromobenzylamino)butyl)-9-azabicyclo[3.3.1]nonan-3α-yl)-N-(2-methoxy-5-methylphenyl) carbamates (2d)

This compound was obtained in quantitative yield from 1a and 4-bromobenzaldehyde to give an off-white powder, mp 197-198° C. (dec); $^1$H NMR (free base, CDCl$_3$) δ 7.95 (br s, 1H), 7.44 (d, J=8.3 Hz, 2H), 7.21 (d, J=8.3 Hz, 2H), 7.13 (s, 1H), 6.73-6.80 (m, 2H), 5.12 (q, J=6.8 Hz, 1H), 3.84 (s, 3H), 3.74 (s, 2H), 3.02-3.08 (m, 2H), 2.54-2.64 (m, 2H), 2.37-2.47 (m, 2H), 2.30 (s, 3H), 2.07-2.22 (m, 1H), 1.78-1.92 (m, 2H), 1.16-1.54 (m, 10H); Anal. ($C_{28}H_{38}BrN_3O_3 \cdot C_2H_2OO_4 \cdot 2H_2O$) C, H, N.

EXAMPLE 12

N-(9-(4-(4'-Fluorobenzylamino)butyl)-9-azabicyclo[3.3.1]nonan-3α-yl)-N-(2-methoxy-5-methylphenyl) carbamate oxalate (2e)

This compound was obtained in quantitative yield from 1a and 4-fluorobenzaldehyde to give a white powder, mp 195-196° C. (dec); $^1$H NMR (free, base, CDCl$_3$) δ 7.95 (br s, 1H), 7.29-7.34 (m, 2H), 7.13 (s, 1H), 6.97-7.07 (m, 2H), 6.73-6.80 (m, 2H), 5.12 (q, J=6.8 Hz, 1H), 3.84 (s, 3H), 3.76 (s, 2H), 3.04-3.08 (m, 2H), 2.56-2.65 (m, 2H), 2.38-2.48 (m, 2H), 2.29 (s, 3H), 2.09-2.19 (m, 1H), 1.79-1.90 (m, 2H), 1.19-1.56 (m, 9H); Anal. ($C_{28}H_{38}FN_3O_3 \cdot C_2H_2OO_4 \cdot 2H_2O$) C, H, N.

EXAMPLE 13

N-(9-(4-(4'-Iodobenzylamino)butyl)-9-azabicyclo[3.3.1]nonan-3α-yl)-N-(2-methoxy-5-methylphenyl) carbamate oxalate (2f)

This compound was obtained in 10% yield from 1a and 4-iodobenzaldehyde to give a white powder, mp 159-160° C. (dec); $^1$H NMR (free base, CDCl$_3$) δ 7.95 (br s, 1H), 7.64 (d, J=8.1 Hz, 2H), 7.14 (s, 1H), 7.10 (d, J=8.1 Hz, 2H), 6.72-6.80 (m, 2H), 5.12 (q, J=6.7 Hz, 1H), 3.84 (s, 3H), 3.74 (s, 2H), 3.04-3.10 (m, 2H), 2.57-2.64 (m, 4H), 2.38-2.49 (m, 2H), 2.30 (s, 3H), 2.10-2.20 (m, 1H), 1.80-1.92 (m, 2H), 1.18-1.58 (m, 10H); Anal. ($C_{28}H_{38}IN_3O_3 \cdot C_2H_2OO_4 \cdot 0.5H_2O$) C, H, N.

EXAMPLE 14

N-(9-(6-(3'-Bromobenzylamino)hexyl)-9-azabicyclo[3.3.1]nonan-3α-yl)-N-(2-methoxy-5-methylphenyl) carbamate oxalate (3a)

This compound was obtained in 88% yield from 1b and 3-bromobenzaldehyde to give a white powder, mp 193-194° C. (dec); $^1$H NMR (free base, CDCl$_3$) δ 7.95 (br s, 1H), 7.49 (s, 1H), 7.37 (d, J=7.9 Hz, 1H), 7.22 (d, J=7.9 Hz, 1H), 7.18 (t, J=7.9 Hz, 1H), 7.14 (s, 1H), 6.73-6.80 (m, 2H), 5.13 (q, J=6.7 Hz, 1H), 3.84 (s, 3H), 3.76 (s, 2H), 3.04-3.09 (m, 2H), 2.55-2.64 (m, 4H), 2.40-2.50 (m, 2H), 2.29 (s, 3H), 2.10-2.22 (m, 1H), 1.84-1.93 (m, 2H), 1.20-1.52 (m, 14H); Anal. ($C_{30}H_{42}BrN_3O_3 \cdot C_2H_2OO_4 \cdot H_2O$) C, H, N.

EXAMPLE 15

N-(9-(6-(3'-Fluorobenzylamino)hexyl)-9-azabicyclo[3.3.1]nonan-3α-yl)-N-(2-methoxy-5-methylphenyl) carbamate oxalate (3b)

This compound was obtained in 86% yield from 1b and 3-fluorobenzaldehyde to give a white powder, mp 149-150° C. (dec); $^1$H NMR (CDCl$_3$) δ 7.95 (br s, 1H), 7.24-7.29 (m, 1H), 7.13 (s, 1H), 7.04-7.10 (m, 2H), 6.90-6.96 (m, 1H), 6.73-6.80 (m, 2H), 5.13 (q, J=6.5 Hz, 1H), 3.85 (s, 3H), 3.79 (s, 2H), 3.00-3.05 (m, 2H), 2.54-2.64 (m, 4H), 2.39-2.49 (m, 2H), 2.29 (s, 3H), 2.09-2.18 (m, 1H), 1.83-1.93 (m, 2H), 1.19-1.55 (m, 14H); Anal. ($C_{30}H_{42}FN_3O_3 \cdot C_2H_2OO_4 \cdot H_2O$) C, H, N.

EXAMPLE 16

N-(9-(6-(3'-Iodobenzylamino)hexyl)-9-azabicyclo-[3.3.1]nonan-3α-yl)-N-(2-methoxy-5-methylphenyl) carbamate oxalate (3c)

This compound was obtained in 86% yield from 1b and 3-iodobenzaldehyde to give a white powder, mp 192-193° C. (dec); $^1$H NMR (CDCl$_3$) δ 7.95 (br s, 1H), 7.69 (s, 1H), 7.57 (d, J=7.8 Hz, 1H), 7.28 (d, J=7.8 Hz, 1H), 7.13 (s, 1H), 7.05 (t, J=7.8 Hz, 1H), 6.72-6.79 (m, 2H), 5.13 (q, J=6.6 Hz, 1H), 3.84 (s, 3H), 3.73 (s, 2H), 3.04-3.09 (m, 2H), 2.54-2.63 (m, 4H), 2.39-2.49 (m, 2H), 2.29 (s, 3H), 2.08-2.18 (m, 1H), 1.82-1.94 (m, 2H), 1.19-1.54 (m, 14H); Anal. ($C_{30}H_{42}IN_3O_3 \cdot C_2H_2OO_4 \cdot H_2O$) C, H, N.

EXAMPLE 17

N-(9-(6-(4'-Bromobenzylamino)hexyl)-9-azabicyclo[3.3.1]nonan-3α-yl)-N-(2-methoxy-5-methylphenyl) carbamate oxalate (3d)

This compound was obtained in 85% yield from 1b and 4-bromobenzaldehyde to give a white powder, mp 164-165° C. (dec); $^1$H NMR (CDCl$_3$) δ 7.95 (br s, 1H), 7.44 (d, J=8.1 Hz, 2H), 7.20 (d, J=8.1 Hz, 2H), 7.14 (s, 1H), 6.73-6.80 (m, 2H), 5.13 (q, J=6.8 Hz, 1H), 3.85 (s, 3H), 3.74 (s, 2H), 3.04-3.08 (m, 2H), 2.54-2.62 (m, 4H), 2.40-2.50 (m, 2H), 2.29 (s, 3H), 2.10-2.23 (m, 1H), 1.83-1.92 (m, 2H), 1.19-1.51 (m, 14H); Anal. ($C_{30}H_{42}BrN_3O_3 \cdot C_2H_2OO_4 \cdot 1.5H_2O$) C, H, N.

EXAMPLE 18

N-(9-(6-(4'-Fluorobenzylamino)hexyl)-9-azabicyclo[3.3.1]nonan-3α-yl)-N-(2-methoxy-5-methylphenyl)carbamate oxalate (3e)

This compound was obtained in 92% yield from 1b and 4-fluorobenzaldehyde to give a white powder, mp 178-179° C. (dec); $^1$H NMR (CDCl$_3$) δ 7.95 (br s, 1H), 7.28-7.36 (m, 2H), 7.14 (s, 1H), 6.97-7.07 (m, 2H), 6.73-6.79 (m, 2H), 5.13 (q, J=6.8 Hz, 1H), 3.84 (s, 3H), 3.75 (s, 2H), 3.03-3.08 (m, 2H), 2.58-2.63 (m, 2H), 2.38-2.48 (m, 2H), 2.29 (s, 3H), 2.05-2.20 (m, 1H), 1.80-1.92 (m, 2H), 1.18-1.53 (m, 13H); Anal. ($C_{30}H_{42}FN_3O_3 \cdot C_2H_2OO_4 \cdot 3H_2O$) C, H, N.

EXAMPLE 19

N-(9-(6-(4'-Iodobenzylamino)hexyl)-9-azabicyclo[3.3.1]nonan-3α-yl)-N-(2-methoxy-5-methylphenyl)carbamate oxalate (3f)

This compound was obtained in 85% yield from 1b and 4-iodobenzaldehyde to give a white powder, mp 144-145° C. (dec); $^1$H NMR (CDCl$_3$) δ 7.95 (br s, 1H), 7.44 (d, J=8.1 Hz, 2H), 7.20 (d, J=8.1 Hz, 2H), 7.14 (s, 1H), 6.73-6.80 (m, 2H), 5.13 (q, J=6.8 Hz, 1H), 3.85 (s, 3H), 3.74 (s, 2H), 3.04-3.08 (m, 2H), 2.54-2.62 (m, 4H), 2.40-2.50 (m, 2H), 2.29 (s, 3H), 2.10-2.23 (m, 1H), 1.83-1.92 (m, 2H), 1.19-1.51 (m, 14H); Anal. ($C_{30}H_{42}IN_3O_3 \cdot C_2H_2OO_4 \cdot 1.5H_2O$) C, H, N.

EXAMPLES 20-23

These examples illustrate general procedures for the synthesis of compounds 4a-d, and analytical data confirming their structures.

A solution of 1,3-dicyclohexylcarbodiimide (154 mg, 0.74 mmol) in CH$_2$Cl$_2$ (0.5 mL) was added dropwise to a solution of 4-halobenzoic acids (1.2 equiv) and N-hydroxysuccinimide (64 mg, 0.74 mmol) in CH$_2$Cl$_2$ (2 mL) at 0° C. (ice bath). After removal of the ice bath, the mixture was stirred at ambient temperature for 1 h. A solution of amine 1b (250 mg, 0.62 mmol) in CH$_2$Cl$_2$ (5 mL) was slowly added, and the reaction mixture was stirred at ambient temperature for 3 h. The formed precipitate was filtered, the organic layer was washed with water (1×50 mL) and then saturated aqueous K$_2$CO$_3$ (1×50 mL). The organic layer was dried over Na$_2$SO$_4$ and concentrated in vacuo. The resulting residue was purified by silica gel column chromatography (5% CH$_3$OH in CH$_2$Cl$_2$) to yield the compounds. The oxalate salts were made for elemental analysis.

EXAMPLE 20

N-(9-(4-(4'-Chlorobenzoylamino)hexyl)-9-azabicyclo[3.3.1]nonan-3α-yl)-N-(2-methoxy-5-methylphenyl)carbamate oxalate (4a)

This compound was obtained in 58% yield from 4-chlorobenzoic acid to give a white powder, mp 127-128° C. (dec); $^1$H NMR (free base, CDCl$_3$) δ 7.92 (br s, 1H), 7.72 (d, J=8.8 Hz, 2H), 7.37 (d, J=8.8 Hz, 2H), 7.14 (s, 1H), 6.73-6.80 (m, 2H), 6.29 (br s, 1H), 5.14 (q, J=6.8 Hz, 1H), 3.85 (s, 3H), 3.42-3.48 (m, 2H), 3.05-3.08 (m, 2H), 2.38-2.60 (m, 4H), 2.26 (s, 3H), 1.16-2.11 (m, 16H); Anal. ($C_{30}H_{40}ClN_3OO_4 \cdot C_2H_2O_4 \cdot 2H_2O$) C, H, N.

EXAMPLE 21

N-(9-(4-(4'-Bromobenzoylamino)hexyl)-9-azabicyclo[3.3.1]nonan-3α-yl)-N-(2-methoxy-5-methylphenyl)carbamate oxalate (4b)

This compound was obtained in 71% yield from 4-bromobenzoic acid to give a white powder, mp 152-153° C. (dec); $^1$H NMR (free base, CDCl$_3$) δ 7.91 (br s, 1H), 7.67 (d, J=8.4 Hz, 2H), 7.53 (d, J=8.4 Hz, 2H), 7.14 (s, 1H), 6.73-6.80 (m, 2H), 6.39 (br s, 1H), 5.14 (q, J=6.8 Hz, 1H), 3.85 (s, 3H), 3.42-3.48 (m, 2H), 3.10-3.15 (m, 2H), 2.49-2.66 (m, 4H), 2.27 (s, 3H), 1.22-2.22 (m, 16H); Anal. ($C_{30}H_{40}BrN_3O_4 \cdot C_2H_2O_4 \cdot H_2O$) C, H, N.

EXAMPLE 22

N-(9-(4-(4'-Fluorobenzoylamino)hexyl)-9-azabicyclo[3.3.1]nonan-3α-yl)-N-(2-methoxy-5-methylphenyl)carbamate oxalate (4c)

This compound was obtained in 81% yield from 4-fluorobenzoic acid to give a white powder, mp 119-120° C. (dec); $^1$H NMR (free base, CDCl$_3$) δ 7.91 (br s, 1H), 7.79-7.84 (m, 2H), 6.97-7.05 (m, 3H), 6.73-6.78 (m, 2H), 6.40 (br s, 1H), 5.14 (q, J=6.5 Hz, 1H), 3.85 (s, 3H), 3.41-3.47 (m, 2H), 3.18-3.22 (m, 2H), 2.53-2.74 (m, 4H), 2.27 (s, 3H), 1.28-2.17 (m, 16H); Anal. ($C_{30}H_{40}FN_3OO_4 \cdot C_2H_2OO_4 \cdot 1.5H_2O$) C, H, N.

EXAMPLE 23

N-(9-(4-(40-Iodobenzoylamino)hexyl)-9-azabicyclo[3.3.1]nonan-3α-yl)-N-(2-methoxy-5-methylphenyl)carbamate oxalate (4d)

This compound was obtained in 57% yield from 4-iodobenzoic acid to give a white powder, mp 150-151° C. (dec); $^1$H NMR (free base, CDCl$_3$) δ 7.91 (br s, 1H), 7.74 (d, J=8.6 Hz, 2H), 7.52 (d, J=8.6 Hz, 2H), 7.13 (s, 1H), 6.73-6.77 (m, 2H), 6.38 (br s, 1H), 5.13 (q, J=6.8 Hz, 1H), 3.84 (s, 3H), 3.40-3.48 (m, 2H), 3.08-3.14 (m, 2H), 2.44-2.64 (m, 4H), 2.26 (s, 3H), 1.20-2.20 (m, 16H); Anal. ($C_{30}H_{40}IN_3OO_4 \cdot C_2H_2O_4 \cdot 1.5H_2O$) C, H, N.

EXAMPLES 24-25

These examples illustrate general procedures for the synthesis of compounds 5 and 6, and analytical data confirming their structures. Primary amines 1b or 1c (150 mg), (+)-biotin N-hydroxysuccinimide ester (1.1 equiv), and triethylamine (0.1 mL) in DMF (5 mL) were stirred at 65° C. for 48 h. The mixture was allowed to cool to ambient temperature, and volatiles were removed under reduced pressure. The resulting residue was purified by silica gel column chromatography (15% CH$_3$OH, 1% NH$_4$OH in CH$_2$Cl$_2$) to give compound 5 or compound 6.

EXAMPLE 24

Compound 5

This compound was obtained in 76% yield from 1b to give a white powder; $^1$H NMR (DMSO-d6) δ 8.12 (br s, 1H), 7.70-7.74 (m, 1H), 7.47 (s, 1H), 6.82-6.89 (m, 2H), 6.41 (s, 1H), 6.35 (s, 1H), 4.90-4.99 (m, 1H), 4.27-4.31 (m, 1H), 4.09-4.13 (m, 1H), 3.75 (s, 3H), 2.30-3.11 (m, 13H), 2.21 (s, 3H), 1.13-2.06 (m, 22H); MS (FAB$^+$) exact mass calculated for $C_{33}H_{51}N_5O_5S$ [M+Li]$^+$: 636.3771, found: 636.3762.

EXAMPLE 25

Compound 6

This compound was obtained in 78% yield from 1c to give a white powder; $^1$H NMR (DMSO-d6) δ 8.07 (br s, 1H), 7.70-7.74 (m, 1H), 7.49 (s, 1H), 6.82-6.90 (m, 2H), 6.42 (s, 1H), 6.35 (s, 1H), 4.90-4.98 (m, 1H), 4.28-4.31 (m, 1H), 4.10-4.15 (m, 1H), 3.75 (s, 3H), 2.30-3.09 (m, 13H), 2.21 (s, 3H), 1.11-2.05 (m, 30H); MS (FAB$^+$) exact mass calculated for $C_{37}H_{59}N_5O_5S$ [M+Li]$^+$: 692.4397, found: 692.4411.

EXAMPLES 26-27

These examples illustrate general procedures for the synthesis of compounds 7 and 8, and analytical data confirming their structures.

Primary amines 1b or 1c (150 mg), (+)-biotinamidocaproate N-hydroxysuccinimide ester (1.1 equiv), and triethylamine (0.1 mL) in DMF (5 mL) were stirred at 50° C. for 48 h. The mixture was allowed to cool to ambient temperature, and volatiles were removed under reduced pressure. The resulting residue was purified by silica gel column chromatography (15% CH$_3$OH, 1% NH$_4$OH in CH$_2$Cl$_2$) to yield compound 7 or 8.

EXAMPLE 26

Compound 7

This compound was obtained in 88% yield from 1b to give a white solid; $^1$H NMR (DMSO-d6) δ 8.11 (br s, 1H), 7.70-7.75 (m, 2H), 7.48 (s, 1H), 6.82-6.90 (m, 2H), 6.42 (s, 1H), 6.36 (s, 1H), 4.92-4.99 (m, 1H), 4.25-4.32 (m, 1H), 4.08-4.15 (m, 1H), 3.76 (s, 3H), 2.30-3.10 (m, 15H), 2.22 (s, 3H), 1.10-2.10 (m, 30H); MS (FAB$^+$) exact mass calculated for $C_{39}H_{62}N_6O_6S$ [M+Li]$^+$: 749.4612, found: 749.4628.

EXAMPLE 27

Compound 8

This compound was obtained in 95% yield from 1c to give an off-white solid; $^1$H NMR (DMSO-d6) δ 8.02 (s, 2H), 7.94 (br s, 1H), 7.14 (s, 1H), 6.73-6.80 (m, 2H), 6.26 (s, 1H), 6.14 (s, 1H), 5.09-5.18 (m, 1H), 4.49-4.54 (m, 1H), 4.30-4.34 (m, 1H), 3.85 (s, 3H), 2.40-3.30 (m, 11H), 2.29 (s, 3H), 1.21-2.23 (m, 42H); MS (FAB$^+$) exact mass calculated for $C_{43}H_{70}N_6O_6S$ [M+Li]$^+$: 805.5238, found: 805.5243.

EXAMPLE 28

This example illustrates a general procedure for the synthesis of N-(9-(6-(5-Dimethylamino-1-naphthalenesulfonamido))hexyl)-9-azabicyclo[3.3.1]-nonan-3α-yl-N-(2-methoxy-5-methylphenyl)carbamate oxalate (9), and analytical data confirming its structure. A solution of dansyl chloride (135 mg, 0.50 mmol) in CH$_3$CN (6 mL) was added dropwise to a mixture of 1b (200 mg, 0.50 mmol) and K$_2$CO$_3$ (104 mg, 0.75 mmol) in CH$_3$CN (2 mL). The reaction mixture was stirred at ambient temperature for 24 h. The mixture was filtered, and volatiles were removed in vacuo. The product was purified by column chromatography (CH$_3$OH—CH$_2$Cl$_2$—NH$_4$OH 10:90:0.1) to give compound 9 (93%) as a yellow oil. The oxalate salt was made for analysis, mp 162-163° C.; $^1$HNMR (free base, CDCl$_3$) δ 8.54 (d, J=8.6 Hz, 1H), 8.30 (d, J=8.6 Hz, 1H), 8.23-8.26 (m, 1H), 7.94 (br s, 1H), 7.50-7.58 (m, 2H), 7.18 (d, J=7.1 Hz, 1H), 7.13 (s, 1H), 6.73-6.80 (m, 2H), 5.10 (q, J=6.7 Hz, 1H), 4.77 (br s, 1H), 2.99-3.11 (m, 2H), 2.89 (s, 6H), 2.42-2.56 (m, 4H), 2.29 (s, 3H), 1.17-2.15 (m, 18H); MS (FAB$^+$) exact mass calculated for $C_{35}H_{48}N_4O_5S$ [M+Li]$^+$: 643.3505, found: 643.3490; Anal. ($C_{35}H_{48}N_4O_5S \cdot C_2H_2OO_4 \cdot 1.25H_2O$) C, H, N.

EXAMPLE 29

This example illustrates sigma receptor binding assays.

In this example, test compounds were dissolved in N,N-dimethylformamide (DMF), dimethylsulfoxide (DMSO) or ethanol and then diluted in 50 mM Tris-HCl, pH 7.4 buffer containing 150 mM NaCl and 100 mM EDTA. Membrane homogenates were made from guinea pig brain for σ1 binding assays and rat liver for σ2 binding assays. Membrane homogenates were diluted with 50 mM Tris-HCl buffer, pH 8.0, and incubated at 25° C. in a total volume of 150 µL in 96-well plates with the radioligand and test compounds with concentrations ranging from 0.1 nM to 10 µM. After incubation was completed, the reactions were terminated by the addition of 150 µL of ice-cold wash buffer (10 mM Tris-HCl, 150 mM NaCl, pH 7.4) using a 96-channel transfer pipette (Fisher Scientific, Pittsburgh, Pa.), and the samples harvested and filtered rapidly through 96-well fiberglass filter plate (Millipore, Billerica, Mass.) that had been presoaked with 100 µL of 50 mM Tris-HCl buffer, pH 8.0, for 1 h. Each filter was washed three times with 200 µL of ice cold wash buffer. A Wallac 1450 MicroBeta liquid scintillation counter (Perkin-Elmer, Boston, Mass.) was used to quantify the bound radioactivity. The σ1 receptor binding assay was conducted using guinea pig brain membrane homogenates (~300 µg protein) and ~5 nM [$^3$H](+)-pentazocine (34.9 Ci/mmol, Perkin-Elmer, Boston, Mass.), incubation time was 90 min. Nonspecific binding was determined from samples that contained 10 µM of cold haloperidol.

The σ2 receptor binding assays were conducted using rat liver membrane homogenates (~300 µg protein) and ~1 nM [$^3$H]RHM-1 (80 Ci/mmol, American Radiolabeled Chemicals Inc., St. Louis, Mo.) alone or ~5 nM [$^3$H]DTG (58.1 Ci/mmol, Perkin-Elmer, Boston, Mass.) in the presence of 1 µM (+)-pentazocine to block σ1 sites. The incubation time was 60 min for [$^3$H]RHM-1 and 120 min for [$^3$H]DTG. Nonspecific binding was determined from samples that contained 10 µM of cold haloperidol.

Data from the competitive inhibition experiments were modeled using nonlinear regression analysis to determine the concentration of inhibitor that inhibits 50% of the specific binding of the radioligand (IC50 value). Competitive curves were best fit to a one-site fit and gave pseudo-Hill coefficients of 0.6-1.0. $K_i$ values were calculated using the method of Cheng and Prusoff[20] and represent mean values ±SEM. The Kd value used for [$^3$H](+)-pentazocine in guinea pig brain was 7.89 nM, for [$^3$H]DTG in rat liver was 30.73 nM, and for [$^3$H]RHM-1 in rat liver was 0.66 nM

EXAMPLE 30

This example illustrates the fluorescent σ2 ligand assay.

In this example, the mono-dansyl analog, compound 9, was dissolved in methanol, and excitation and emission spectra were determined. Fluorescent excitation and emission spectra were recorded on a spectrofluorometer (Perkin-Elmer LS 50, Wellesley, Mass.). Excitation spectra and emission spectra for compound 9 were also determined using a Zeiss two-photon microscope (LSM 510 NLO META). EMT-6 cells were incubated with compound 9 (200 nM). To determine the maximum wavelength of excitation, cells were illuminated with wavelengths ranging from 720 nm to 860 nm at 10 nm intervals. Emission spectra were collected using a 685 nm-short pass filter. To determine the maximum emission wavelength, the excitation wavelength was set to 720 nm and emission spectra were collected using a series of filters with 10 nm bandwidth at wavelengths ranging from 457 nm to 596 nm. The emission spectra were obtained at 11 nm intervals to give images with a resolution of 512×512 pixels.

EXAMPLE 31

Figure 2:
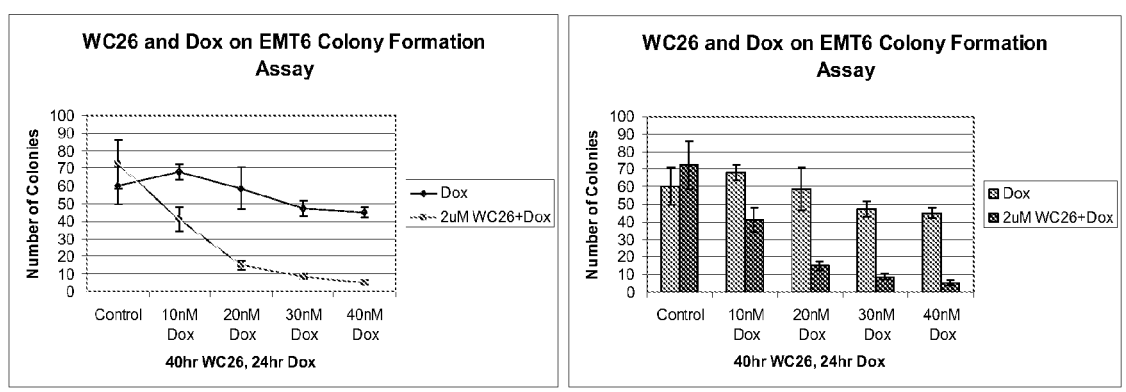
FIG. 2 illustrates colony formation on Doxorubicin-treated EMT-6 cells in the presence or absence of 2 μM WC-II-26.
Figure 5:
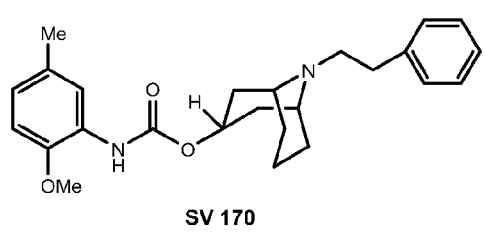
FIG. 5 illustrates structures of some σ2 selective ligands.
Figure 5:
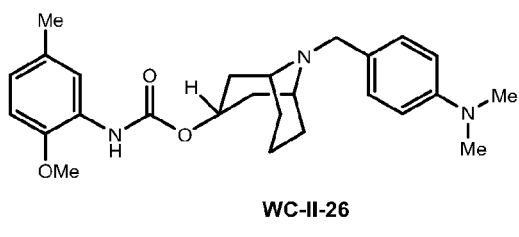
Figure 5:
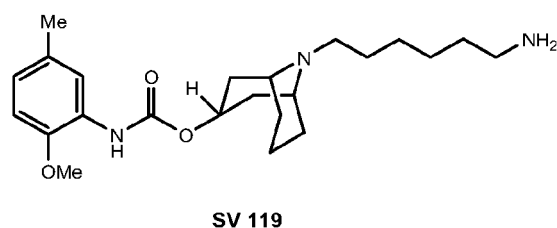
Figure 5:
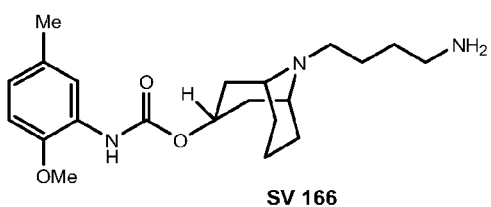
Figure 5:
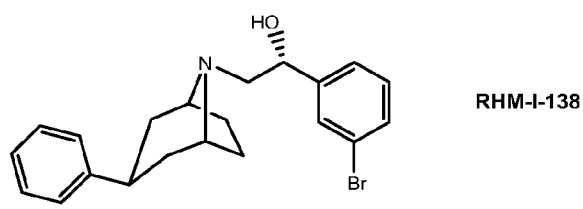
Figure 6:
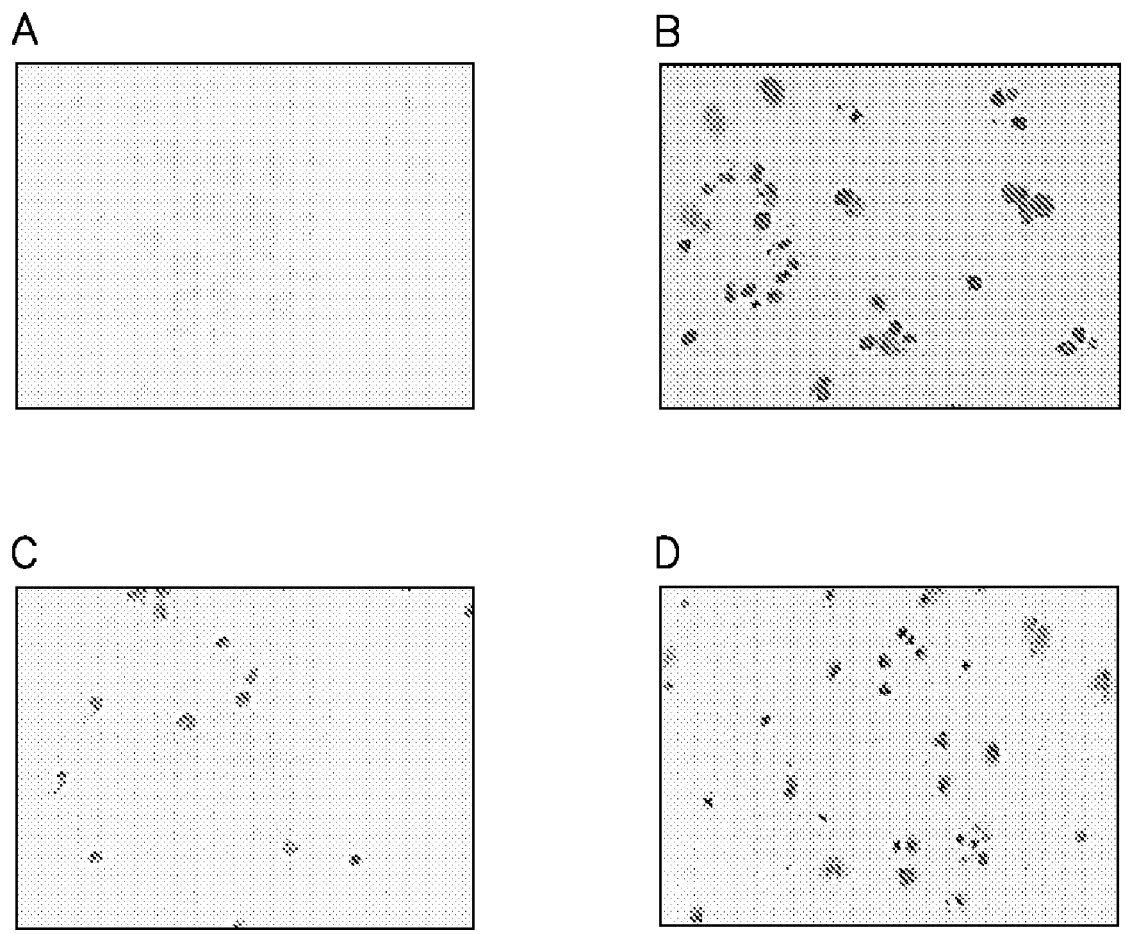
FIG. 6 illustrates nuclear fragmentation in EMT-6 cells treated with σ2 selective ligands. DNA fragmentation was detected by TUNEL staining and fluorescence microscopy. A: Untreated cells. B: Cell treated for 48 h with WC-II-26 (40 μM). C: Cells treated for 16 h with SV119 (100 μM). D: Cells treated for 16 h with RHM-I-138 (40 μM).

This Example illustrates colony formation assay on Doxorubicin ("Dox")-treated EMT-6 cells in the presence or absence of 2 μM WC-II-26. The structures of the sigma ligands used in this and subsequent examples are illustrated in FIG. 5 and FIG. 6. In these experiments, the number of colonies formed at 2 μM WC-II-26, 10, 20, and 30 nM of Dox alone were not changed significantly compare to control cells. Only the highest concentration of Dox (40 nM) resulted in a decrease in colony forming efficiency (decreased about 25%). When 2 μM WC-II-26 was combined with the same concentrations of Dox, the ability of survival were significantly reduced (38%, 77%, 86% and 92% of control). These data, as shown in FIG. 2, indicate that WC-II-26 sensitizes breast tumor cells to cytotoxic effects of Doxorubicin.

EXAMPLE 32

This example illustrates enhancement of apoptosis.

In these experiments, a Tunel assay was used to detect apoptotic cells with damaged DNA strands. As shown in FIG. 3, EMT-6 cells treated with compound WC-II-26 at low concentration such as 2 μM, showed less than 5% Tunel-positive cells. Furthermore, EMT-6 cells treated with Dox at 30 nM yielded only 10% Tunel-positive cells. However, when EMT-6 cells were treated with 2 μM WC-II-26 plus 30 nM Dox, the percentage of Tunel positive cells rose to 43.3%. These data indicate that WC-II-26 causes an enhancement of Dox-induced apoptosis, and is a potent chemosensitizer.

EXAMPLE 33

This example illustrates that σ2 selective ligands can induce EMT-6 cell death.

Figure 4:
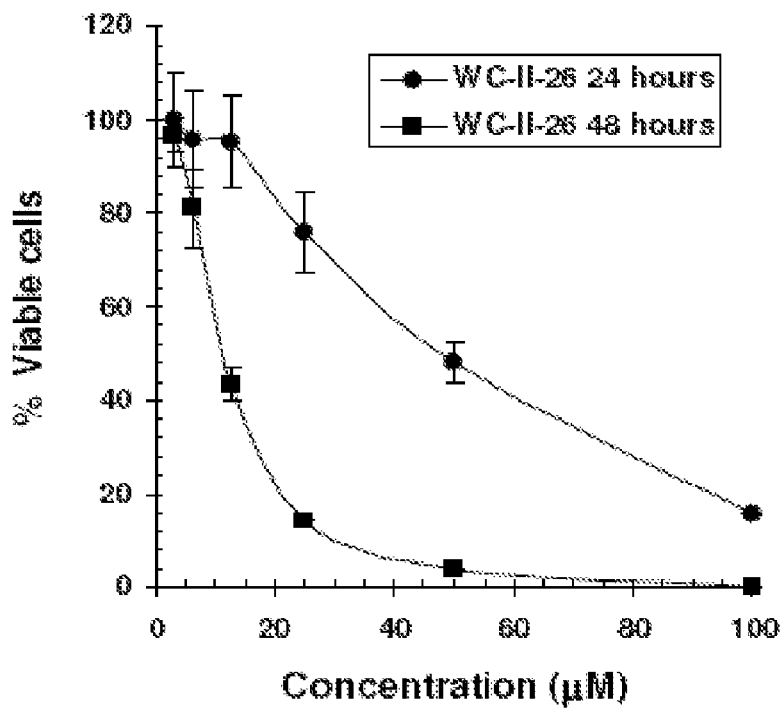
FIG. 4 illustrates cell killing as a function of dose for two σ2 selective ligands, WC-II-26 and SV119. EMT-6 cells were incubated for either 24 h or 48 h in the presence of various concentrations of the σ2 selective ligands. Cell viability was determined by the MTS assay.
Figure 4:
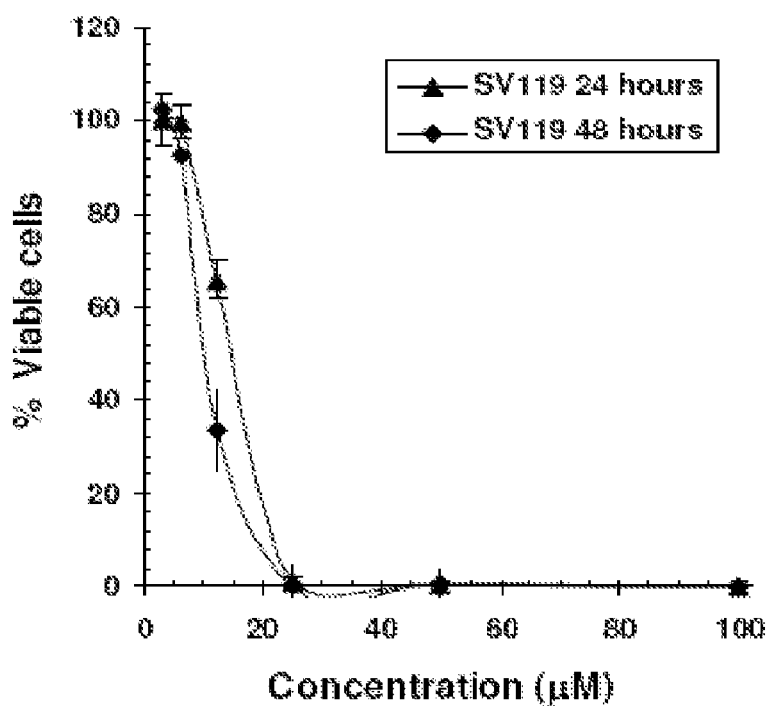

In these experiments, a number of sigma ligands, having a wide range of affinities for σ1 and σ2 receptors, were evaluated for their efficacy to kill EMT-6 cells. These mouse mammary adenocarcinoma cells were chosen because they have a high density of σ2 receptors[21]. Cells were incubated for 24 hours or 48 hours with various concentrations of the sigma ligands. Cytotoxicity and cell viability were quantified using the MTS assay. For most of the ligands, the dose-response relationship (FIG. 4) was adequate to calculate an $IC_{50}$ value after both a 24 h to a 48 h incubation time (Table 2). The most potent sigma ligands for killing EMT-6 cells were those having a high affinity and selectivity for the σ2 receptor versus the σ1 receptor (Table 2). The ligands with a high affinity for both σ1 and σ2 receptors were also moderately cytotoxic. These data suggest that the cytotoxic effect of a sigma ligand depends primarily on its ability to bind tightly to the σ2 receptor.

TABLE 2

Cytotoxic Effects of Sigma Ligands in Breast Cancer Cell Line EMT-6

| Compound | EC50 (μM, 24 hours) | EC50 (μM, 48 hours) | Ki for σ1 (nM) | Ki for σ2 (nM) |
|---|---|---|---|---|
| σ2 Selective Ligands | | | | |
| WC-II-26 | 42.5 ± 3.5 | 12.5 ± 0.6 | 5571.0 | 10.8 |
| SV119 | 16.0 ± 1.4 | 11 ± 1.4 | 1447.0 | 19.9 |
| SV166 | 30.0 ± 1.0 | 18.5 ± 2.1 | 6292.0 | 28.3 |
| SV170 | 51.0 ± 12.7 | 31.5 ± 9.2 | 59.9 | 1.2 |
| SV95 | >400 | 92.5 ± 10.6 | 92.5 | 3.1 |
| RHM-I-138 | 32.5 ± 3.5 | 16.5 ± 2.1 | 544 | 12.3 |
| Non-selective Ligands | | | | |
| Haloperidol | 345 ± 77.8 | 39 ± 1.4 | 1.4 | 47.2 |

EXAMPLE 34

This example illustrates that σ2 selective ligands can induce cell death in human breast cancer cell line MDA-MB-435.

In these experiments, sigma ligands WC-II-26, SV119 and RHM-I-138 were evaluated for their efficacy to kill human MDA-MB-435 breast cancer cells. Cells were treated and analyzed as described for EMT-6 cells in Example 33. In these experiments cells were incubated for 24 hours or 48 hours with various concentrations of the sigma ligands. Results are shown in Table 3. These data suggest that the cytotoxic effect of a sigma ligand depends primarily on its ability to bind tightly to the σ2 receptor.

TABLE 3

Cytotoxic Effects of Sigma Ligands in Human Breast Cancer Cell Line MDA-MB-435.

| Compound | IC50 (μM, 24 hours) | IC50 (μM, 48 hours) |
|---|---|---|
| WC-II-26 | 51.6 ± 6.0 | 43.2 ± 2.0 |
| SV119 | 36.7 ± 3.3 | 20.6 ± 2.7 |
| RHM-I-138 | 26.7 ± 4.3 | 19.0 ± 1.8 |

EXAMPLE 35

This example illustrates that σ2 selective ligands induce cell death through an apoptotic pathway.

To determine if the mechanism by which our σ2 selective ligands kill EMT-6 cells involves apoptosis, cells incubated with σ2 ligands were assayed by the TUNEL method. Positive TUNEL staining would be indicative of DNA fragmentation that is characteristic of apoptosis. In these experiments, DNA fragmentation was detected by TUNEL staining and fluorescence microscopy (FIG. 6). Panel A: untreated cells. Panel B: Cells treated for 48 h with WC-II-26 (40 μM). Panel C: Cells treated for 16 h with SV119 (100 μM). Panel D: Cells treated for 16 h with RHM-I-138 (40 μM). Although untreated EMT-6 cells have few nuclei with TUNEL staining (FIG. 6A), most of the cells incubated for 48 h with 40 μM of WC-II-26 displayed positive TUNEL staining in their nuclei (FIG. 6B). Most of the EMT-6 cells treated for 16 h with 100 μM of SV119 or 40 μM of RHM-I-138 also displayed positive TUNEL staining in their nuclei (FIG. 6C, 6D). Importantly, some of the TUNEL positive cells also exhibited the morphologic hallmarks of apoptotic cell death, i.e., nuclear compaction (pyknosis) and nuclear fragmentation (karyorrhexis). Cell death was also quantified by flow cytometric determination of the percentage of the total EMT-6 cells with positive TUNEL staining. At the designated times after treatment with WC-II-26, SV119 and RHM-I-138, TUNEL positive cells increased from 2% for the untreated control cells to 46%, 37% and 40%, respectively (FIG. 6B).

Figure 7:
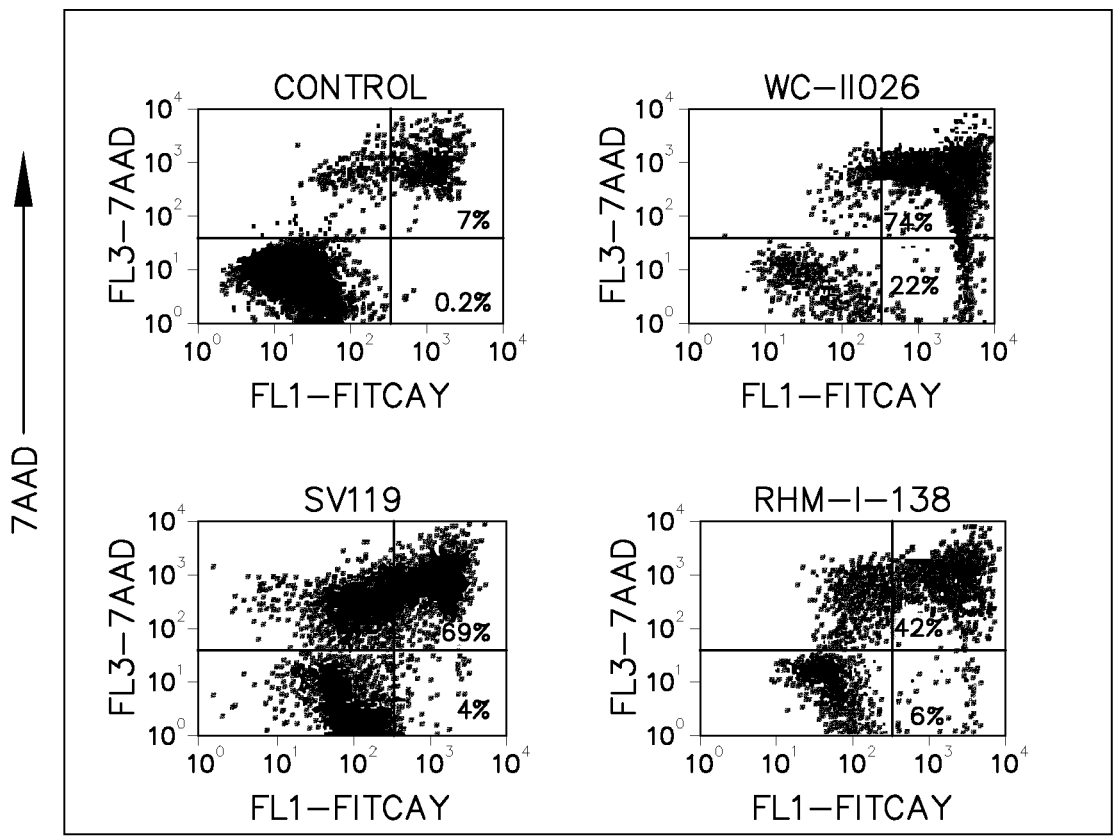
FIG. 7 illustrates flow cytometric determination of the percentage of EMT-6 staining positively for DNA fragmentation, annexin V and/or membrane permeability to 7 AAD after treatment with three σ2 selective ligands. EMT-6 cells were either left untreated or treated with WC-II-26 (40 μM) for 48 h, SV119 (100 μM) for 16 h, or RHM-I-138 (40 μM) for 16 h. A: Representative dot plots for annexin V and 7AAD labeling. B: Representative data of percentage of the total cells with positive TUNNEL staining or annexin V labeling, $p<0.05$; * compared to the control. The data are the mean ±1 SEM from 3 independent experiments.
Figure 7:
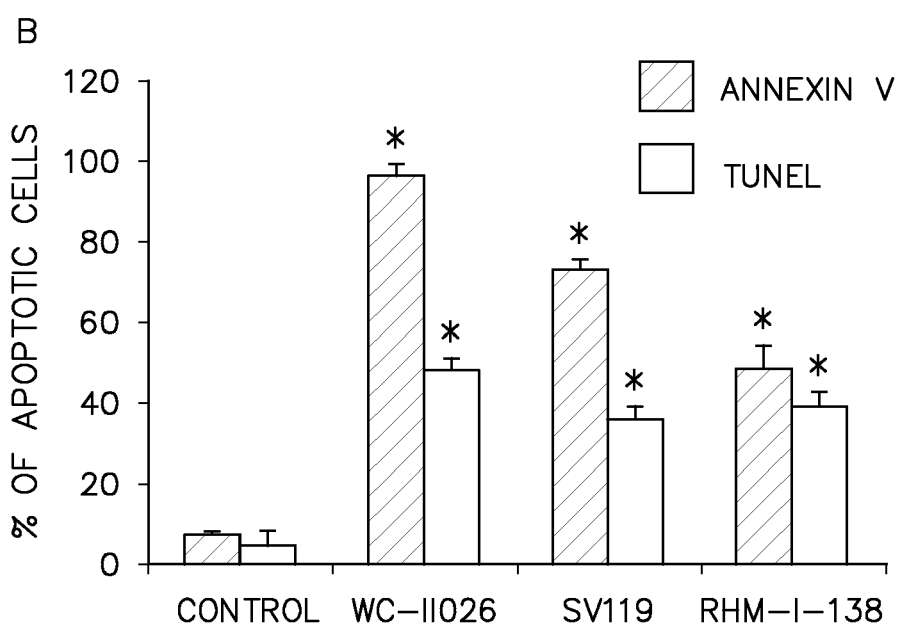

An early step in the induction of apoptosis is the membrane inversion of phosphatidyl serine (PS), which can be detected by the binding of annexin V to the cell surface. In early apoptosis, the cell membrane integrity is still intact, and the fluorescent marker, 7AAD, is excluded from the cell. Therefore, early apoptotic cells are annexin V positive and 7AAD negative. As apoptosis progresses, the cell membrane integrity is lost, and the cells become annexin V positive and 7AAD positive. EMT-6 cells treated with WC-II-26, SV119, and RHM-I-138 were analyzed by flow cytometry, and both early apoptotic death and late apoptotic death were detected after treatment with these three σ2 selective ligands (FIG. 7A). The percentage of EMT-6 cells with positive annexin V staining was 96.6±2.7%, 73.5±2.4%, and 48±6.4% after treatment with WCII-26, SV119 and RHM-I-138, respectively (FIG. 7B). Considered together, the data indicate that these three σ2 selective ligands have the ability to induce cell death through an apoptotic pathway.

EXAMPLE 36

This example illustrates that σ2 receptor ligands induce caspase-3/7 activation.

Figure 8:
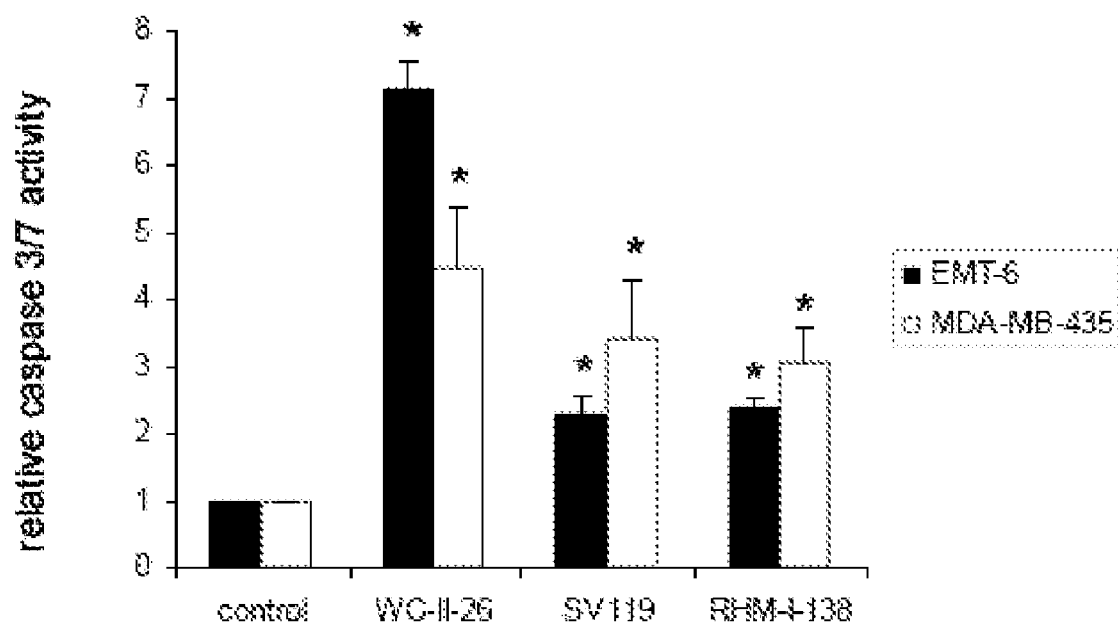
FIG. 8 illustrates activation of caspase-3/7 in EMT-6 cells treated with the sigma-2 selective ligands, WC-II-26, SV119, or RHM-I-138. EMT6 cells were treated for 24 h with concentrations of 40 μM. MDA-MB-435 cells were treated with varying concentrations of sigma-2 selective ligands for 24 h. The highest level of caspase-3/7 activity was detected after 24 h in the presence of 80 μM SV119, 80 μM WC-II-26, and 50 μM RHM-I-138. The data are the mean ±1 SEM of three independent experiments. $p<0.05$; * compared to the control.

In these experiments, to assess whether caspase-like activity was involved in the cytotoxic pathway, a caspase-3/7 whole cell assay was performed. This assay has advantages over other cell-based assays which use a cell lysate to monitor the activity of caspase-3/7. By not disrupting the cells, the whole cell assay tends to minimize the background noise contributed by non-specific protease activity in the cell lysates. Consequently, a greater specificity for the caspase-3/7 activity can be achieved with the whole cell assay. After treating with each σ2 selective ligand, a cell permeable, the non-fluorescent caspase-3/7 specific substrate, Z-DEVDR110, was added to measure the activity of caspase-3/7 in the whole intact cell. The accumulation of the fluorescent product was quantified using a fluorescence microplate reader. A dose-dependent, caspase-3/7 activation was observed after a 24 h treatment with each of the three σ2 selective ligands (FIG. 8). All three σ2 selective ligands induced caspase-3/7 activity in a dose dependent manner. For example, a 24 h treatment with a 40 μM concentration of WC-II-26, SV119 or RHM-I-138 increased caspase 3/7 activity by 7-, 2- and 2-fold, respectively. These data demonstrate that the cell death pathway induced by these three σ2 selective ligands involves the activation of caspase-3/7.

EXAMPLE 37

This example illustrates that caspase inhibitors partially block DNA fragmentation and cytotoxicity induced by σ2 selective ligands.

Figures 1, 9:
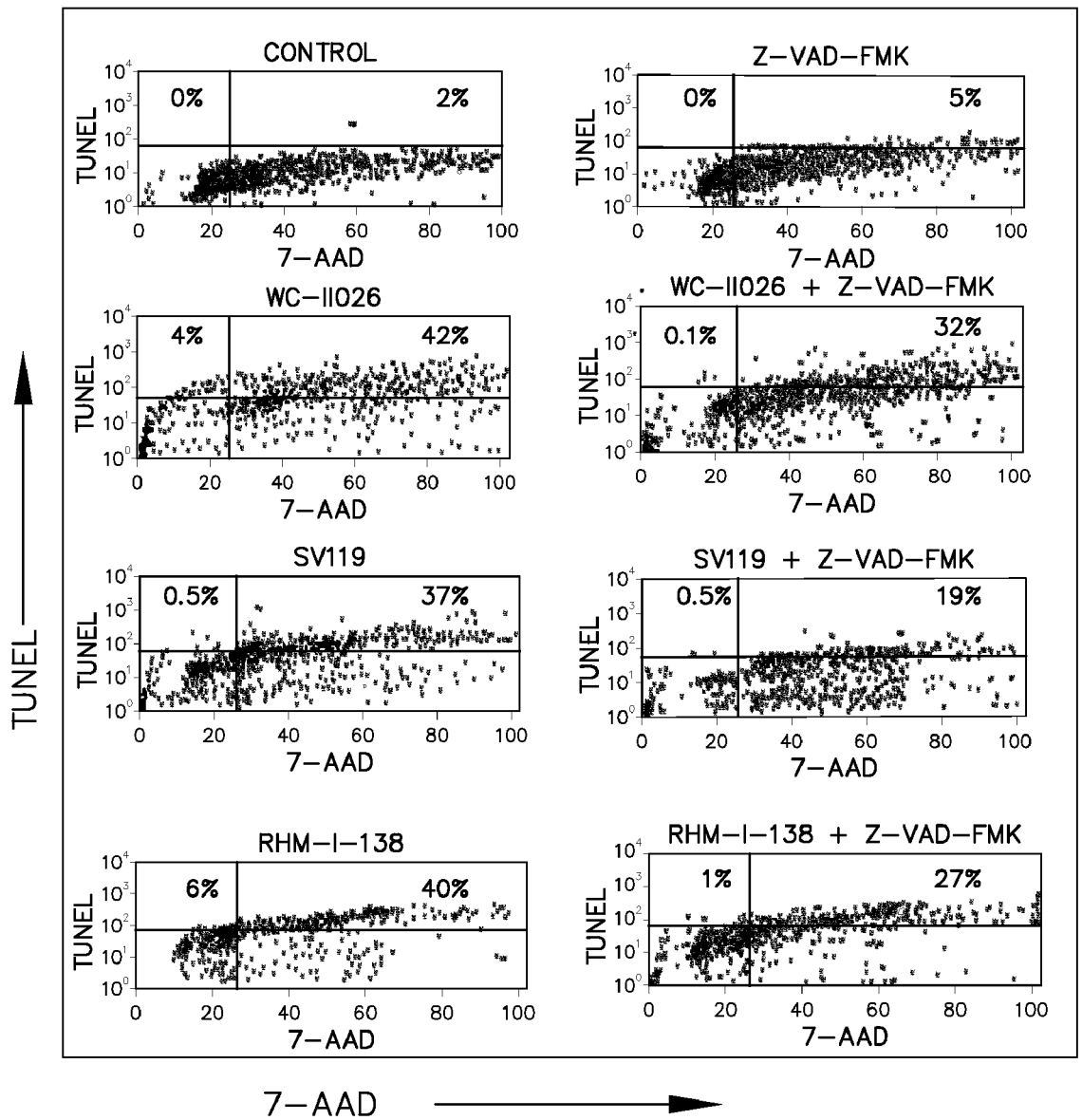
FIG. 9 illustrates flow cytometric determination of the effect of two caspase inhibitors on the DNA fragmentation and cytotoxicity induced by three σ2 selective ligands. EMT-6 cells were pre-treated for 1 h with either Z-VAD-FMK (100 μM), Z-DEVD-FMK (100 μM), or vehicle, and then treated with WC-II-26 (40 μM) for 48 h, SV119 (100 μM) for 16 h, or RHM-I-138 (40 μM) for 16 h. A: Representative dot plots for EMT-6 cells after TUNEL and 7 AAD staining. B: Representative data of percentage of EMT-6 cells staining positively for DNA fragmentation ($p<0.05$; * compared to the control). C: Percentage of viable cells measured by the MTS assay. All the data in panels B and C are the mean ±1 SEM of three independent experiments, p<0.05; * compared to the no inhibitor control.
Figure 9:
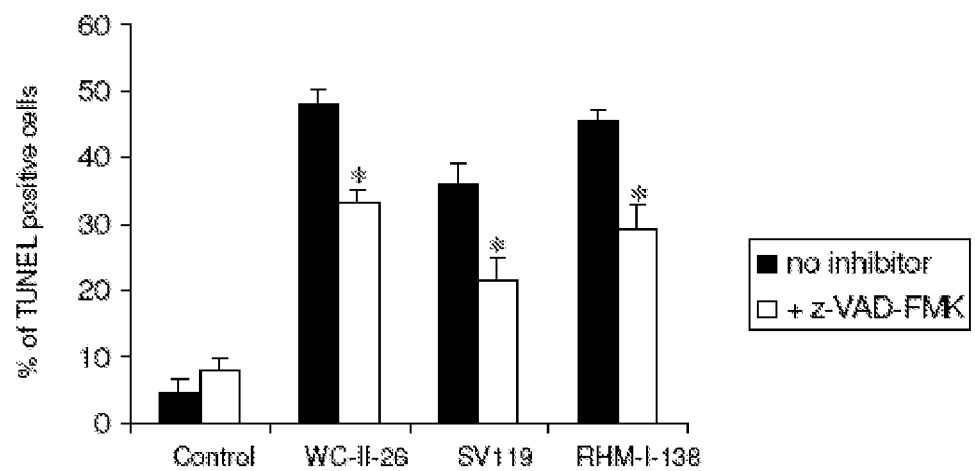
Figure 2:
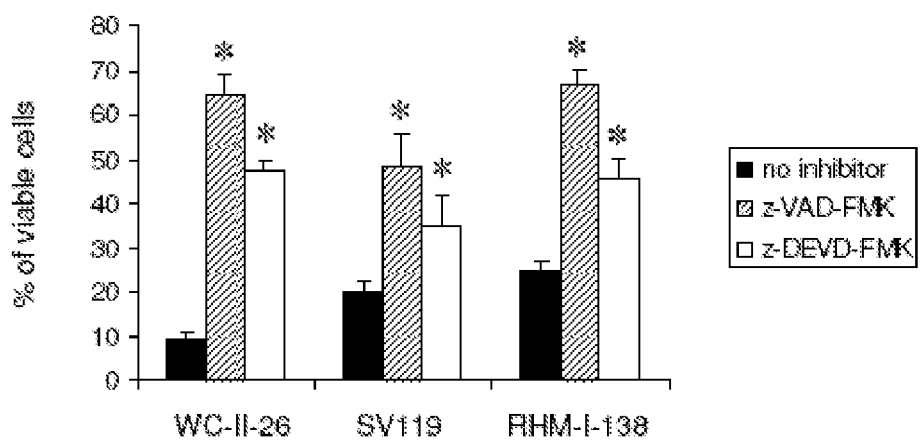

In these experiments, EMT-6 cells were pre-incubated for 1 h with the broad spectrum caspase inhibitor, Z-VAD-FMK, or the specific caspase-3 inhibitor, Z-DEVDFMK, and then treated with the three σ2 selective ligands at the specified concentrations and times (FIG. 9). The DNA fragmentation that occurred after treatment with all three σ2 selective ligands was partially blocked by Z-VAD-FMK (FIGS. 9-1, 9-2). In addition, cell death was partially blocked by the pancaspase inhibitor, Z-VADFMK, and the specific caspase-3 inhibitor, Z-DEVD-FMK (FIG. 9-3). These results indicate that the cell death induced by these σ2 selective ligands was, at least, partially dependent on caspase activation.

EXAMPLE 38

This example illustrates that σ2 selective ligands induce cleavage of procaspase-3 and PARP-1.

Figures 1, 10:
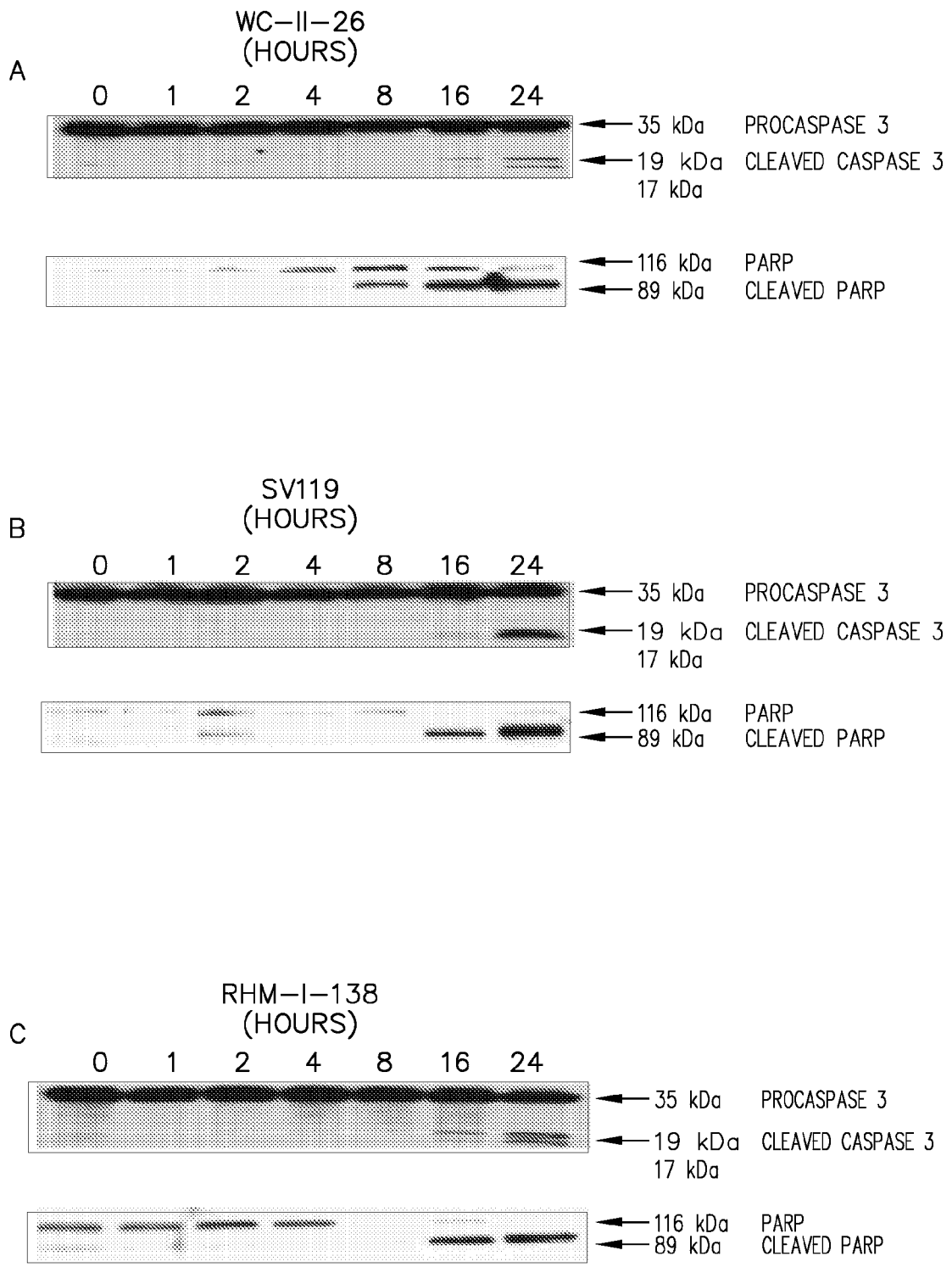
FIG. 10 illustrates Western blot analyses of the pro-caspase-3 and PARP-1 cleavage products after treatment with three σ2 selective ligands. The EMT-6 cells were treated for 0-24 h prior to the assay with, A: WC-II-26 (40 µM), B: SV119 (100 µM), or C: RHM-I-138 (40 µM). MDA-MB-435 cells were treated for 0-24 h prior to the assay with, D: WC-II-26 (80 µM), E: SV119 (100 µM), F: RHM-I-138 (40 µM).
Figures 2, 10:
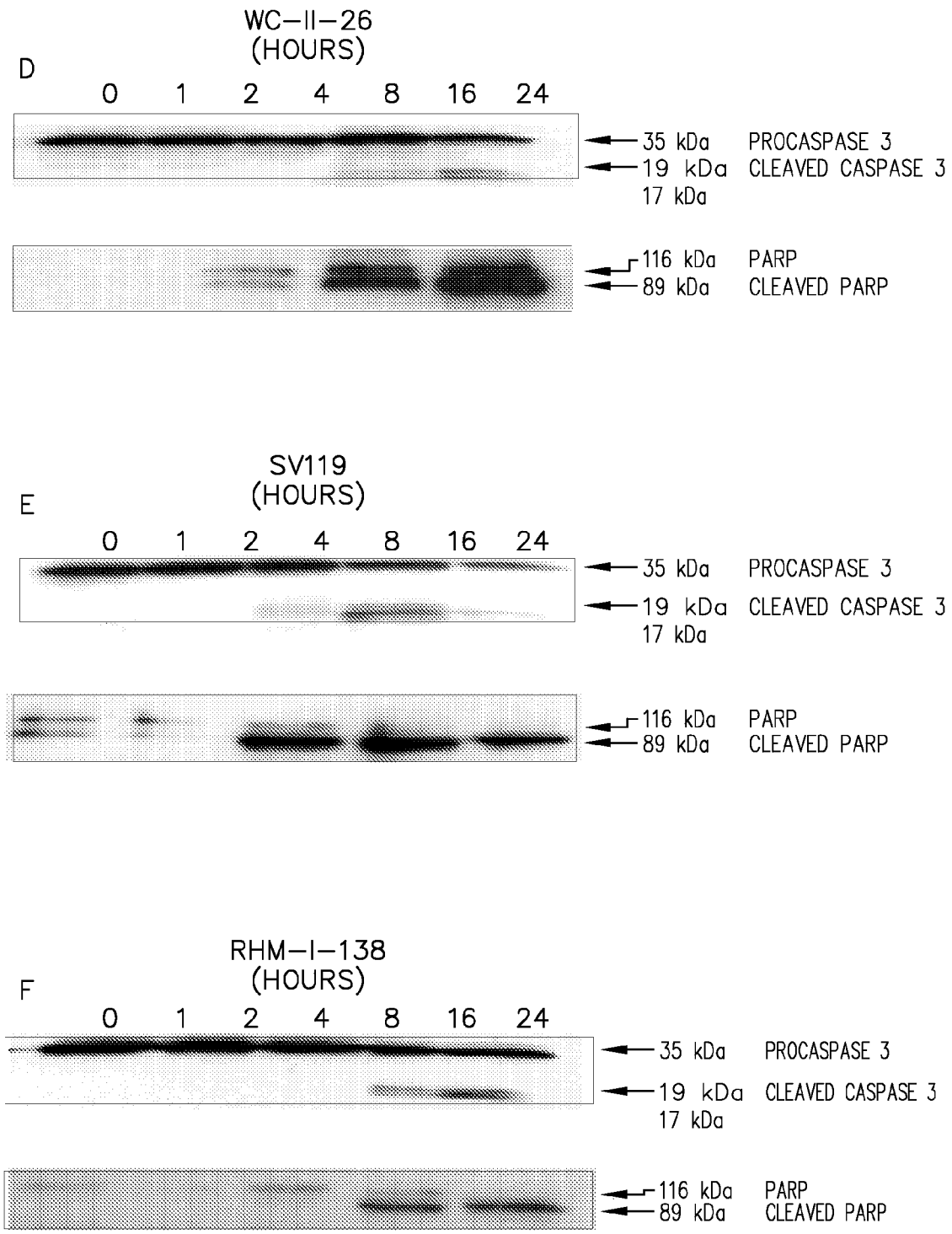
Figure 11:
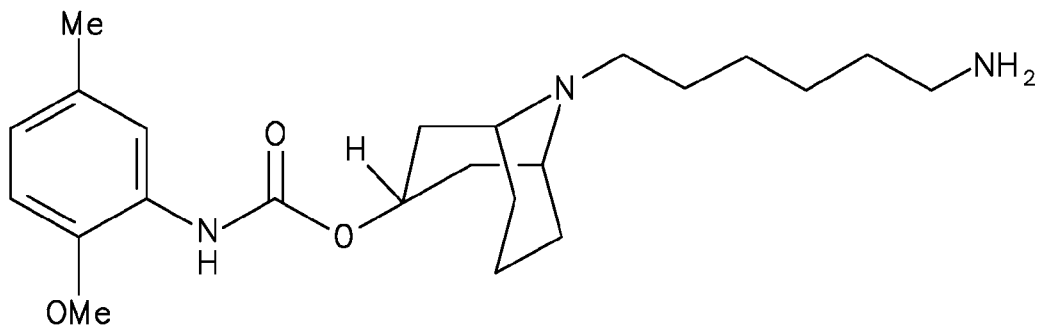
FIG. 11 illustrates structures of three sigma-2 ligands used in some of the studies presented herein.
Figure 11:
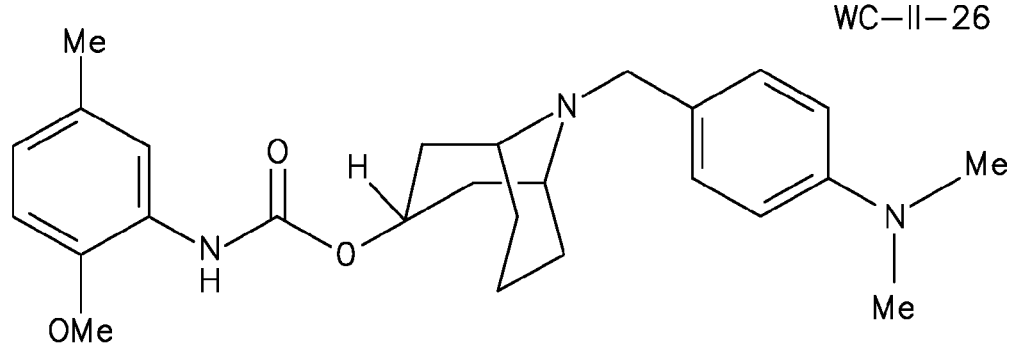
Figure 11:
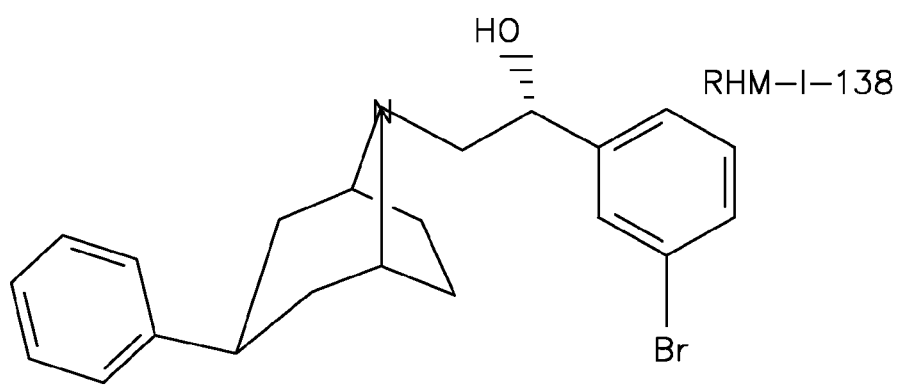
Figure 12:
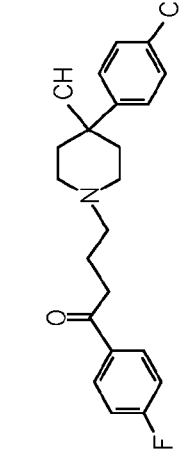
FIG. 12 illustrates structures of some sigma ligands utilized in some studies presented herein. Panel A: Haloperidol is a non-specific sigma-1 and sigma-2 receptor ligand. Panel B: Pentazocine is a sigma-1 specific ligand. Panel C: Sigma-2 receptor-specific ligands SV119 and WC26. Panel D: Chemically- and radiochemically-labeled sigma-2 receptor-specific ligands K05-138 (fluorescein-labeled), RHM-1 ($^3$H-labeled), and RHM-4 ($^{18}$F-labeled).

In these experiments, Western blot analyses were performed to study caspase-3 cleavage (FIG. 10) in order to study whether caspase-3 is activated by treatment with our σ2 selective ligands. Activation of caspase-3 requires proteolytic processing of the inactive procaspase-3 (35 kD) into the active p17 and p12 fragments. For all three σ2 selective ligands, procaspase 3 cleavage was detectable after a 16 h treatment, and this cleavage continued to increase over the next 8 h. PARP-1, the 116 kDa poly(ADP-ribose) polymerase, is one of the main cleavage targets of caspase-3 in vivo[34]. Therefore, we tested whether PARP-1 is cleaved after treating EMT-6 cells with these σ2 selective ligands. The Western blot analyses demonstrated that all three σ2 selective ligands induced PARP-1 cleavage (FIG. 10). These data, along with the results described in the previous sections above, indicate that our σ2 selective ligands induce cell death, in part, through a caspase-3 dependent apoptotic mechanism.

EXAMPLE 39

Figure 13:
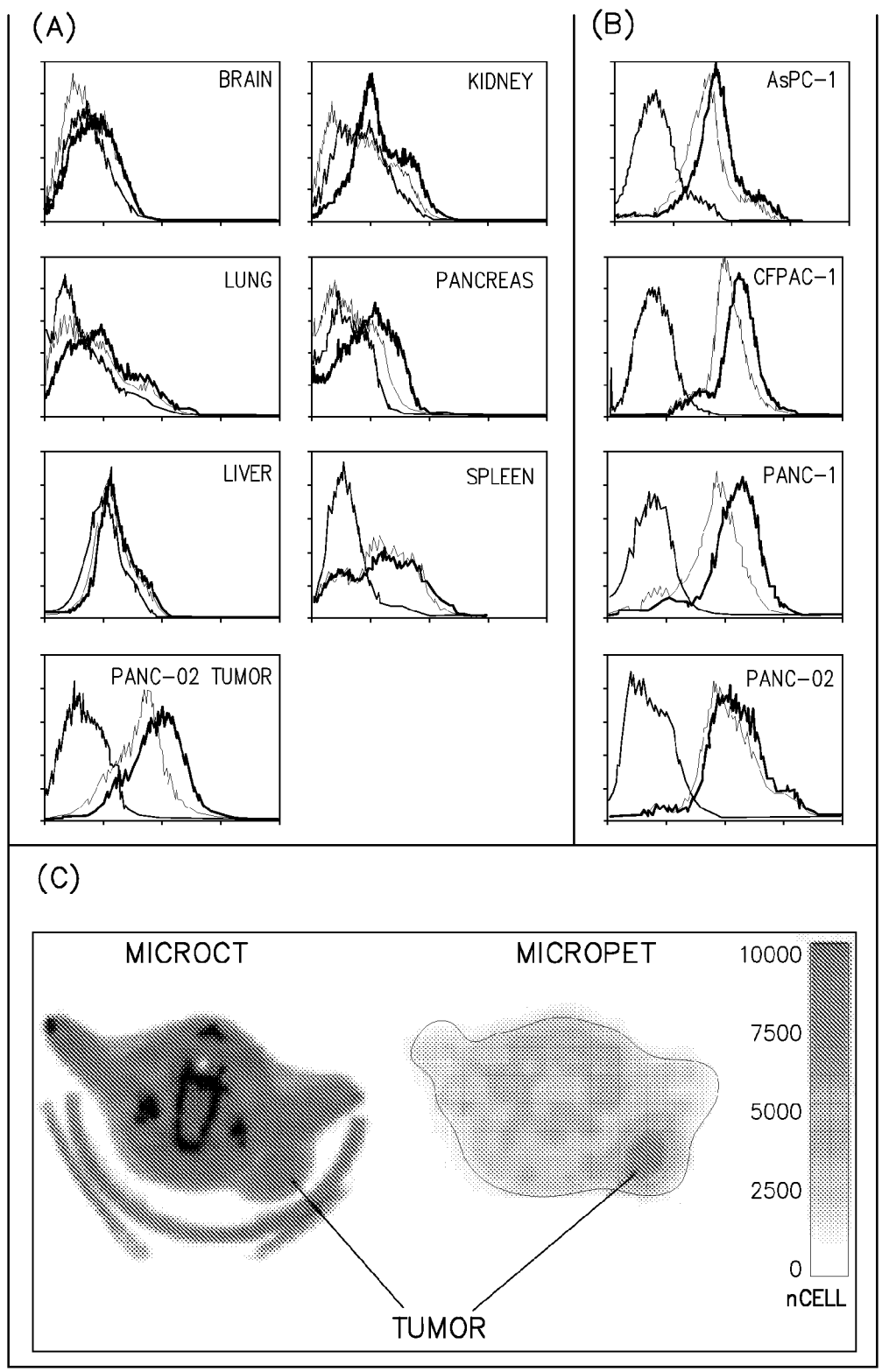
FIG. 13 illustrates that Sigma-2 ligands preferentially bind to cancer as opposed to normal tissues. (A): Single cell suspensions were prepared from liver, lung, pancreas, brain, kidney, spleen and pancreatic tumors (Panc-02 bearing mice). Single cell suspensions were incubated for 1 hour with KO5-138 (a fluorescent labeled sigma-2 receptor ligand, at 50 nM (thin doted line) or 100 nM (thick solid line) of ligand, or left unstained (thin solid line). FACS histograms demonstrate 100 fold more florescence in tumors compared to normal tissues. (B): Human pancreatic cancer lines (CFPAC-1, Panc-1, AsPC-1) demonstrate similar high degree of sigma-2 ligand binding to when compared to our murine model (Panc-02). Fluorescein signal peaks were shown in unstained control (thin solid line), 50 nM of ligand (dotted line), or 100 nM of ligand (thick solid line). The experiment was repeated twice with identical results. (C): Representative Micro PET/CT images of pancreas adenocarcinoma (Panc-02) bearing C57BL/6 mice administered RHM-4 ($^{18}$F-labeled sigma-2 ligand). The tumor indicated by arrows was approximately 1 cm$^3$. The additional hot spot represents metastatic tumor in a regional lymph node.

This example illustrates Sigma-2 receptor expression in vitro and in vivo. In these experiments, Murine pancreatic tumor cells (Panc-02) and human pancreas cancer cell lines (AsPC-1, CFPAC-1, Panc-1) bound high levels of the sigma-2 receptor ligands in vitro (FIGS. 13A and B). Sigma-2 receptor ligands had minimal binding to single cell suspensions prepared from most normal murine tissues including kidney, liver, lung, and brain. Cells from spleen and pancreas exhibited higher binding capacity for sigma-2 receptor ligands at the highest dose tested (100 nM) and the spleen appeared to contain two populations of cells with regard to sigma-2 receptor ligand binding; however, even compared to the high KO5-138-binding population of splenocytes, approximately 10-fold more KO5-138 bound per cell to the syngeneic Panc-02 tumors grown in vivo (FIG. 13B). These findings translated into the ability to image the tumor in vivo using micro-PET (FIG. 2C).

In this and subsequent examples, the following materials and methods were utilized:

Sigma receptor compounds and Chemicals Sigma-1 and sigma-2 receptor ligands (FIG. 1) were synthesized as previously described (Vangveravong. S., et al., Bioorg. Med. Chem. 2006, 14: 6988-6997) or set forth herein. Caspase inhibitors (ZVAD-FMK, YVAD-CHO, and DEVD-CHO) were obtained from Calbiochem (San Diego, Calif.). Unless otherwise specified, all other materials were obtained from Sigma-Aldrich (Saint Louis, Mo., USA).

Cell Lines

Mouse pancreatic cancer (Panc-02) and several human pancreatic cell lines (CFPAC-1, AsPC-1, and Panc-1) were maintained in supplemented RPMI containing glutamine (2 mmol/L), pyruvate (1 mmol/L), penicillin and streptomycin (100 IU/mL), and 10% FBS. All cell culture processes were carried out in a humidified atmosphere of 5% $CO_2$ at 37° C.

Sigma-2 Expression Study In Vitro

Lung, liver, spleen, kidney, pancreas, brain and established tumor from C57BL/6 mice were minced to 1-mm in size and digested in a RPMI buffer containing 1 mg/ml collagenase (Sigma-Aldrich, St. Louis, Mo.) and 0.1 mg/ml DNase (Sigma-Aldrich, St. Louis, Mo.) for 45 min to obtain a single-cell suspensions. After filtering, contaminating erythrocytes were lysed in Ammonium Chloride (ACK) buffer, pelleted and resuspended in PBS (pH 7.4). Single cell suspensions were incubated for 1 hour with KO5-138 (a fluorescent labeled sigma-2 receptor ligand, FIG. 1) at 50 nM or 100 nM of ligand, left unstained. All lines were then washed 3 times with PBS, and evaluated by Fluorescence Activated Cell Sorting (FACS).

Binding Assays (Scatchard Analysis)

The tritiated compound [$^3$H]RHM-1 was synthesized by American Radiolabeled Chemicals, Inc. (St. Louis, Mo.) via O-alkylation of the corresponding phenol precursor as previously described (Tu, Z., et al., Nucl. Med. Biol. 2005, 32: 423-430); chemical purity was greater than 99% and the specific activity of the radioligand was 80 Ci/mmol. Membrane homogenates were prepared from ~400 mg Panc-02 mouse tumor allografts, which were removed from tumor bearing mice and frozen on dry ice immediately and stored at −80° C. until used. Before homogenization, the tumor allografts were allowed to thaw slowly on ice. Tissue homogenization was carried out at 4° C. using a Potter-Elvehjem tissue grinder at a concentration of 1 g of tissue/ml of 50 mM Tris-HCl at pH 8.0. The crude membrane homogenate was then transferred to a 50 ml centrifuge tube and resuspended to a concentration of 200 mg of tissue/ml of 50 mM Tris-HCl. Additional homogenization was accomplished using an Ultra-Turrax T8 polython homogenizer (IKA Works, Inc, Wilmington, N.C.). The final homogenate was then centrifuged for 10 min at 1000 g, the pellet discarded and the supernatant mixed by vortexing and stored at −80° C. until used. The protein concentration of the suspension was determined (DC protein assay, Bio-Rad, Hercules, Calif.) and averaged ~10 mg of protein/ml of stock solution. Approximately 200 μg membrane homogenates were diluted with 50 mM Tris-HCl buffer, pH 8.0 and incubated with [$^3$H]RHM-1 in a total volume of 150 μl at 25° C. in 96 well polypropylene plates (Fisher Scientific, Pittsburgh, Pa.). The concentrations of the radioligand ranged from 0.1-18 nM. After incubation of 60 min, the reactions were terminated by the addition of 150 μl of cold wash buffer (10 mM Tris-HCl, 150 mM NaCl, pH 7.4, at 4° C.) using a 96 channel transfer pipette (Fisher Scientific, Pittsburgh, Pa.), and the samples harvested and filtered rapidly to 96 well fiber glass filter plate (Millipore, Billerica, Mass.) that had been presoaked with 100 μl of 50 mM Tris-HCl buffer, pH 8.0 for 1 hour. Each filter was washed with 200 μl of ice-cold wash buffer for a total of three washes. A Wallac 1450 MicroBeta liquid scintillation counter (Perkin Elmer, Boston, Mass.) was used to quantitate the bound radioactivity, non-specific binding was determined from samples which contained 10 μM RHM-1. The equilibrium dissociation constant (Kd) and maximum number of binding sites (BBmax) were determined by a linear regression analysis of the transformed data using the method of Scatchard.

Data from saturation radioligand binding studies was transformed to determine the Hill coefficient, nH, defined as:

$$\log \frac{B_s}{B_{max} - B_s} = \log K_d + n_H \log L$$

BBs is the amount of the radioligand bound specifically; L is the concentration of radioligand. $n_H$, Hill slope, was determined from Hill plot of $$\frac{B_s}{B_{max} - B_s}$$

versus log L.

Sigma-2 Expression Study In Vivo

MicroPET (positron emission tomography)/CT Imaging was performed to confirm the uptake of the sigma-2 receptor ligand after injection of [$^{18}$F]-labeled Sigma-2 ligand; RHM-4 in tumor bearing mice. Briefly, female C57Bl/6 mice were implanted subcutaneously in the nape of the neck with Panc-02 mouse pancreatic adenocarcinoma cells (1.0×106 cells in 200 μl RPMI) 7-10 days before the study date. Average tumor burden on the day of imaging was ~1.0 cm$^3$. The animals were injected with of [$^{18}$F]-labeled Sigma-2 ligand via tail vein and imaged at 2 hours after injection.

Evaluation of Cytotoxicity of Sigma-2 Ligands In Vitro

Tumor cells were seeded at a density of approximately 0.2×106 cells per well in 12-well plates in 1.0 ml culture medium. Cells were split and pre-incubated at 37° C. in humidified 5% CO2 for more than 24 hours (Panc-02) and 48 hours (CFPAC-1, AsPC-1, Panc-1) to insure uniform growth conditions. Compounds were dissolved in DMSO and added to the culture medium at the concentrations indicated. The final concentration of DMSO in the cell culture medium was less than 1%. The cells were then incubated for 24 hours at 37° C. in humidified 5% CO2. The extent of apoptosis was subsequently measured as previously reported (Guelen, L., et al., Oncogene 2004, 23: 1153-1165). Briefly, staining was performed on trypsin-EDTA treated cultures that had been fixed with 1% paraformaldehyde and 90% methanol. Cell pellets were resuspended in TUNEL reagent (APO-BRDU kit, San Diego, Calif.) or cleaved caspase-3 antibody (Cell Signaling Technology, Inc. Boston, Mass.) and incubated overnight at room temperature (TUNEL) or 4° C. (cleaved caspase-3). After washing, cells were resuspended in fluorescein antibody or 7-AAD buffer and incubated for 1 hour at room temperature. Cell-associated fluorescence was determined using a flow cytometry (FACScan, BD Biosciences) and analyzed with CellQuest software (BD Biosciences).

Antitumor Effect of Sigma-2 Receptor Ligand In Vivo

All studies were performed in accordance with an animal protocol approved by the Washington University Institutional Animal Care Facility. Female C57BL/6 mice (8-12 weeks old) were purchased from the NCI and acclimated for at least 1 week before tumor implantation. All mice were injected in the right flank with 200 μl of a single cell suspension containing 1.0×106 Panc-02 cells. Treatment of the tumors started 2 weeks after tumor implantation when their size reached a mean diameter of 5-8 mm. To evaluate the effect of sigma-2 receptor ligands both systemically and on tumor in vivo, several mice were sacrificed after a single treatment. Necropsy was performed and single cell suspensions were prepared from retrieved organs. The extent of apoptosis in these cells was measured by FACS (described above). For the survival study, mice (N=10 per group) were treated with sigma-2 receptor ligand at the stated concentration or vehicle control once a day for 5 days. Mean tumor diameter was measured three times each week. All mice were euthanized when the tumors reached a mean diameter of 15 mm or when the tumors ulcerated (Hawkins, W. G., et al., J. Surg. Res. 2002, 102: 137-143).

Statistical Analysis

For in vivo experiments, Kaplan-Meier survival curves were plotted and differences were compared using a log-rank test. Tumor sizes and FACS results were analyzed using linear mixed repeated measures models. Hypothesis tests were corrected for multiple testing using a Hochberg step-up procedure. A p-value of less than 0.05 was considered significant for all analyses.

Sigma Receptor Compounds and Chemicals

Sigma-1 and sigma-2 receptor ligands (FIG. 1) were synthesized as previously described (Vangveravong. S., et al., Bioorg. Med. Chem. 2006, 14: 6988-6997) or set forth herein. Caspase inhibitors (ZVAD-FMK, YVAD-CHO, and DEVD-CHO) were obtained from Calbiochem (San Diego, Calif.). Unless otherwise specified, all other materials were obtained from Sigma-Aldrich (Saint Louis, Mo., USA).

Cell Lines

Mouse pancreatic cancer (Panc-02) and several human pancreatic cell lines (CFPAC-1, AsPC-1, and Panc-1) were maintained in supplemented RPMI containing glutamine (2 mmol/L), pyruvate (1 mmol/L), penicillin and streptomycin (100 IU/mL), and 10% FBS. All cell culture processes were carried out in a humidified atmosphere of 5% $CO_2$ at 37° C.

Sigma-2 Expression Study In Vitro

Lung, liver, spleen, kidney, pancreas, brain and established tumor from C57BL/6 mice were minced to 1-mm in size and digested in a RPMI buffer containing 1 mg/ml collagenase (Sigma-Aldrich, St. Louis, Mo.) and 0.1 mg/ml DNase (Sigma-Aldrich, St. Louis, Mo.) for 45 min to obtain a single-cell suspensions. After filtering, contaminating erythrocytes were lysed in Ammonium Chloride (ACK) buffer, pelleted and resuspended in PBS (pH 7.4). Single cell suspensions were incubated for 1 hour with KO5-138 (a fluorescent labeled sigma-2 receptor ligand, FIG. 1) at 50 nM or 100 nM of ligand, left unstained. All lines were then washed 3 times with PBS, and evaluated by Fluorescence Activated Cell Sorting (FACS).

Binding Assays (Scatchard Analysis)

The tritiated compound [$^3$H]RHM-1 was synthesized by American Radiolabeled Chemicals, Inc. (St. Louis, Mo.) via O-alkylation of the corresponding phenol precursor as previously described (Tu, Z., et al., Nucl. Med. Biol. 2005, 32: 423-430); chemical purity was greater than 99% and the specific activity of the radioligand was 80 Ci/mmol. Membrane homogenates were prepared from ~400 mg Panc-02 mouse tumor allografts, which were removed from tumor bearing mice and frozen on dry ice immediately and stored at −80° C. until used. Before homogenization, the tumor allografts were allowed to thaw slowly on ice. Tissue homogenization was carried out at 4° C. using a Potter-Elvehjem tissue grinder at a concentration of 1 g of tissue/ml of 50 mM Tris-HCl at pH 8.0. The crude membrane homogenate was then transferred to a 50 ml centrifuge tube and resuspended to a concentration of 200 mg of tissue/ml of 50 mM Tris-HCl. Additional homogenization was accomplished using an Ultra-Turrax T8 polython homogenizer (IKA Works, Inc, Wilmington, N.C.). The final homogenate was then centrifuged for 10 min at 1000 g, the pellet discarded and the supernatant mixed by vortexing and stored at −80° C. until used. The protein concentration of the suspension was determined (DC protein assay, Bio-Rad, Hercules, Calif.) and averaged ~10 mg of protein/ml of stock solution. Approximately 200 μg membrane homogenates were diluted with 50 mM Tris-HCl buffer, pH 8.0 and incubated with [$^3$H]RHM-1 in a total volume of 150 μl at 25° C. in 96 well polypropylene plates (Fisher Scientific, Pittsburgh, Pa.). The concentrations of the radioligand ranged from 0.1-18 nM. After incubation of 60 min, the reactions were terminated by the addition of 150 μl of cold wash buffer (10 mM Tris-HCl, 150 mM NaCl, pH 7.4, at 4° C.) using a 96 channel transfer pipette (Fisher Scientific, Pittsburgh, Pa.), and the samples harvested and filtered rapidly to 96 well fiber glass filter plate (Millipore, Billerica, Mass.) that had been presoaked with 100 μl of 50 mM Tris-HCl buffer, pH 8.0 for 1 hour. Each filter was washed with 200 μl of ice-cold wash buffer for a total of three washes. A Wallac 1450 MicroBeta liquid scintillation counter (Perkin Elmer, Boston, Mass.) was used to quantitate the bound radioactivity, non-specific binding was determined from samples which contained 10 μM RHM-1. The equilibrium dissociation constant (Kd) and maximum number of binding sites (BBmax) were determined by a linear regression analysis of the transformed data using the method of Scatchard.

Data from saturation radioligand binding studies was transformed to determine the Hill coefficient, nH, defined as:

$$\log\frac{B_s}{B_{max} - B_s} = \log K_d + n_H \log L$$

BBs is the amount of the radioligand bound specifically; L is the concentration of radioligand. $n_H$, Hill slope, was determined from Hill plot of $$\frac{B_s}{B_{max} - B_s}$$

versus log L.

Sigma-2 Expression Study In Vivo

MicroPET (positron emission tomography)/CT Imaging was performed to confirm the uptake of the sigma-2 receptor ligand after injection of [$^{18}$F]-labeled Sigma-2 ligand; RHM-4 in tumor bearing mice. Briefly, female C57Bl/6 mice were implanted subcutaneously in the nape of the neck with Panc-02 mouse pancreatic adenocarcinoma cells (1.0×106 cells in 200 μl RPMI) 7-10 days before the study date. Average tumor burden on the day of imaging was ~1.0 cm$^3$. The animals were injected with of [$^{18}$F]-labeled Sigma-2 ligand via tail vein and imaged at 2 hours after injection.

Evaluation of Cytotoxicity of Sigma-2 Ligands In Vitro

Tumor cells were seeded at a density of approximately 0.2×106 cells per well in 12-well plates in 1.0 ml culture medium. Cells were split and pre-incubated at 37° C. in humidified 5% CO2 for more than 24 hours (Panc-02) and 48 hours (CFPAC-1, AsPC-1, Panc-1) to insure uniform growth conditions. Compounds were dissolved in DMSO and added to the culture medium at the concentrations indicated. The final concentration of DMSO in the cell culture medium was less than 1%. The cells were then incubated for 24 hours at 37° C. in humidified 5% CO2. The extent of apoptosis was subsequently measured as previously reported (Guelen, L., et al., Oncogene 2004, 23: 1153-1165). Briefly, staining was performed on trypsin-EDTA treated cultures that had been fixed with 1% paraformaldehyde and 90% methanol. Cell pellets were resuspended in TUNEL reagent (APO-BRDU kit, San Diego, Calif.) or cleaved caspase-3 antibody (Cell Signaling Technology, Inc. Boston, Mass.) and incubated overnight at room temperature (TUNEL) or 40 C (cleaved caspase-3). After washing, cells were resuspended in fluorescein antibody or 7-AAD buffer and incubated for 1 hour at room temperature. Cell-associated fluorescence was determined using a flow cytometry (FACScan, BD Biosciences) and analyzed with CellQuest software (BD Biosciences).

Antitumor Effect of Sigma-2 Receptor Ligand In Vivo

All studies were performed in accordance with an animal protocol approved by the Washington University Institutional Animal Care Facility. Female C57BL/6 mice (8-12 weeks old) were purchased from the NCI and acclimated for at least 1 week before tumor implantation. All mice were injected in the right flank with 200 µl of a single cell suspension containing 1.0×106 Panc-02 cells. Treatment of the tumors started 2 weeks after tumor implantation when their size reached a mean diameter of 5-8 mm. To evaluate the effect of sigma-2 receptor ligands both systemically and on tumor in vivo, several mice were sacrificed after a single treatment. Necropsy was performed and single cell suspensions were prepared from retrieved organs. The extent of apoptosis in these cells was measured by FACS (described above). For the survival study, mice (N=10 per group) were treated with sigma-2 receptor ligand at the stated concentration or vehicle control once a day for 5 days. Mean tumor diameter was measured three times each week. All mice were euthanized when the tumors reached a mean diameter of 15 mm or when the tumors ulcerated (Hawkins, W. G., et al., J. Surg. Res. 2002, 102: 137-143).

Statistical Analysis

For in vivo experiments, Kaplan-Meier survival curves were plotted and differences were compared using a log-rank test. Tumor sizes and FACS results were analyzed using linear mixed repeated measures models. Hypothesis tests were corrected for multiple testing using a Hochberg step-up procedure. A p-value of less than 0.05 was considered significant for all analyses.

EXAMPLE 40

This example illustrates binding assays demonstrating one-site and non-cooperative binding characteristics of [$^3$H] RHM-1.

Figure 14:
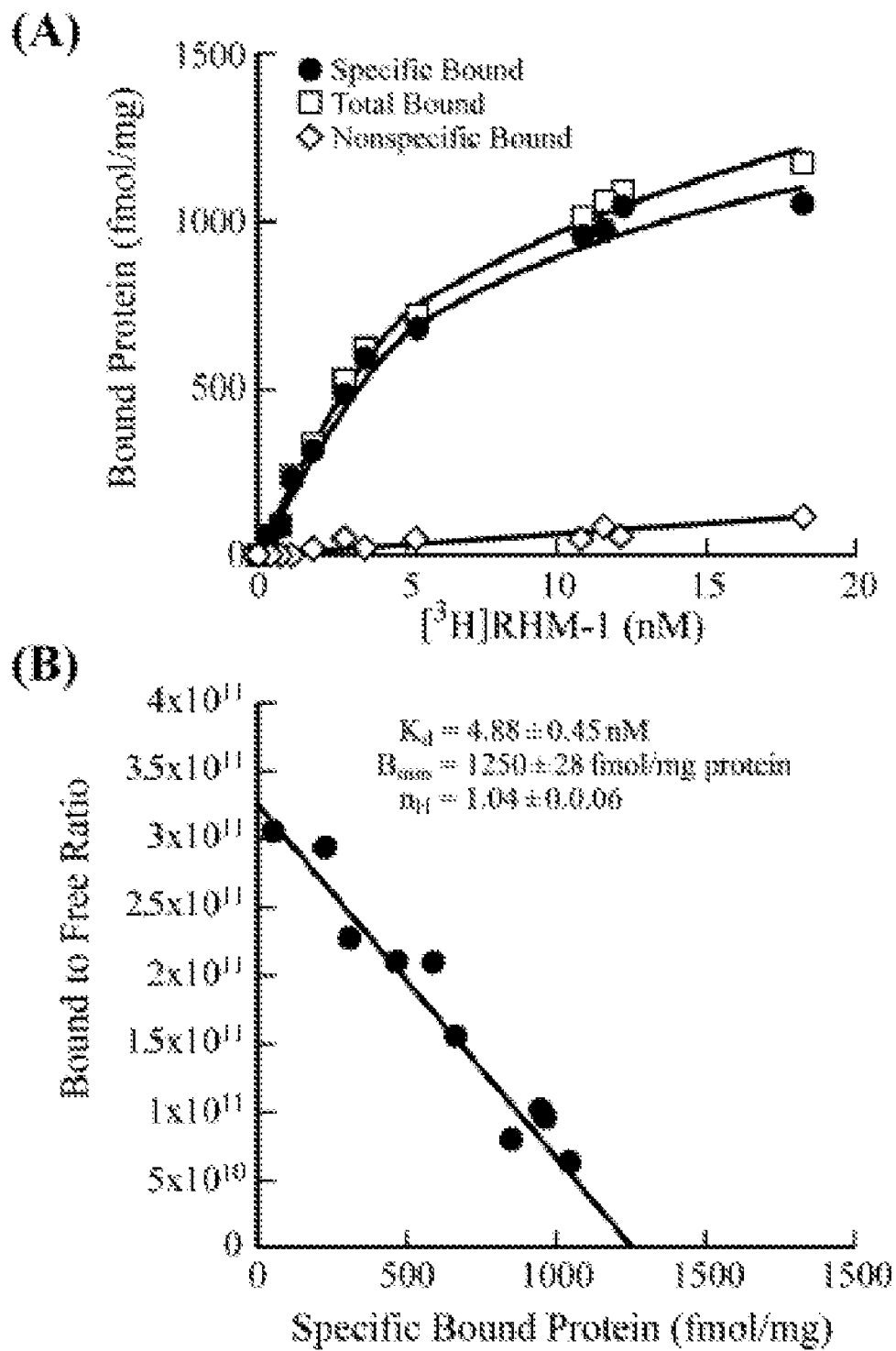
FIG. 14 illustrates Scatchard analysis of [$^3$H]RHM-1 binding to the sigma-2 receptors in membrane homogenates from Panc-02 tumor allografts. (A): Representative saturation binding experiments which show the total bound, non-specific bound and specific bound. (B): Representative Scatchard plots which were used to determine Kd and BBmax values.

In these experiments, direct saturation binding studies were carried out using [$^3$H]RHM-1 with membrane homogenates of PancO2 tumor allografts. Based on Scatchard analysis, the Kd and BBmax values of the receptor-radioligand binding of [$^3$H]RHM-1 were 4.88 nM and 1250 fmol/mg protein (FIG. 14). The mean of $n_H$ H values was close to unity, suggesting that the receptor binding of [$^3$H]RHM-1 displayed one-site and non-cooperative binding characteristics.

EXAMPLE 41

This example illustrates that Sigma-2 receptor ligand induces caspase-3/7 dependent cancer cell apoptosis.

Figure 15:
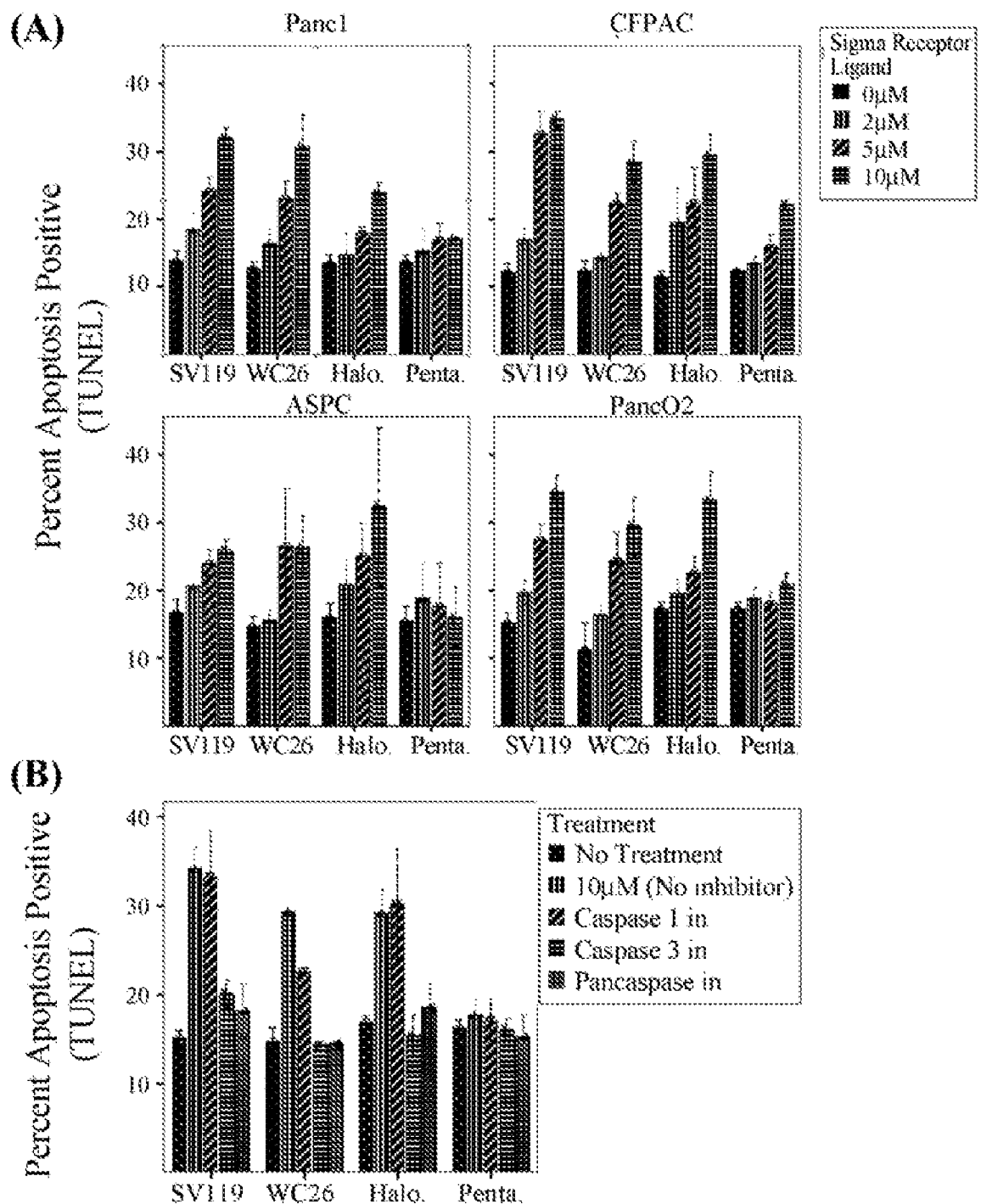
FIG. 15 illustrates that Sigma-2 receptor ligands induce apoptosis of pancreatic cancer cells via a caspase 3 dependent pathway. (A): Treatment with WC26, SV119 and haloperidol (Halo.) caused dose-dependent apoptosis in all pancreatic cancer cell lines tested. At the highest dose tested, all sigma-2 receptor ligands resulted in significant apoptosis (25-35%, p<0.05). (B): Sigma-2 related apoptosis was prevented by pan-caspase inhibitor (Z-VAD-fmk) and caspase-3/7 inhibitor (DEVD-CHO), while the caspase-1 inhibitor (YVAD-CHO) had no effect (Panc-02 cells).

In these experiments, treatment with sigma-2 specific ligands (WC26 and SV119) and the sigma-1/sigma-2 promiscuous ligand haloperidol caused dose-dependent apoptosis in all pancreas cancer cell lines tested. All cell lines tested had a background rate of 10-15% apoptosis over the incubation period. At the highest dose tested (10 µM), all sigma-2 receptor ligands induced an additional 10-20% of the cells to undergo apoptosis (FIG. 15A). The sigma-1 receptor-specific ligand pentazocine had minimal toxicity to all cell lines tested with the exception of CFPAC-1 which exhibited an 8-10% increase in apoptosis at the highest dose tested. The pancaspase inhibitor (Z-VAD-fmk) and caspase-3/7 inhibitor (DEVD-CHO) prevented sigma-2 receptor ligand-induced apoptosis in panc-02 cells, while the caspase-1 inhibitor (YVAD-CHO) had no effect (FIG. 15B). Similar results were seen with human pancreatic cancer cell lines (AsPC-1, CFPAC-1, Panc-1, data not shown).

EXAMPLE 42

This example illustrates that in vivo treatment with a sigma-2 receptor ligand causes tumor apoptosis with minimal effects on normal tissues.

Figure 16:
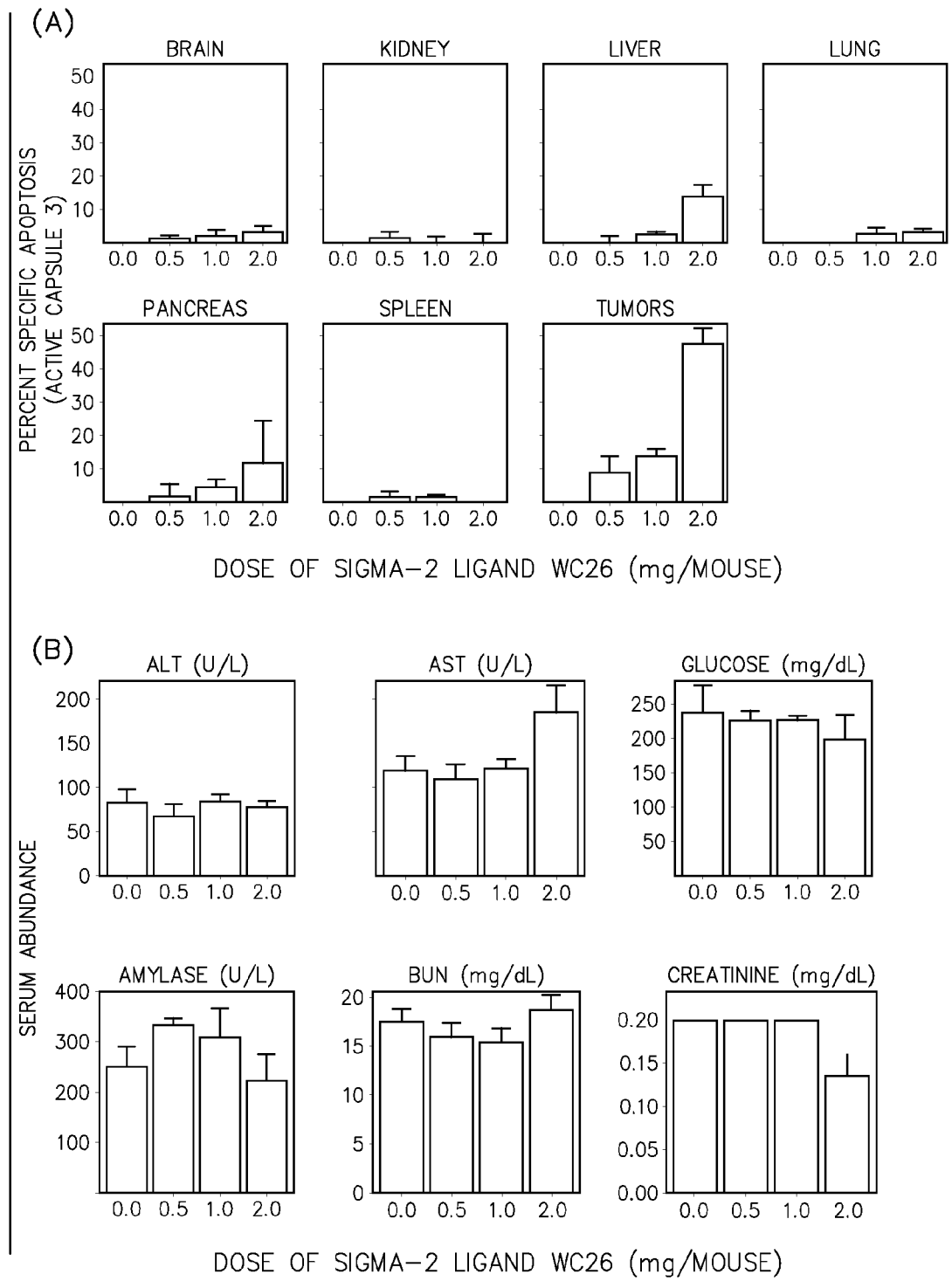
FIG. 16 illustrates that Systemic administration of Sigma-2 receptor ligand induces substantial tumor apoptosis without major toxicity. (A): Systemic administration of the sigma-2 receptor ligand WC26 induces considerable apoptosis in Panc-02 tumor allografts (up to 50% of tumor cells were active caspase-3 positive following a single 2 mg dose of WC26, p<0.0001). Data reported as percent specific apoptosis (percent specific apoptosis=observed apoptosis−tissue specific background apoptosis). (B): The mice appeared normal and no apparent toxicity was noted in serum biochemical analysis or by immunohistochemistry (data not shown). Reference ranges for the blood chemistry panel in C57Bl/6 mice: ALT: 18-184 U/L, AST: 55-251 U/L, glucose: 174-335 mg/dL, amylase: 2595+/−212 U/L, BUN: 34-58 mg/dL, creatinine<1.1 mg/dL.

Systemic administration of the sigma-2 receptor ligand WC26 did not induce apoptosis in brain, lung, kidney or spleen at any of the concentrations tested as measured by FACS for active caspase-3 (FIG. 16A). There was a small amount of apoptosis (<10%) in the pancreas and livers of these animals while their tumors had dose dependent increases in apoptosis (up to 50% of tumor cells were active caspase-3 positive following a single 2 mg dose of WC26, p<0.0001). The mice appeared normal and no apparent toxicity was noted in serum biochemistry data (FIG. 16B). There was a modest effect at the highest dose of WC26 tested with elevated AST and depressed creatinine and glucose levels, though these values are still within their reference ranges (Zhou, X., et al., Comp. Med. 2004, 54: 176-178).

EXAMPLE 43

This example illustrates that Sigma-2 receptor ligand therapy slows tumor growth and confers a survival advantage in vivo.

Figure 17:
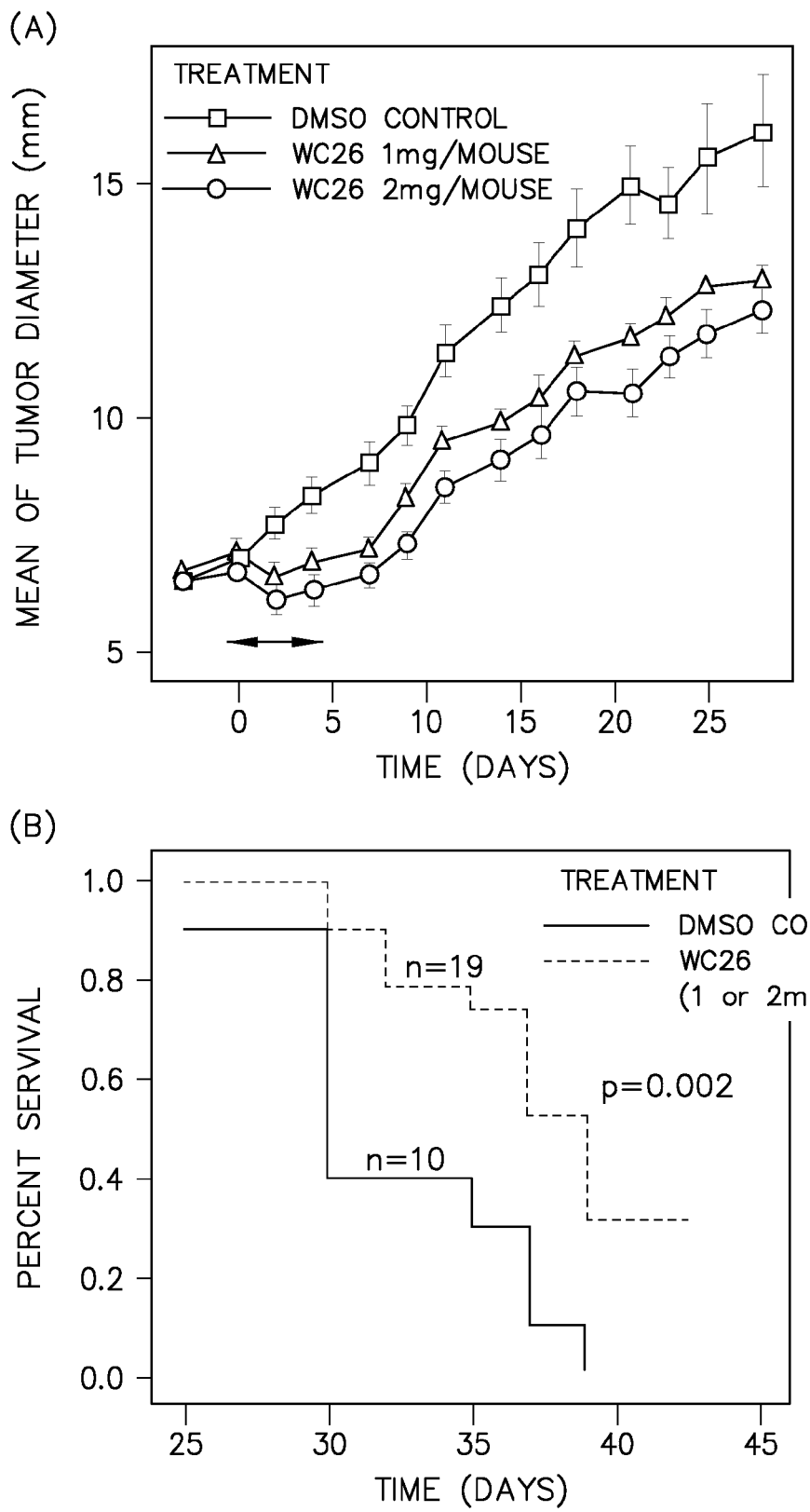
FIG. 17 illustrates that Systemic administration of sigma-2 receptor ligand slows tumor growth and improves survival. Mice with established pancreas tumors were treated with 5 days of WC26 in one of two dose ranges (2 mg/day, n=9; Dash line or 1 mg/day n=10; dashed line) or vehicle control (20% DMSO n=10; solid line). (A): Mice treated with WC26 had smaller tumors compared to animals vehicle control (p<0.0001). The two treatment groups were not statistically different. The double-headed arrow denotes the treatment period (5 days). (B): Survival of mice treated with WC26 compared favorably to the mice treated vehicle control (p=0.002). Survival endpoints were defined as tumor diameter>15 mm or tumor ulceration.

In these experiments, the anti-tumor properties of sigma-2 receptor ligand (WC26) monotherapy were evaluated in vivo in an established syngeneic tumor model using Panc-02 cells in C57BL/6 mice. Once tumors were established (5-8 mm diameter), mice were randomized into one of three treatment groups: daily intraperitoneal injection of 50 or 100 mg/kg of WC26 or vehicle control (20% DMSO, 200 µl) once a day for five days. In both WC26 treatment groups, tumors shrank during and immediately following treatment while tumors in the vehicle-treated animals continued to grow (FIG. 17A). Although regrowth occurred in the Sigma-2 ligand treatment groups after treatment was stopped, there was a significant delay compared to control animals. Using tumor burden of 15 mm or ulceration as a surrogate endpoint for survival, we found a significant survival benefit in the Sigma-2 receptor ligand treatment group (FIG. 17B; p=0.002). Based on blood chemistry parameters, there was no acute, systemic toxicity observed in any of the treated animals. In addition, no acute toxicity was observed on immunohistochemical evaluation of normal tissues after WC26 treatment (data not shown).

All publications, patents, patent applications and other references cited in this application are herein incorporated by reference in their entirety as if each individual publication, patent, patent application or other reference were specifically and individually indicated to be incorporated by reference.

REFERENCES

1. Martin, W. R.; Eades, C. G.; Thompson, J. A.; Huppler, R. E.; Gilbert, P. E. J. Pharmacol. Exp. Ther. 1976, 197, 517-532.
2. Walker, J. M.; Bowen, W. D.; Walker, F. O.; Matsumoto, R. R.; de Costa, B. R.; Rice, K. C. Pharmacol. Rev. 1990, 42, 355-402.
3. Hanner, M.; Moebius, F. F.; Flandorfer, A.; Knaus, H.-G.; Striessnig, J.; Kempner, E.; Glossmann, H. Proc. Natl. Acad. Sci. U.S.A. 1996, 93, 8072-8077.
4. Kekuda, R.; Prasad, P. D.; Fei, Y.-J.; Leibach, F. H.; Ganaphthy, V. Biochem. Biophys. Res. Commun. 1996, 229, 553-558.

5. Seth, P.; Leibach, F. H.; Ganaphthy, V. Biochem. Biophys. Res. Commun. 1997, 241, 535-540.
6. Hellewell, S. B.; Bruce, A.; Feinstein, G.; Orringer, J.; Williams, W.; Bowen, W. D. Eur. J. Pharmacol., Mol. Pharmacol. Sec. 1994, 268, 9-18.
7. Bem, W. T.; Thomas, G. E.; Mamone, J. Y.; Homan, S. M.; Levy, B. K.; Johnson, F. E.; Coscia, C. J. Cancer Res. 1991, 55, 6558-6562.
8. Vilner, B. J.; John, C. S.; Bowen, W. D. Cancer Res. 1995, 55, 408-413.
9. Mach, R. H.; Smith, C. R.; al-Nabulsi, I.; Whirrett, B. R.; Childers, S. R.; Wheeler, K. T. Cancer Res. 1997, 57, 156-161.
10. Al-Nabulsi, I.; Mach, R. H.; Wang, L. M.; Wallen, C. A.; Keng, P. C.; Sten, K.; Childers, S. R.; Wheeler, K. T. Br. J. Cancer 1999, 81, 925-933.
11. Wheeler, K. T.; Wang, L. M.; Wallen, C. A.; Childers, S. R.; Cline, J. M.; Keng, P. C.; Mach, R. H. Br. J. Cancer 2000, 82, 1223-1232.
12. Crawford, K. W.; Bowen, W. D. Cancer Res. 2002, 62, 313-322.
13. Ostenfeld, M. S.; Fehrenbacher, N.; Hoyer-Hansen, M.; Thomsen, C.; Farkas, T.; Jaattela, M.; Nylandsted, J.; Gyrd-Hansen, M.; Danielewicz, A.; Lademann, U.; Weber, E.; Multhoff, G.; Rohde, M.; Poulsen, B.; Felbor, U.; Kallunki, T.; Boes, M.; Leist, M.; Dietrich, N.; Thastrup, J.; Holmberg, C.; Lerdrup, M.; Herdegen, T. Cancer Res. 2005, 65, 8975-8983.
14. Bowen, W. D.; Bertha, C. M.; Vilner, B. J.; Rice, K. E. Eur. J. Pharmacol. 1995, 278, 257-260.
15. Nguyen, V. H.; Kassiou, M.; Johnston, G. A. R.; Christie, M. J. Eur. J. Pharmacol. 1996, 311, 233-240.
16. Bonhaus, D. W.; Loury, D. N.; Jakeman, L. B.; To, Z.; DeSouza, A.; Eglen, R. M.; Wong, E. H. J. J. Pharmacol. Exp. Ther. 1993, 267, 961-970.
17. Mach, R. H.; Vangveravong, S.; Huang, Y.; Yang, B.; Blair, J. B.; Wu, L. Med. Chem. Res. 2003, 11, 380-398.
18. Mach, R. H.; Yang, B.; Wu, L.; Kuhner, R. J.; Whirrett, B. R.; West, T. Med. Chem. Res. 2001, 10, 339-355.
19. Boon, J. M.; Lambert, T. N.; Smith, B. D.; Beatty, A. M.; Ugrinova, V.; Brown, S. N. J. Org. Chem. 2002, 67, 2168-2174.
20. Cheng, Y. C.; Prusoff, W. H. Biochem. Pharmacol. 1973, 22, 3099-3108.
21. Xu, J.; Tu, Z.; Jones, L. A.; Vangveravong, S.; Wheeler, K. T.; Mach, R. H. Eur. J. Pharmacol. 2005, 525, 8-17.
22. John, C. S.; Vilner, B. J.; Schwartz, A. M.; Bowen, W. D. J. Nucl. Med. 1996, 37, 267P, 1996.
23. Kawamura, K.; Elsinga, P. H.; Kobayashi, T.; Ishii, S.; Wang, W. F.; Matsuno, K.; Vaalburg, W.; Ishiwata, K. Nuclear Medicine & Biology, 2003, 30: 273-284.
24. Mach, R. H.; Huang, Y.; Buchheimer, N.; Kuhner, R.; Wu, L.; Morton, T. E.; Wang, L.; Ehrenkaufer, R. L.; Wallen, C. A.; Wheeler, K. T. Nuclear Medicine & Biology, 200, 28: 451-458.
25. John, C. S.; Gulden, M. E.; Li, J.; Bowen, W. D.; McAfee, J. G.; Thakur, M. L. Nuclear Medicine & Biology, 1998, 25: 189-194.
26. Caveliers, V.; Everaert, H.; Lahoutte, T.; Dierickx, L. O.; John, C. S.; and Bossuyt, A.; European Journal of Nuclear Medicine, 2001, 28: 133-135.
27. Jacobson, M. D., Weil, M., and Raff, M. C. Cell, 88: 347-354, 1997.
28. Reed, J. C. Nature Reviews Drug Discovery, 1: 111-121, 2002.
29. Brent, P. J., Pang, G., Little, G., Dosen, P. J., and Van Helden, D. F. Biochemical & Biophysical Research Communications, 219: 219-226, 1996.
30. Barbieri, F., Sparatore, A., Alama, A., Novelli, F., Bruzzo, C., and Sparatore, F. Oncology Research, 13: 455-461, 2003.
31. Mach, R. H., Huang, Y., Freeman, R. A., Wu, L., Vangveravong, S., and Luedtke, R. R. Bioorganic & Medicinal Chemistry Letters, 14: 195-202, 2004.
32. Huang, Y., Hammond, P. S., Whirrett, B. R., Kuhner, R. J., Wu, L., Childers, S. R., and Mach, R. H. Journal of Medicinal Chemistry, 41: 2361-2370, 1998.
33. Huang Y, H. P., Wu L, Mach R H J Med Chem, 44: 4404-4415, 2001.
34. Mach, R. H. In: Daniel P. Shuster and Timothy S. Blackwell (ed.) Molecular Imaging of the Lungs. Lung Biology in Health and Disease, Marcel Dekker, Inc., 203: 327-348, 2005.
35. Tu Z., D. C. S., Ponde D. E., Jones L., Wheeler K. T., Welch M. J., Mach R. H Nucl. Med. Biol., 32: 423-430, 2005.
36. Mach R H, W. K., Blair S. Yang B. Day C S, Blair J B, Choi S R, Kung K F J Labelled Cpd Radiopharm, 44: 899-908, 2001.
37. Choi, S. R., Yang, B., Plossl, K., Chumpradit, S., Wey, S. P., Acton, P. D., Wheeler, K., Mach, R. H., and Kung, H. F. Nuclear Medicine & Biology, 28: 657-666, 2001.
38. Vilner, B. J., de Costa, B. R., and Bowen, W. D. Journal of Neuroscience, 15: 117-134, 1995.
39. Rockwell, S, and Kelley, M. Radiat. Oncol. Investig. 6, 199-208, 1998.

The Present Disclosure Includes the Following Aspects.
1. A compound of formula (I):

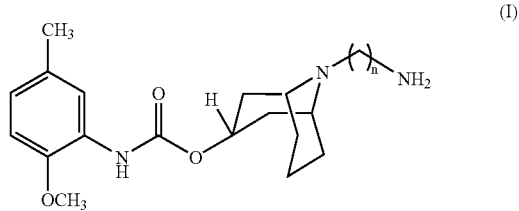

wherein n is an integer from 1 to about 20, or a salt thereof.
2. A compound or salt thereof in accordance with aspect 1, wherein n is an integer from at least 4 up to 12.
3. A compound or salt thereof in accordance with aspect 1, wherein n=4, 6 or 10.
4. A compound of formula (II):

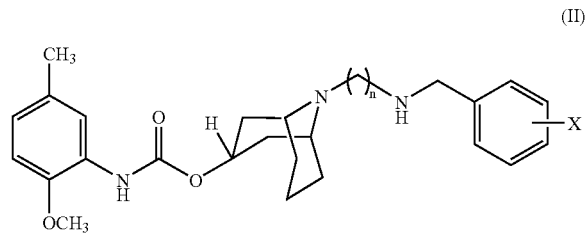

wherein n is an integer from 1 to about 20, and wherein X is a halogen atom attached to the phenyl group at position 3 or 4, wherein the halogen atom is selected from the group consisting of Cl, Br, F, and I, or a salt thereof.

5. A compound or salt thereof in accordance with aspect 4, wherein n=4 or 6.

6. A compound or salt thereof in accordance with aspect 4, wherein X is selected from the group consisting of 3-Br, 3-F, 3-I, 4-Br, 4-F, and 4-I.

7. A compound or salt thereof in accordance with aspect 5, wherein n=6 and the halogen atom is attached at the 4 position.

8. A compound of formula (III):

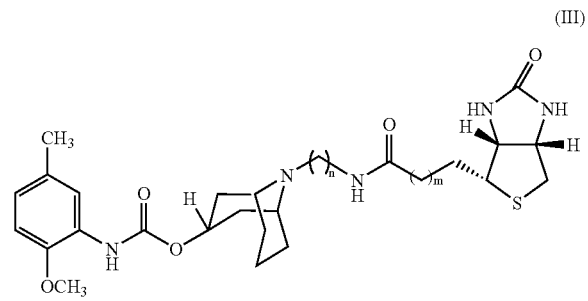

(III)

wherein m is an integer from 1 to about 20 and n is an integer from 1 to about 20, or a salt thereof.

9. A compound or salt thereof in accordance with aspect 8, wherein m=3 and n=6 or 10.

10. A compound of formula (IV)

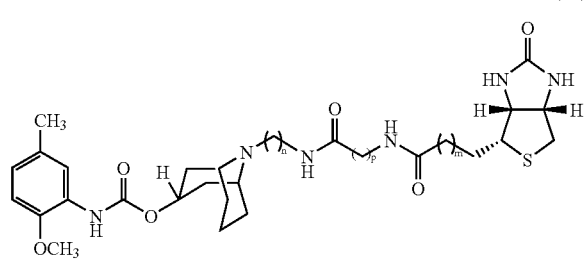

(IV)

wherein m is an integer from 1 to about 20, n is an integer from 1 to about 20 and p is an integer from 1 to about 20, or a salt thereof.

11. A compound or salt thereof in accordance with aspect 10, wherein m=3, n=6 or 10, and p=5.

12. A compound of formula (V):

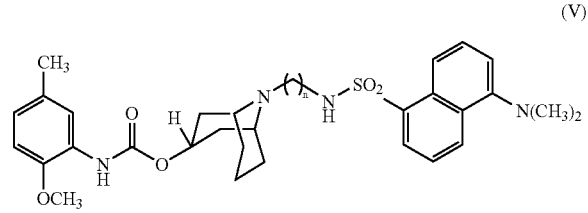

(V)

wherein n is an integer from 1 to about 20, or a salt thereof.

13. A compound or salt thereof in accordance with aspect 12, wherein n=6.

14. A compound of formula (VI):

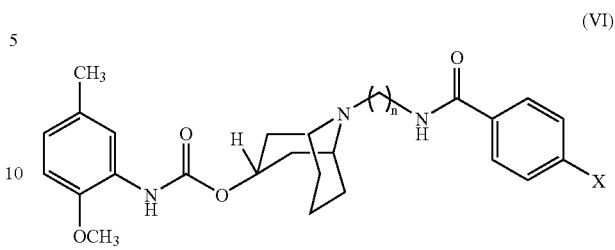

(VI)

wherein n is an integer from 1 to about 20, and wherein X is a halogen atom selected from the group consisting of Cl, Br, F, and I, or a salt thereof.

15. A compound or salt thereof in accordance with aspect 14, wherein n=4, 6 or 10.

16. A compound of formula (VII):

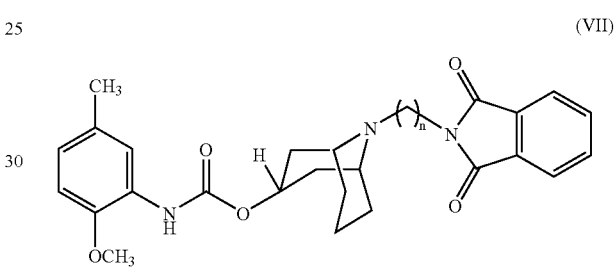

(VII)

wherein n is an integer from 1 to about 20, or a salt thereof.

17. A compound or salt thereof in accordance with aspect 16, wherein n=4, 6 or 10.

18. A compound of formula (VIII):

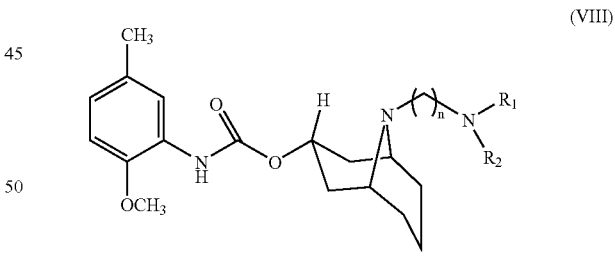

(VIII)

wherein n is an integer from 1 to about 20, and $R_1$ and $R_2$ are each independently selected from H, $C_{1-20}$ alkyl $C_{1-20}$ alkoxy, $C_{1-20}$ aminoalkyl, and $C_{1-20}$ aminoacyl, or a salt thereof.

19. A compound or salt thereof of aspect 18, wherein n=5, 6, 7, 8, 9 or 10.

20. A compound or salt thereof in accordance with aspect 18, wherein at least one of $R_1$ and $R_2$ is an aminoacyl moiety selected from the group consisting of an aspartyl moeity and a glutamyl moiety.

21. A compound or salt thereof in accordance with aspect 18, wherein at least one of $R_1$ and $R_2$ is an aspartyl moeity.

22. A compound of formula (IX):

(IX)

wherein n is an integer from 1 to about 20, m is an integer from 0 to about 20, and $R_1$ and $R_2$ are each independently selected from H, $C_{1-20}$ alkyl $C_{1-20}$ alkoxy, $C_{1-20}$ aminoalkyl, and $C_{1-20}$ aminoacyl, or a salt thereof.

23. A compound or salt thereof in accordance with aspect 22, wherein n=5, 6, 7, 8, 9 or 10.
24. A compound or salt thereof in accordance with aspect 22, wherein at least one of $R_1$ and $R_2$ is an aminoacyl moiety selected from the group consisting of an aspartyl moiety and a glutamyl moiety.
25. A compound or salt thereof in accordance with aspect 22, wherein at least one of $R_1$ and $R_2$ is an aspartyl moeity.
26. A method of synthesizing a compound of formula (VII):

(VII)

wherein n is an integer from 1 to about 20, the method comprising contacting a compound of formula (X):

(X)

with a compound of formula (XI):

(XI)

wherein n is an integer from 1 to about 20.

27. A method in accordance with aspect 26, wherein n=4, 6 or 10.
28. A method in synthesizing a compound of formula (I):

(I)

the method comprising contacting a compound of formula (VII):

(VII)

with hydrazine, wherein n is an integer from 1 to about 20.

29. A method of synthesizing a compound of formula (II):

(II)

the method comprising contacting a compound of formula (I):

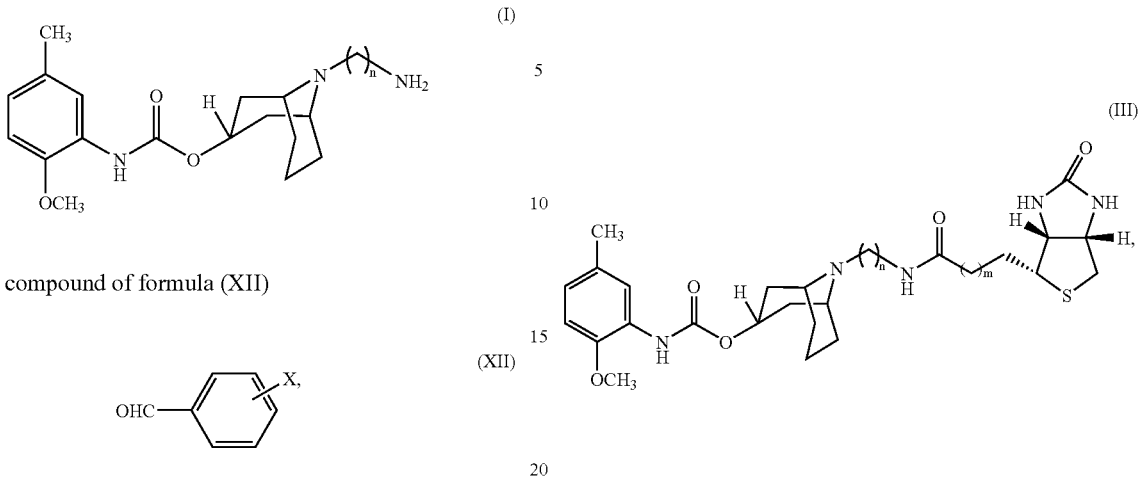

with a compound of formula (XII)

(XII)

wherein n is an integer from 1 to about 20, and wherein X is a halogen atom attached to the phenyl group at position 3 or 4, wherein the halogen atom is selected from the group consisting of Cl, Br, F, and I.

30. A method in accordance with aspect 29, wherein n=4 or 6.

31. A method of synthesizing a compound of formula (VI):

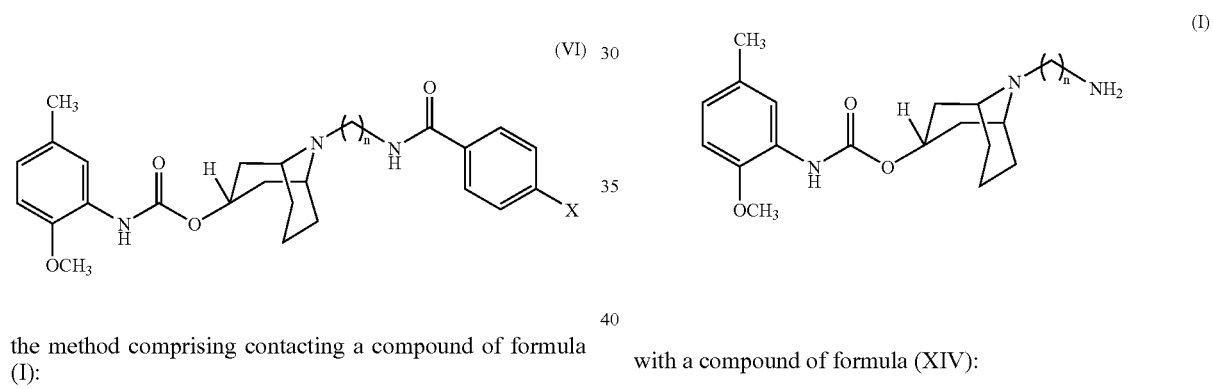

the method comprising contacting a compound of formula (I):

(I)

wherein n is an integer from 1 to about 20, and X is a halogen atom selected from the group consisting of Cl, Br, F, and I.

32. A method in accordance with aspect 31, wherein n=6.

33. A method of synthesizing a compound of formula (III):

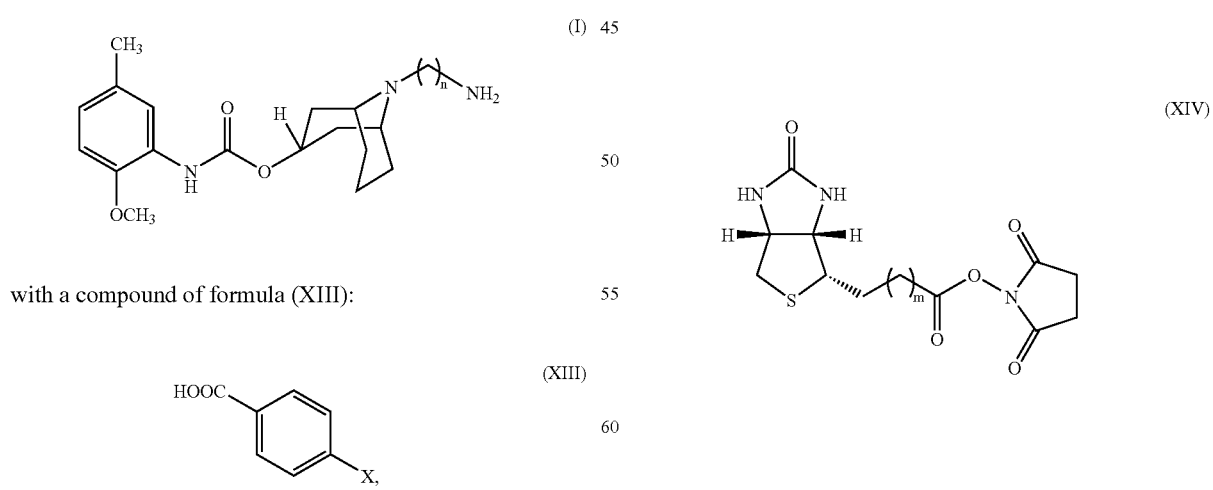

the method comprising contacting a compound of formula (I):

(I)

with a compound of formula (XIV):

(XIV)

wherein n is an integer from 1 to about 20.

34. A method in accordance with aspect 33, wherein m=3 and n=6 or 10.

35. A method of synthesizing a compound of formula (IV)

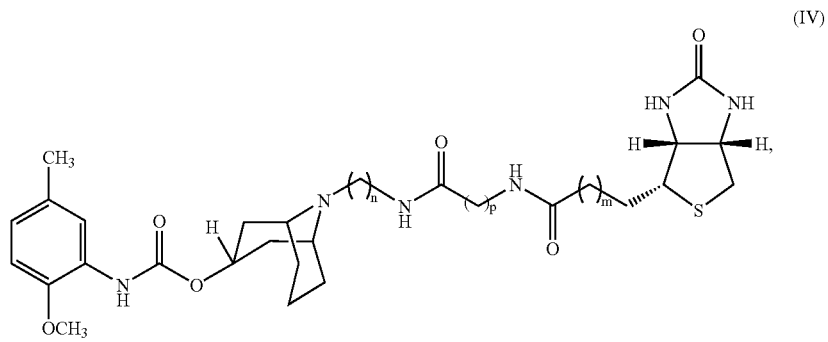

the method comprising contacting a compound of formula (I):

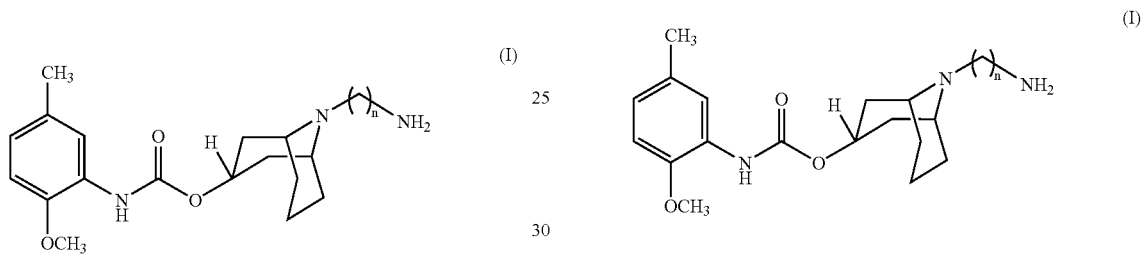

with a compound of formula (XV):

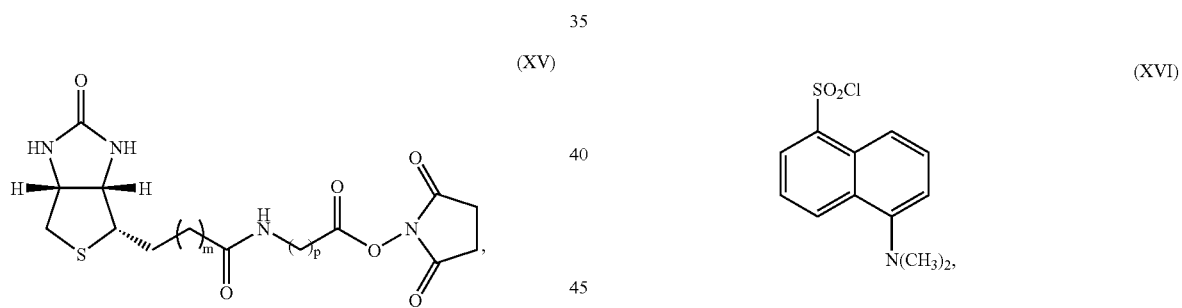

wherein m is an integer from 1 to about 20, n is an integer from 1 to about 20 and p is an integer from 1 to about 20.

36. A method in accordance with aspect 35, wherein m=3, n=6 or 10, and p=5.

37. A method of synthesizing a compound of formula (V):

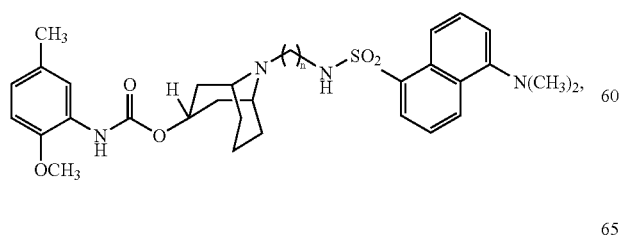

the method comprising contacting a compound of formula (I):

with a compound of formula (XVI):

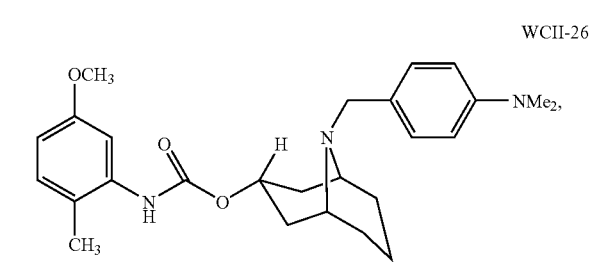

wherein n is an integer from 1 to about 20.

38. A method in accordance with aspect 37, wherein n=6.

39. A method of inducing apoptosis in a tumor cell, the method comprising contacting the cell with at least one σ2 receptor ligand or a salt thereof, wherein the at least one σ2 receptor ligand is selected from the group consisting of -continued

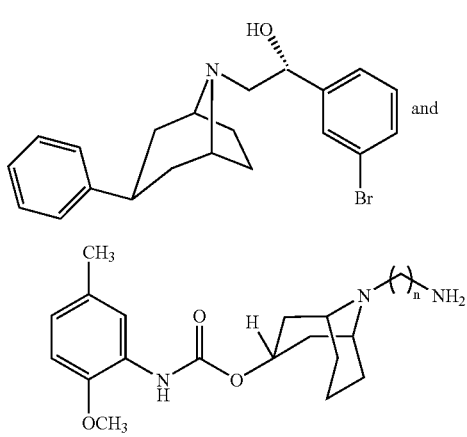

wherein n is an integer from 1 to about 20.
40. A method of inducing apoptosis in accordance with aspect 38, wherein n=6.
41. A method for treating a cancer, the method comprising administering to a subject in need of cancer therapy a therapeutically effective amount of a σ2 receptor ligand or a salt thereof, wherein the ligand is selected from the group consisting of

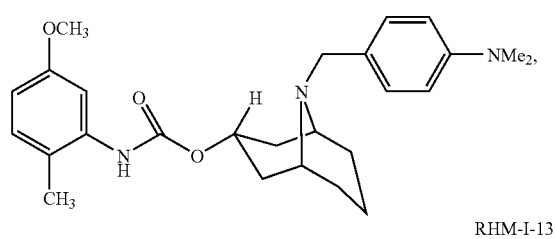

wherein n is an integer from 1 to about 20.
42. A method for treating a cancer in accordance with aspect 41, wherein n=6.
43. A method for treating a cancer in accordance with aspect 41, further comprising administering a chemotherapeutic agent.
44. A method for treating a cancer in accordance with aspect 43, wherein the chemotherapeutic agent is selected from the group consisting of doxorubicin, colchicine, adriamycin, vinblastine, digoxin, saquinivir, cisplatin and paclitaxel.
45. A method for treating a cancer in accordance with aspect 41, wherein the σ2 receptor ligand or a salt thereof is comprised by a pharmaceutical composition.
46. A compound or a salt thereof, wherein the compound is selected from the group consisting of

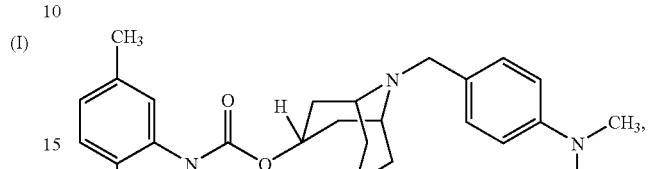

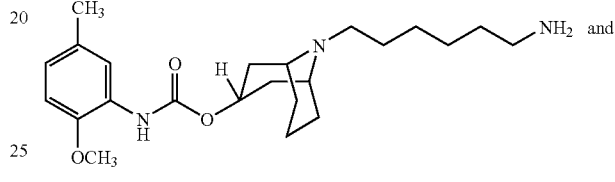

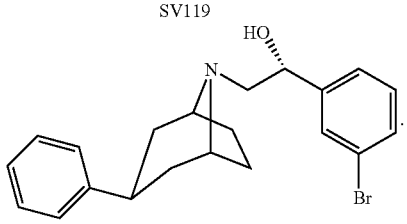

47. A compound or a salt thereof in accordance with aspect 46, wherein the compound is selected from the group consisting of

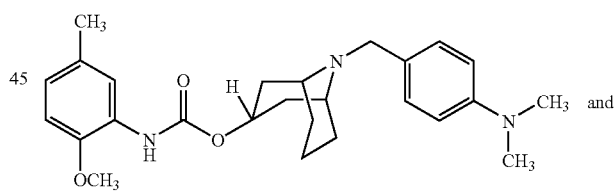

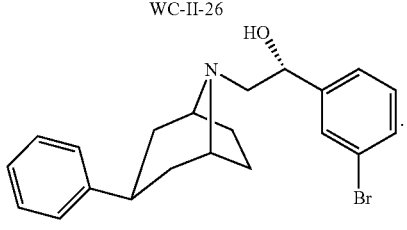

48. A pharmaceutical composition comprising at least one compound or salt thereof of aspect 46.

What is claimed is:
1. A compound or a salt thereof selected from the group consisting of

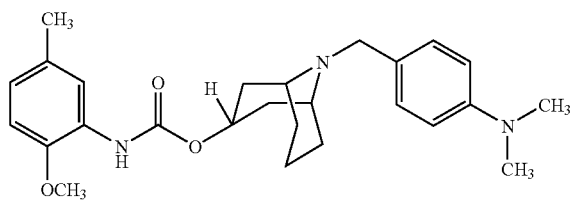
WC-II-26
and
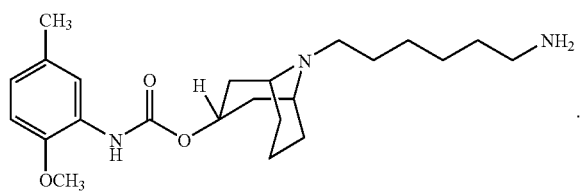
SV119
2. A compound or a salt thereof in accordance with claim 1, wherein the compound is
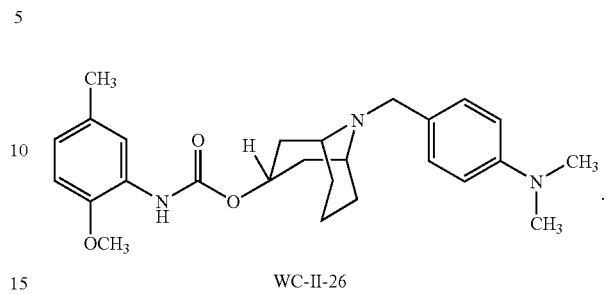
WC-II-26
3. A pharmaceutical composition comprising at least one compound or salt thereof of claim 1.
* * * * *